US012152052B2

(12) United States Patent
Freier

(10) Patent No.: US 12,152,052 B2
(45) Date of Patent: Nov. 26, 2024

(54) COMPOUNDS AND METHODS FOR REDUCING MECP2 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 18/472,506

(22) Filed: Sep. 22, 2023

(65) Prior Publication Data

US 2024/0124513 A1 Apr. 18, 2024

Related U.S. Application Data

(60) Provisional application No. 63/376,936, filed on Sep. 23, 2022.

(51) Int. Cl.
*C07H 21/04* (2006.01)
(52) U.S. Cl.
CPC .................................. *C07H 21/04* (2013.01)
(58) Field of Classification Search
CPC ........................................................ C07H 21/04
USPC ........................................................ 536/22.1
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |

(Continued)

FOREIGN PATENT DOCUMENTS

| | | |
|---|---|---|
| CN | 111150854 A | 5/2020 |
| WO | WO 1996/018736 | 6/1996 |

(Continued)

OTHER PUBLICATIONS

Sztainberg et al. Reversal of phenotypes in MECP2 duplication mice using genetic rescue or antisense oligonucleotides. Nature 528:123-139 (including Methods, Extended Data Figures, and Extended Data Tables). Dec. 3, 2015. (Year: 2015).*
NCBI Sequence Alignment: Blast two sequences, Dec. 18, 2023, RID: S21JY623114. (Year: 2023).*
Bajikar et al., "Modeling antisense oligonucleotide therapy in MECP2 duplication syndrome human iPSC-derived neurons" Presentation for BMES Annual Meeting (Oct. 14, 2022) San Antonio, TX: 1-16.
Bennett et al., "Antisense oligonucleotides as a tool for gene functionalization and target validation" Biochim Biophys Acta (1999) 1489(1): 19-30.
Branch et al., "A good antisense molecule is hard to find, " TIBS (1998) 23:45-50.
Chahrour et al., "MeCP2, a key contributor to neurological disease, activates and represses transcription" Science (2008) 320: 1224-1229.

(Continued)

Primary Examiner — Yih-Horng Shiao
(74) Attorney, Agent, or Firm — McNeill PLLC

(57) ABSTRACT

Provided are oligomeric compounds, methods, and pharmaceutical compositions for reducing the amount or activity of methyl CpG binding protein 2 (MECP2) RNA in a cell or animal, and in certain instances reducing the amount of MECP2 protein in a cell or animal Such oligomeric agents, oligomeric compounds, methods, and pharmaceutical compositions are useful to ameliorate at least one symptom or hallmark of a neurodevelopmental disease or disorder. Such neurodevelopmental diseases or disorders include MECP2 duplication syndrome. Such symptoms or hallmarks include autism, intellectual disability, motor dysfunction, hypotonia, global developmental delays, gastrointestinal symptoms, anxiety, epilepsy, recurrent respiratory tract infections, epileptic encephalopathy, and early death.

29 Claims, No Drawings

Specification includes a Sequence Listing.

(56) References Cited

U.S. PATENT DOCUMENTS

| | | |
|---|---|---|
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,687,616 B1 | 3/2010 | Bentwich et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 10,655,128 B2 | 5/2020 | Krieg et al. |
| 11,129,844 B2 | 9/2021 | Freier et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0009899 A1 | 1/2007 | Mounts |
| 2007/0031844 A1 | 2/2007 | Khvorova et al. |
| 2007/0134697 A1 | 6/2007 | Khvorova et al. |
| 2008/0039618 A1 | 2/2008 | Allerson et al. |
| 2009/0082297 A1 | 3/2009 | Lioy et al. |
| 2010/0190837 A1 | 7/2010 | Migawa et al. |
| 2010/0197762 A1 | 8/2010 | Swayze et al. |
| 2010/0247543 A1 | 9/2010 | Maes et al. |
| 2012/0171279 A1 | 7/2012 | Karelson et al. |
| 2013/0116301 A1 | 5/2013 | Freier et al. |
| 2013/0130378 A1 | 5/2013 | Manoharan et al. |
| 2013/0296400 A1 | 11/2013 | Monia et al. |
| 2014/0094504 A1 | 4/2014 | Guiducci et al. |
| 2014/0107330 A1 | 4/2014 | Freier et al. |

(56) References Cited

U.S. PATENT DOCUMENTS

| | | |
|---|---|---|
| 2015/0018540 A1 | 1/2015 | Prakash et al. |
| 2015/0099791 A1 | 4/2015 | Krieg et al. |
| 2015/0152410 A1 | 6/2015 | Krieg et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2018/0036335 A1 | 2/2018 | Freier |
| 2018/0044673 A1 | 2/2018 | Zoghbi et al. |
| 2018/0223282 A1 | 8/2018 | Krieg et al. |
| 2018/0320175 A1 | 11/2018 | Lee et al. |
| 2020/0095579 A1 | 3/2020 | Lundberg et al. |
| 2022/0226361 A1 | 7/2022 | Freier |

FOREIGN PATENT DOCUMENTS

| | | |
|---|---|---|
| WO | WO 2000/015265 | 3/2000 |
| WO | WO 2005/116204 | 12/2005 |
| WO | WO 2006/006948 | 1/2006 |
| WO | WO 2009/027349 | 3/2009 |
| WO | WO 2010/105096 | 9/2010 |
| WO | WO 2011/071232 | 6/2011 |
| WO | WO 2011/079307 | 6/2011 |
| WO | WO 2013/173608 | 11/2013 |
| WO | WO 2013/173635 | 11/2013 |
| WO | WO 2014/052393 | 4/2014 |
| WO | WO 2014/179620 | 11/2014 |
| WO | WO 2014/205445 | 12/2014 |
| WO | WO 2015/089419 | 6/2015 |
| WO | WO 2016/141145 | 9/2016 |
| WO | WO 2016/141236 * | 9/2016 |
| WO | WO 2016/145014 | 9/2016 |
| WO | WO 2016/149455 | 9/2016 |
| WO | WO 2017/015555 | 1/2017 |
| WO | WO 2017/189308 | 11/2017 |
| WO | WO 2019/157531 | 8/2019 |
| WO | WO 2020/212448 | 10/2020 |
| WO | WO 2020/227406 | 11/2020 |
| WO | WO 2021/142342 | 7/2021 |
| WO | 2022159712 A1 | 7/2022 |
| WO | WO 2023/133550 | 7/2023 |
| WO | 2024064854 A2 | 3/2024 |
| WO | 2024064858 A2 | 3/2024 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Collins et al., "Mild overexpression of MeCP2 causes a progressive neurological disorder in mice" Hum Mol Genet (2004) 13: 2679-2689.

Crooke et al., "Basic Principles of Antisense Therapeutics" Antisense Research and Application (1998) Chapter 1:1-50.

Crooke, ST., et al., "Antisense Drug Technology" Second Edition, CRC Press (2008) Chapters 1-28.

Crooke et al., "Pharmacokinetic Properties of Several Novel Oligonucleotide Analogs in mice" J. Pharmacol. Exp. Ther. (1996) 277, 923-937.

Dastidar et al. "Isoform-specific toxicity of Mecp2 in postmitotic neurons: Suppression of neurotoxicity of neurotoxcity by FoxG1" J Neurosci. (2012) 32(8): 2846-2855.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bcl-2/bcl-xLbispecific antisense oligonucleotide against tumors of diverse histologic origins" J. Natl. Cancer Inst. (2001) 93:463-471.

Gould et al., "The Open Field Test" Mood and Anxiety Related Phenotypes in Mice (2009) 1-20.

Jin et al., "RNAi-induced down-regulation of Mecp2 expression in the rat brain" Int J Dev Neurosci (2008) 26(5): 457-465.

Jones et al., "Methylated DNA and MeCP2 recruit histone deacetylase to repress transcription" Nat Genet. (1998) 19: 187-191.

Kabanov et al., "A new class of antivirals: antisense oligonucleotides combined with a hydrophobic substituent effectively inhibit influenza virus reproduction and synthesis of virus-specfic proteins in MDCK cells" FEBS Lett. (1990) 259, 327-330.

Letsinger et al., "Cholesteryl-conjugated oligonucleotides: Synthesis, properties, and activity as inhibitors of replication of human immunodeficiency virus in cell culture" Proc. Natl. Acad. Sci. USA (1989) 86, 6553-6556.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Manoharan et al., "Chemical Modifications to Improve Uptake and Bioavailability of Antisense Oligonucleotides" Ann. N.Y. Acad. Sci. (1992) 660, 306-309.

Manoharan et al., "Cholic Acid-Oligonucleotide Conjugates for Antisense Applications" Bioorg. Med. Chem. Lett. (1994) 4, 1053-1060.

Manoharan et al., "Introduction of a Lipophilic Thioether Tether in the Minor Groove of Nucleic Acids for Antisense Applications" Bioorg. Med. Chem. Lett. (1993) 3, 2765-2770.

Manoharan et al., "Lipidic Nucleic Acids" Tetrahedron Lett. (1995) 36, 3651-3654.

Manoharan et al., "Oligonucleotide Conjugates: Alteration of the Pharmacokinetic Properties of Antisense Agents" Nucleosides & Nucleotides (1995) 14, 969-973.

Mishra et al., "Improved leishmanicidal effect of phosphorotioate antisense oligonucleotides by LDL-mediated delivery" Biochim. Biophys. Acta (1995) 1264, 229-237.

Na et al., "GABAA receptor antagonism ameliorates behavioral and synaptic impairments associated with MeCP2 overexpression" Neuropsychopharmacology (2014) 39(8): 1946-1954.

Nan et al., "Transcriptional repression by the methyl-CpG-binding protein MeCP2 involves a histone deacetylase complex" Nature (1998) 393: 386-389.

New England Biolabs 1998/99 Catalog (cover page and pp. 121 and 284).

Nishina et al., "Chimeric Antisense Oligonucleotide Conjugated to α-Tocopherol" Molecular Therapy Nucleic Acids (2015) 4, e220.

Nishina et al., "Efficient In Vivo Delivery of siRNA to the Liver by Conjugation of α-Tocopherol" Molecular Therapy (2008) 16, 734-740.

Oberhauser et al., "Effective incorporation of 2'-O-methyl-oligonucleotides into liposomes and enhanced cell association through modification with thiocholesterol" Nucl. Acids Res. (1992) 20, 533-538.

Oka et al., "An oxazaphospholidine approach for the stereocontrolled synthesis of oligonucleoside phosphorothioates" J Am Chem Soc (2003) 125: 8307-8317.

Pandey et al. "Identification and Characterization of Modified Antisense Oligonucleotides Targeting DMPK in Mice and Nonhuman Primates for the Treatment of Myotonic Dysrophy Type 1" J Pharmacol Exp Ther. (2015) 355(2):329-340.

Ramocki et al., "The MECP2 duplication syndrome" Am J Med Genet A (2010) 152A: 1079-10188.

Rett Syndrome Research Trust "Developing an Antisense Oligonucleotide Therapeutic for MECP2 Duplication Syndrome" [video] Cure MDS Webinar (uploaded on Mar. 18, 2023 from https://www.youtube.com/watch?v=qpd9jANIWms).

Reynolds et al., "Rational siRNA design for RNA interference" Nature Biotechnology (2004) 22(3):326-330.

Saison-Behmoaras et al., "Short modified antisense oligonucleotides directed against Ha-ras point mutation induce selective cleavage of the mRNA and inhibit T24 cells proliferation" EMBO J. (1991) 10, 1111-1118.

Samaco et al., "Crh and Oprml mediate anxiety-related behavior and social approach in a mouse model of MECP2 duplication syndrome" Nat Genet (2012) 44(2): 206-211.

(56) References Cited

OTHER PUBLICATIONS

Sandweiss et al., "Advances in understanding of Rett syndrome and MECP2 duplication syndrome: prospects for future therapies" Lancet Neurol (2020) 19: 689-698.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Shao et al., "Antisense oligonucleotide therapy in a humanized mouse model of MECP2 duplication syndrome" Sci Transl Med (2021) 13: 1-11.
Shao et al., "Antisense oligonucleotide therapy for MECP2 duplication syndrome" Poster Presentation for Society for Neuroscience Annual Meeting 2019 (Oct. 19, 2019) Chicago, IL.
Shao et al., "Antisense oligonucleotide therapy for MECP2 duplication syndrome" Poster Presentation for BCM Graduate Symposium 2017 (Oct. 24, 2017).
Shao et al., "Testing the safety boundaries of MECP2 expression using Antisense Oligonucleotides" Poster Presentation for RNA & Oligocnucleotide Therapeutics (CSHL) 2017 (Mar. 29, 2017).
Shao et al., "Optimizing antisense oligonucleotide therapy in a mouse model that exclusively express two copies of human MECP2" Abstract for Systems Biology: Global Regulation of Gene Expression (CSHL) 2017 (Feb. 26, 2017).
Shea et al., "Synthesis, hydridization properties and antiviral activity of lipid-oligodeoxynucleotide conjugates" *Nucl. Acids Res.* (1990) 18, 3777-3783.
Svinarchuk et al., "Inhibition of HIV proliferation in MT-4 cells by antisense oligonucleotide conjugated to lipophilic groups" *Biochimie* (1993) 75, 49-54.
Sztainberg et al. "Reversal of phenotypes in MECP2 duplication mice using genetic rescue or antisense oligonucleotides" Nature (2015) 528:123-126.
Sztainberg et al., "Optimization of an antisense oligonucleotide therapy in a novel MECP2 duplication mouse model" Poster Presentation for Society for Neuroscience Annual Meeting 2016 (Nov. 12, 2016) San Diego, CA.
Walf et al., "The use of the elevated plus maze as an assay of anxiety-related behavior in rodents" Nat Protoc (2007) 2(2): 322-328.
Wan et al., "Synthesis, biophysical properties and biological activity of second generation antisense oligonucleotides containing chiral phosphorothioate linkages" Nucl Acid Res (2014) 42: 13456-13468.
Weaving et al., "Rett syndrome: clinical review and genetic update" J Med Genet (2005) 42: 1-7.
Woolf et al., "Specificity of antisense oligonucleotides in vivo" PNAS (1992) 89: 7305-7309.
Zhang et al., [Knocking down rat Mecp2 expression by RNAi] Beijing Da Xue Xue Bao Yi Xue Ban (2006) 38: 529-532.
Extended European Search Report for 16759471.2 dated Jul. 26, 2018.
Partial Search Report for 16759530.5 date Oct. 1, 2018.
Extended EP Search Report for 22153020.7 dated Aug. 5, 2022.
International Search Report for PCT/US16/20610 dated May 20, 2016.
International Search Report for PCT/US2016/020771 dated Aug. 5, 2016.
International Search Report for PCT/US2021/057344 dated Mar. 1, 2022.
International Search Report for PCT/US2023/074829 dated Apr. 2, 2024, 11 pages.
International Search Report for PCT/US2023/074833 dated Mar. 14, 2024, 14 pages.

* cited by examiner

COMPOUNDS AND METHODS FOR REDUCING MECP2 EXPRESSION

SEQUENCE LISTING

The present application is being filed along with a Sequence Listing in electronic format. The Sequence Listing is provided as a file entitled BIOL0429SEQ.xml, created on Sep. 11, 2023, which is 118 Kb in size. The information in the electronic format of the sequence listing is incorporated herein by reference in its entirety.

FIELD

Provided are oligomeric compounds, methods, and pharmaceutical compositions for reducing the amount or activity of methyl CpG binding protein 2 (MECP2) RNA in a cell or animal, and in certain instances, reducing MECP2 protein in a cell or animal. Such oligomeric agents, oligomeric compounds, methods, and pharmaceutical compositions are useful to ameliorate at least one symptom or hallmark of a neurodevelopmental disease or disorder. Such neurodevelopmental diseases or disorders include MECP2 duplication syndrome. Such symptoms or hallmarks include autism, intellectual disability, motor dysfunction, hypotonia, global developmental delays, gastrointestinal symptoms, anxiety, epilepsy, recurrent respiratory tract infections, epileptic encephalopathy, and early death.

BACKGROUND

Methyl CpG binding protein 2 (MECP2) is located on chromosome Xq28 and plays a fundamental role in epigenetics, controlling chromatin states, and expression of thousands of genes (Chahrour et al., Science, 2008, 320:1224-1229; Nan et al., Nature, 1998, 393:386-389; Jones et al., Nat. Genet., 1998, 19:187-191). MECP2 duplication syndrome caused by overexpression of MECP2 is characterized by autism, intellectual disability, motor dysfunction, hypotonia, global developmental delays, gastrointestinal symptoms, anxiety, epilepsy, recurrent respiratory tract infections, epileptic encephalopathy, and early death, typically in males (Ramocki et al., Am J Med Genet A, 2010, 152A:1079-1088).

Currently there is a lack of acceptable options for treating such neurological disorders. It is therefore an object herein to provide compounds and pharmaceutical compositions for the treatment of such diseases and disorders.

SUMMARY

Oligomeric agents, oligomeric compounds, and pharmaceutical compositions of certain embodiments described herein are useful for reducing or inhibiting MECP2 expression in a cell or animal. In certain embodiments, MECP2 RNA or protein levels can be reduced in a cell or animal. Also provided are methods of treating MECP2 Duplication Syndrome.

DETAILED DESCRIPTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included" is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, treatises, and GenBank, ENSEMBL, and NCBI reference sequence records, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

As used herein, "2'-deoxynucleoside" means a nucleoside comprising a 2'-H(H) deoxyfuranosyl sugar moiety. In certain embodiments, a 2'-deoxynucleoside is a 2'-β-D-deoxynucleoside and comprises a 2'-β-D-deoxyribosyl sugar moiety, which has the β-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" means a $OCH_2CH_2OCH_3$ group in place of the 2'-OH group of a furanosyl sugar moiety. A "2'-MOE sugar moiety" or a "2'-O-methoxyethyl sugar moiety" or "2'-MOE ribosyl sugar moiety" means a sugar moiety with a $OCH_2CH_2OCH_3$ group in place of the 2'-OH group of a furanosyl sugar moiety. Unless otherwise indicated, a 2'-MOE sugar moiety is in the β-D-ribosyl configuration. "MOE" means O-methoxyethyl.

As used herein, "2'-MOE nucleoside" means a nucleoside comprising a 2'-MOE sugar moiety.

As used herein, "5-methylcytosine" means a cytosine modified with a methyl group attached to the 5 position. A 5-methylcytosine is a modified nucleobase.

As used herein, "ameliorate" in reference to a treatment means improvement in at least one symptom or hallmark relative to the same symptom or hallmark in the absence of the treatment. In certain embodiments, amelioration is the reduction in the severity or frequency of a symptom or hallmark or the delayed onset or slowing of progression in the severity or frequency of a symptom or hallmark. In certain embodiments, the symptom or hallmark is one or more of autism, intellectual disability, motor dysfunction, hypotonia, global developmental delays, gastrointestinal symptoms, anxiety, epilepsy, recurrent respiratory tract infections, epileptic encephalopathy, and early death. The progression or severity of indicators may be determined by subjective or objective measures, which are known to those skilled in the art.

As used herein, "cell-targeting moiety" means a conjugate moiety or portion of a conjugate moiety that is capable of binding to a particular cell type or particular cell types.

As used herein, "cerebrospinal fluid" or "CSF" means the fluid filling the space around the brain and spinal cord. "Artificial cerebrospinal fluid" or "aCSF" means a prepared or manufactured fluid that has certain properties (e.g., osmolarity, pH, and/or electrolytes) similar to cerebrospinal fluid and is biocompatible with CSF.

As used herein, "chirally controlled" in reference to an internucleoside linkage means chirality at that linkage is enriched for a particular stereochemical configuration.

As used herein, "chirally enriched" in reference to a population means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom as defined herein. Chirally enriched populations of molecules having multiple chiral centers within each molecule may contain one or more stereorandom chiral centers. In certain embodiments, the molecules are modified oligonucleotides. In certain embodiments, the molecules are oligomeric compounds comprising modified oligonucleotides. In certain embodiments, the chiral center is at the phosphorous atom of a phosphorothioate internucleoside linkage. In certain embodiments, the chiral center is at the phosphorous atom of a mesyl phosphoramidate internucleoside linkage.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide and the nucleobases of another nucleic acid or one or more regions thereof are capable of hydrogen bonding with one another when the nucleobase sequence of the oligonucleotide and the other nucleic acid are aligned in opposing directions. "Complementary region" in reference to a region of an oligonucleotide means that at least 70% of the nucleobases of that region and the nucleobases of another nucleic acid or one or more regions thereof are capable of hydrogen bonding with one another when the nucleobase sequence of the oligonucleotide and the other nucleic acid are aligned in opposing directions. Complementary nucleobases mean nucleobases that are capable of forming hydrogen bonds with one another. Complementary nucleobase pairs include adenine (A) and thymine (T), adenine (A) and uracil (U), cytosine (C) and guanine (G), 5-methylcytosine (mC) and guanine (G). Certain modified nucleobases that pair with unmodified nucleobases or with other modified nucleobases are known in the art and are not considered complementary nucleobases as defined herein unless indicated otherwise. For example, inosine can pair, but is not considered complementary, with adenosine, cytosine, or uracil. Complementary oligonucleotides and/or nucleic acids need not have nucleobase complementarity at each nucleoside. Rather, some mismatches are tolerated. As used herein, "fully complementary" or "100% complementary" in reference to an oligonucleotide means that the oligonucleotide is complementary to another oligonucleotide or nucleic acid at each nucleobase of the shorter of the two oligonucleotides, or at each nucleoside if the oligonucleotides are the same length.

As used herein, "complementary region" in reference to an oligonucleotide is the range of nucleobases of the oligonucleotide that is complementary with a second oligonucleotide or target nucleic acid.

As used herein, "conjugate group" means a group of atoms that is directly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that modifies one or more properties of a molecule compared to the identical molecule lacking the conjugate moiety, including but not limited to pharmacodynamics, pharmacokinetics, stability, binding, absorption, tissue distribution, cellular distribution, cellular uptake, charge, and clearance.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "deoxy region" means a region of 5-12 contiguous nucleotides, wherein at least 70% of the nucleosides comprise a β-D-2'-deoxyribosyl sugar moiety. In certain embodiments, a deoxy region is the gap of a gapmer. In certain embodiments, a deoxy region supports RNase H activity.

As used herein, "diluent" means an ingredient in a composition that lacks pharmacological activity but is pharmaceutically necessary or desirable. For example, the diluent in an injected composition can be a liquid, e.g., aCSF, PBS, or saline solution.

As used herein, "double-stranded" in reference to a region or an oligonucleotide, means a duplex formed by complementary strands of nucleic acids (including, but not limited to oligonucleotides) hybridized to one another. In certain embodiments, the two strands of a double-stranded region are separate molecules. In certain embodiments, the two strands are regions of the same molecule that has folded onto itself (e.g., a hairpin structure).

As used herein, "duplex" or "duplex region" means the structure formed by two oligonucleotides or portions thereof that are hybridized to one another.

As used herein, "gapmer" means a modified oligonucleotide comprising an internal region positioned between external regions having one or more nucleosides, wherein the nucleosides comprising the internal region are chemically distinct from the nucleoside or nucleosides comprising the external regions, and wherein the modified oligonucleotide supports RNAse H cleavage. The internal region may be referred to as the "gap" and the external regions may be referred to as the "wings." In certain embodiments, the internal region is a deoxy region. The positions of the internal region or gap refer to the order of the nucleosides of the internal region and are counted starting from the 5'-end of the internal region. Unless otherwise indicated, "gapmer" refers to a sugar motif. In certain embodiments, the internal region is a "deoxy region". In certain embodiments, each nucleoside of the gap is a 2'-β-D-deoxynucleoside. In certain embodiments, the gap comprises one 2'-substituted nucleoside at position 1, 2, 3, 4, or 5 of the gap, and the remainder of the nucleosides of the gap are 2'-β-D-deoxynucleosides. As used herein, the term "MOE gapmer" indicates a gapmer having a gap comprising 2'-β-D-deoxynucleosides and wings comprising 2'-MOE nucleosides. As used herein, the term "mixed wing gapmer" indicates a gapmer having wings comprising modified nucleosides comprising at least two different sugar modifications. Unless otherwise indicated, a gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to reduction of the amount or activity of the target nucleic acid by the action of an oligomeric agent, oligomeric compound, modified oligonucleotide, antisense compound, or antisense agent.

As used herein, "hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

As used herein, "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate internucleoside linkage" or "PS internucleoside linkage" is a modified internucleoside linkage in which one of the non-bridging oxygen atoms of a phosphodiester internucleoside linkage is replaced with a sulfur atom. As used herein, "linked nucleosides" are nucleosides that are connected in a contiguous sequence (i.e., no additional nucleosides are presented between those that are linked).

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "mismatch" or "non-complementary" means a nucleobase of a first nucleic acid sequence that is not complementary with the corresponding nucleobase of a second nucleic acid sequence or target nucleic acid when the first and second nucleic acid sequences are aligned in opposing directions.

As used herein, "motif" means the pattern of unmodified and/or modified sugar moieties, nucleobases, and/or internucleoside linkages, in an oligonucleotide.

As used herein, "modified nucleoside" means a nucleoside comprising a modified nucleobase and/or a modified sugar moiety.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. A nucleobase is a heterocyclic moiety. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one other nucleobase. A "5-methylcytosine" is a modified nucleobase. A universal base is a modified nucleobase that can pair with any one of the five unmodified nucleobases.

As used herein, "nucleobase sequence" means the order of contiguous nucleobases in a nucleic acid or oligonucleotide independent of any sugar or internucleoside linkage modification.

As used herein, "the nucleobase sequence of" a reference SEQ ID NO, refers only to the nucleobase sequence provided in such SEQ ID NO and therefore, unless otherwise indicated, includes compounds wherein each sugar moiety and each internucleoside linkage, independently, is modified or unmodified, irrespective of the presence or absence of modifications indicated in the referenced SEQ ID NO.

As used herein, "nucleoside" means a compound or fragment of a compound comprising a nucleobase and a sugar moiety. The nucleobase and sugar moiety are each, independently, unmodified or modified.

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound.

The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications. An oligonucleotide may be paired with a second oligonucleotide that is complementary to the oligonucleotide or it may be unpaired. A "single-stranded oligonucleotide" is an unpaired oligonucleotide. A "double-stranded oligonucleotide" is an oligonucleotide that is paired with a second oligonucleotide.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspensions, and lozenges for the oral ingestion by a subject. In certain embodiments, a pharmaceutically acceptable carrier or diluent is sterile water, sterile saline, sterile buffer solution or sterile artificial cerebrospinal fluid.

As used herein "pharmaceutically acceptable salt(s)" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "RNA" means an RNA transcript and includes pre-mRNA and mature mRNA unless otherwise specified.

As used herein, "RNAi agent" means an antisense agent that acts, at least in part, through RISC or Ago2 to modulate a target nucleic acid and/or protein encoded by a target nucleic acid. RNAi agents include, but are not limited to double-stranded siRNA, single-stranded RNAi (ssRNAi), and microRNA, including microRNA mimics RNAi agents may comprise conjugate groups and/or terminal groups. In certain embodiments, an RNAi agent modulates the amount and/or activity, of a target nucleic acid. The term RNAi agent excludes antisense agents that act through RNase H.

As used herein, "RNase H agent" means an antisense agent that acts through RNase H to modulate a target nucleic acid and/or protein encoded by a target nucleic acid. In certain embodiments, RNase H agents are single-stranded. In certain embodiments, RNase H agents are double-stranded. RNase H compounds may comprise conjugate groups and/or terminal groups. In certain embodiments, an RNase H agent modulates the amount and/or activity of a target nucleic acid. The term RNase H agent excludes antisense agents that act principally through RISC/Ago2.

As used herein, "single-stranded" means a nucleic acid (including but not limited to an oligonucleotide) that is unpaired and is not part of a duplex. Single-stranded compounds are capable of hybridizing with complementary nucleic acids to form duplexes, at which point they are no longer single-stranded.

As used herein, "stereorandom" or "stereorandom chiral center" in the context of a population of molecules of identical molecular formula means a chiral center that is not controlled during synthesis, or enriched following synthesis, for a particular absolute stereochemical configuration. The stereochemical configuration of a chiral center is considered random when it is the result of a synthetic method that is not designed to control the stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center ("racemic"). In certain embodiments, the stereorandom chiral center is not racemic because one absolute configuration predominates following synthesis, e.g., due to the action of non-chiral reagents near the enriched stereochemistry of an adjacent sugar moiety. In certain embodiments, a stereorandom chiral center is at the phosphorous atom of a stereorandom phosphorothioate or mesyl phosphoroamidate internucleoside linkage.

As used herein, "subject" means a human or non-human animal. The terms "subject", "animal", and "individual" are used interchangeably. In certain embodiments, the subject is human.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests. In certain embodiments, a hallmark is apparent on a brain MRI scan. In certain embodiments, symptoms and hallmarks include autism, intellectual disability, motor dysfunction, hypotonia, global developmental delays, gastrointestinal symptoms, anxiety, epilepsy, recurrent respiratory tract infections, epileptic encephalopathy, and early death.

As used herein, "target nucleic acid" and "target RNA" mean a nucleic acid that an oligomeric compound is designed to affect. Target RNA means an RNA transcript and includes pre-mRNA and mature mRNA unless otherwise specified.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "treating" means improving a subject's disease or condition by administering an oligomeric compound, an oligomeric duplex, or an antisense agent described herein. In certain embodiments, treating a subject improves a symptom relative to the same symptom in the absence of the treatment. In certain embodiments, treatment reduces in the severity or frequency of a symptom, or delays the onset of a symptom, slows the progression of a symptom, or slows the severity or frequency of a symptom.

As used herein, "therapeutically effective amount" means an amount of a pharmaceutical agent or composition that provides a therapeutic benefit to an animal. For example, a therapeutically effective amount improves a symptom of a disease.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, antisense activity is the modulation of splicing of a target pre-mRNA.

As used herein, "antisense agent" means an antisense compound and optionally one or more additional features, such as a sense compound.

As used herein, "antisense compound" means an antisense oligonucleotide and optionally one or more additional features, such as a conjugate group.

As used herein, "sense compound" means a sense oligonucleotide and optionally one or more additional features, such as a conjugate group.

As used herein, "antisense oligonucleotide" means an oligonucleotide, including the oligonucleotide portion of an antisense compound, that is capable of hybridizing to a target nucleic acid and is capable of at least one antisense activity. Antisense oligonucleotides include but are not limited to antisense RNAi oligonucleotides and antisense RNase H oligonucleotides.

As used herein, "sense oligonucleotide" means an oligonucleotide, including the oligonucleotide portion of a sense compound, that is capable of hybridizing to an antisense oligonucleotide.

Certain Embodiments

The present disclosure provides the following non-limiting numbered embodiments:

Embodiment 1. A modified oligonucleotide according to the following chemical structure:

(SEQ ID NO: 19)

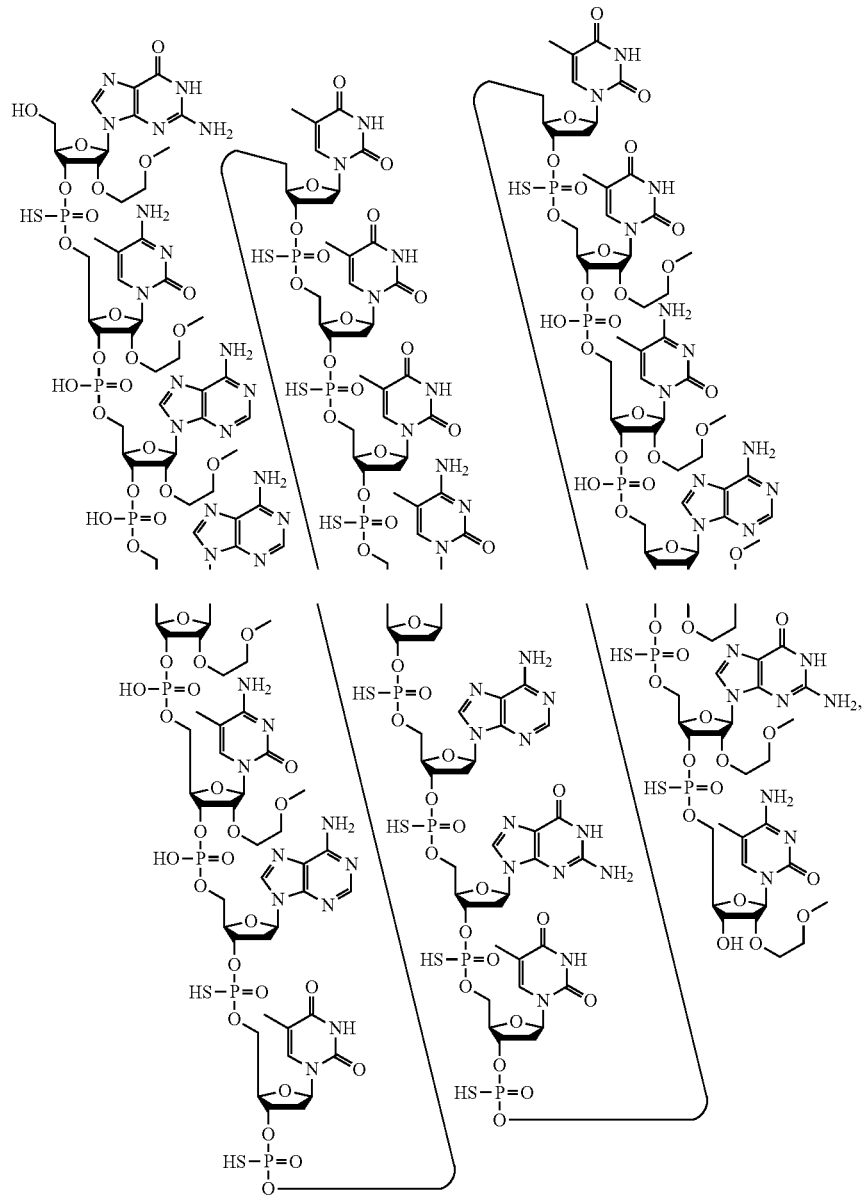

or a pharmaceutically acceptable salt thereof.

Embodiment 2. The modified oligonucleotide of embodiment 1, which is a pharmaceutically acceptable salt comprising one or more cations selected from sodium, potassium, calcium, and magnesium.

Embodiment 3. The modified oligonucleotide of embodiment 1, which is the sodium salt or the potassium salt.

Embodiment 4. A modified oligonucleotide according to the following chemical structure:

(SEQ ID NO: 19)

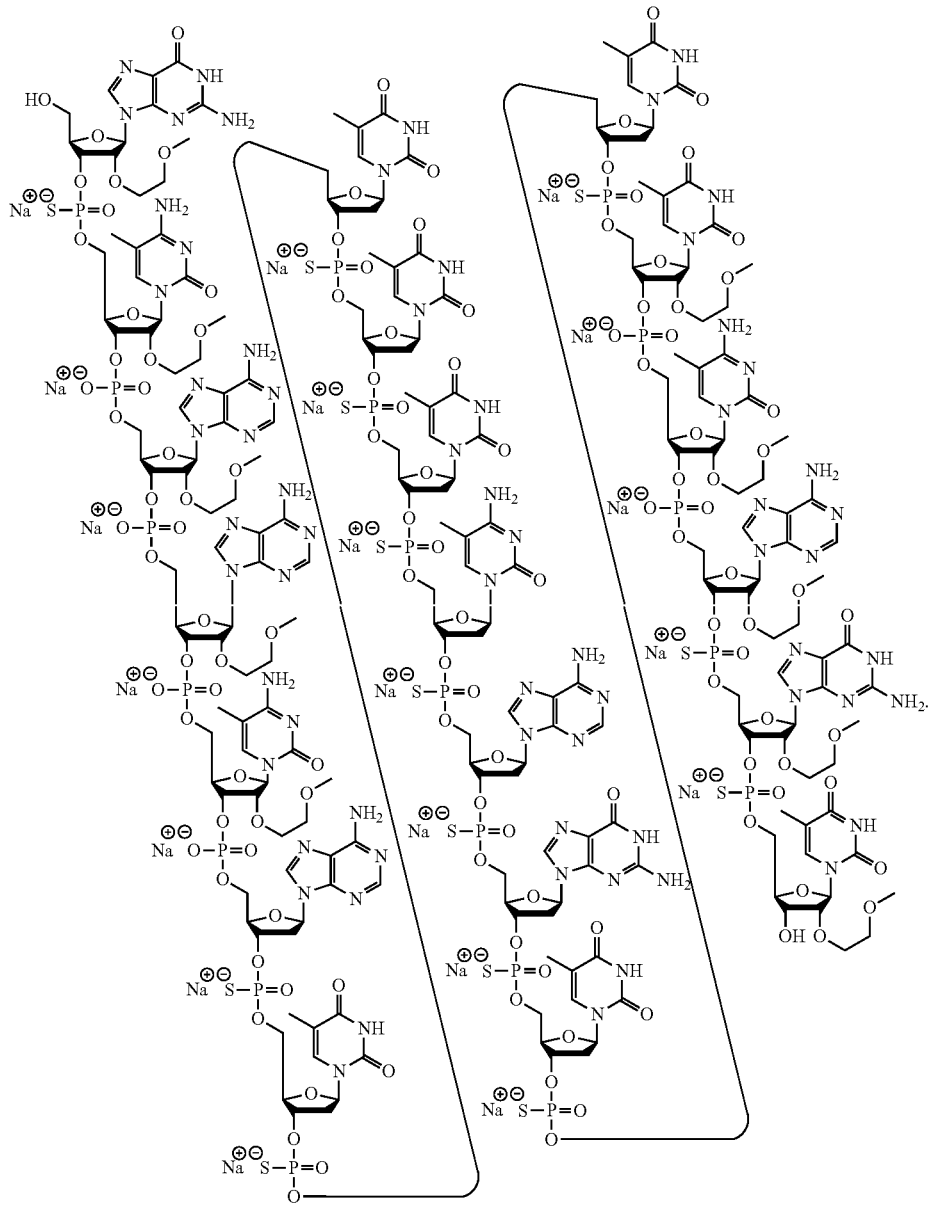

Embodiment 5. An oligomeric compound comprising a modified oligonucleotide according to the following chemical notation:

(SEQ ID NO: 19)
$G_{es}{}^mC_{eo}A_{eo}A_{eo}{}^mC_{eo}A_{ds}T_{ds}T_{ds}T_{ds}T_{ds}{}^mC_{ds}A_{ds}G_{ds}T_{ds}T_{ds}T_{eo}{}^mC_{eo}A_{es}G_{es}{}^mC_{e'}$ wherein
A=an adenine nucleobase,
$^mC$=a 5-methylcytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 6. A population of modified oligonucleotides of embodiment 1, wherein all of the phosphorothioate internucleoside linkages of the modified oligonucleotide are stereorandom.

Embodiment 7. A pharmaceutical composition comprising a modified oligonucleotide of embodiment 1 and a pharmaceutically acceptable diluent.

Embodiment 8. The pharmaceutical composition of embodiment 7, wherein the pharmaceutically acceptable diluent is phosphate-buffered saline or artificial cerebrospinal fluid.

Embodiment 9. The pharmaceutical composition of embodiment 8, wherein the pharmaceutical composition consists essentially of the modified oligonucleotide and the phosphate-buffered saline or the artificial cerebrospinal fluid.

Embodiment 10. A population of modified oligonucleotides of embodiment 2, wherein all of the phosphorothioate internucleoside linkages of the modified oligonucleotide are stereorandom.

Embodiment 11. A pharmaceutical composition comprising a modified oligonucleotide of embodiment 2 and a pharmaceutically acceptable diluent.

Embodiment 12. The pharmaceutical composition of embodiment 11, wherein the pharmaceutically acceptable diluent is phosphate-buffered saline or artificial cerebrospinal fluid.

Embodiment 13. The pharmaceutical composition of embodiment 12, wherein the pharmaceutical composition consists essentially of the modified oligonucleotide and the phosphate-buffered saline or the artificial cerebrospinal fluid.

Embodiment 14. A population of modified oligonucleotides of embodiment 4, wherein all of the phosphorothioate internucleoside linkages of the modified oligonucleotide are stereorandom.

Embodiment 15. A pharmaceutical composition comprising a modified oligonucleotide of embodiment 4 and a pharmaceutically acceptable diluent.

Embodiment 16. The pharmaceutical composition of embodiment 15, wherein the pharmaceutically acceptable diluent is phosphate-buffered saline or artificial cerebrospinal fluid.

Embodiment 17. The pharmaceutical composition of embodiment 16, wherein the pharmaceutical composition consists essentially of the modified oligonucleotide and the phosphate-buffered saline or the artificial cerebrospinal fluid.

Embodiment 18. A population of oligomeric compounds of embodiment 5, wherein all of the phosphorothioate internucleoside linkages of the oligomeric compound are stereorandom.

Embodiment 19. A pharmaceutical composition comprising an oligomeric compound of embodiment 5 and a pharmaceutically acceptable diluent.

Embodiment 20. The pharmaceutical composition of embodiment 19, wherein the pharmaceutically acceptable diluent is phosphate-buffered saline or artificial cerebrospinal fluid.

Embodiment 21. The pharmaceutical composition of embodiment 20, wherein the pharmaceutical composition consists essentially of the oligomeric compound and the phosphate-buffered saline or the artificial cerebrospinal fluid.

Embodiment 22. A pharmaceutical composition comprising a population of embodiment 6 and a pharmaceutically acceptable diluent.

Embodiment 23. The pharmaceutical composition of embodiment 22, wherein the pharmaceutically acceptable diluent is phosphate-buffered saline or artificial cerebrospinal fluid.

Embodiment 24. A pharmaceutical composition comprising a population of embodiment 10 and a pharmaceutically acceptable diluent.

Embodiment 25. The pharmaceutical composition of embodiment 24, wherein the pharmaceutically acceptable diluent is phosphate-buffered saline or artificial cerebrospinal fluid.

Embodiment 26. A pharmaceutical composition comprising a population of embodiment 14 and a pharmaceutically acceptable diluent.

Embodiment 27. The pharmaceutical composition of embodiment 26, wherein the pharmaceutically acceptable diluent is phosphate-buffered saline or artificial cerebrospinal fluid.

Embodiment 28. A pharmaceutical composition comprising a population of embodiment 18 and a pharmaceutically acceptable diluent.

Embodiment 29. The pharmaceutical composition of embodiment 28, wherein the pharmaceutically acceptable diluent is phosphate-buffered saline or artificial cerebrospinal fluid.

Embodiment 30. A method comprising administering to a subject a modified oligonucleotide of any of embodiments 1-4, an oligomeric compound of embodiment 5, a population of any of embodiments 6, 10, 14, and 18, or a pharmaceutical composition of any of embodiments 7-9, 11-13, 15-17, and 19-29.

Embodiment 31. The method of embodiment 30, wherein the subject has a disease or disorder associated with MECP2.

Embodiment 32. The method of embodiment 31, wherein the disease or disorder associated with MECP2 is a neurodevelopmental disease or disorder.

Embodiment 33. The method of embodiment 31 or embodiment 32, wherein the disease or disorder associated with MECP2 is MECP2 Duplication Syndrome.

Embodiment 34. A method of treating a disease or disorder associated with MECP2 comprising administering to a subject having or at risk for developing a disease or disorder associated with MECP2 a therapeutically effective amount of a modified oligonucleotide of any of embodiments 1-4, an oligomeric compound of embodiment 5, a population of any of embodiments 6, 10, 14, and 18, or a pharmaceutical composition of any of embodiments 7-9, 11-13, 15-17, and 19-29; and thereby treating the disease or disorder associated with MECP2.

Embodiment 35. The method of embodiment 34, wherein the disease or disorder associated with MECP2 is a neurodevelopmental disease or disorder.

Embodiment 36. The method of embodiment 34 or embodiment 35, wherein the disease or disorder associated with MECP2 is MECP2 Duplication Syndrome.

Embodiment 37. The method of any of embodiments 34-36, wherein at least one symptom or hallmark of the disease or disorder associated with MECP2 is ameliorated.

Embodiment 38. The method of embodiment 37, wherein the symptom or hallmark is autism, intellectual disability, motor dysfunction, hypotonia, global developmental delays, gastrointestinal symptoms, anxiety, epilepsy, recurrent respiratory tract infections, epileptic encephalopathy, or early death.

Embodiment 39. The method of any one of embodiments 34-38, wherein the disease or disorder associated with MECP2 is associated with an elevated level of MECP2 in the subject.

Embodiment 40. The method of any of embodiments 34-39, wherein administering the modified oligonucleotide, oligomeric compound, the population, or the pharmaceutical composition reduces seizures, reduces or delays cognitive impairment, reduces or delays intellectual disabilities, reduces or delays symptoms of autism, reduces anxiety, or reduces gastrointestinal symptoms in the subject; or improves motor function, motor development, muscle tone, cognitive development, speech, or social skill development in the subject.

Embodiment 41. The method of any of embodiments 31-40, wherein the subject is human.

Embodiment 42. A method of reducing expression of MECP2 in a cell comprising contacting the cell with a modified oligonucleotide of any of embodiments 1-4, an oligomeric compound of embodiment 5, a population of any of embodiments 6, 10, 14, and 18, or a pharmaceutical composition of any of embodiments 7-9, 11-13, 15-17, and 19-29.

Embodiment 43. The method of embodiment 42, wherein the cell is a neuron.

Embodiment 44. The method of embodiment 42 or embodiment 43, wherein the cell is a human cell.

Embodiment 45. Use of a modified oligonucleotide of any of embodiments 1-4, an oligomeric compound of embodiment 5, a population of any of embodiments 6, 10, 14, and 18, or a pharmaceutical composition of any of embodiments 7-9, 11-13, 15-17, and 19-29 for treating a disease or disorder associated with MECP2.

Embodiment 46. Use of a modified oligonucleotide of any of embodiments 1-4, an oligomeric compound of embodiment 5, a population of any of embodiments 6, 10, 14, and 18, or a pharmaceutical composition of any of embodiments 7-9, 11-13, 15-17, and 19-29 in the manufacture of a medicament for treating a disease or disorder associated with MECP2.

Embodiment 47. The use of embodiment 45 or embodiment 46, wherein the disease or disorder is associated with an elevated level of MECP2.

Embodiment 48. The use of any of embodiments 45-47, wherein the disease or disorder associated with MECP2 is MECP2 duplication syndrome.

Compound No. 1435454

In certain embodiments, Compound No. 1435454 is characterized as a 5-10-5 MOE gapmer of linked nucleosides having a nucleobase sequence (from 5' to 3') of GCAACAT-TTTCAGTTTCAGC (SEQ ID NO: 18), wherein each of nucleosides 1-5 and 16-20 (from 5' to 3') are 2'-MOE nucleosides and each of nucleosides 6-15 are 2'-β-D-deoxy-nucleosides, wherein the internucleoside linkages between nucleosides 2-3, 3-4, 4-5, 5-6, 16-17, and 17-18 are phosphodiester internucleoside linkages, the internucleoside linkages between nucleosides 1-2, 6-7, 7-8, 8-9, 9-10, 10-11, 11-12, 12-13, 13-14, 14-15, 15-16, 18-19, and 19-20 are phosphorothioate internucleoside linkages, and wherein each cytosine is a 5-methylcytosine.

In certain embodiments, Compound No. 1435454 is represented by the following chemical notation:

(SEQ ID NO: 19)
$G_{es}{}^mC_{eo}A_{eo}A_{eo}{}^mC_{eo}A_{ds}T_{ds}T_{ds}T_{ds}T_{ds}{}^mC_{ds}A_{ds}G_{ds}T_{ds}T_{ds}T_{eo}{}^mC_{eo}A_{es}G_{es}{}^mC_e,$ wherein
 A=an adenine nucleobase,
 $^m$C=a 5-methylcytosine nucleobase,
 G=a guanine nucleobase,
 T=a thymine nucleobase,
 e=a 2'-MOE sugar moiety,
 d=a 2'-β-D-deoxyribosyl sugar moiety
 s=a phosphorothioate internucleoside linkage, and
 o=a phosphodiester internucleoside linkage.

In certain embodiments Compound No. 1435454 is represented by the following chemical structure:

Structure 1. Compound 143454.

(SEQ ID NO: 19)

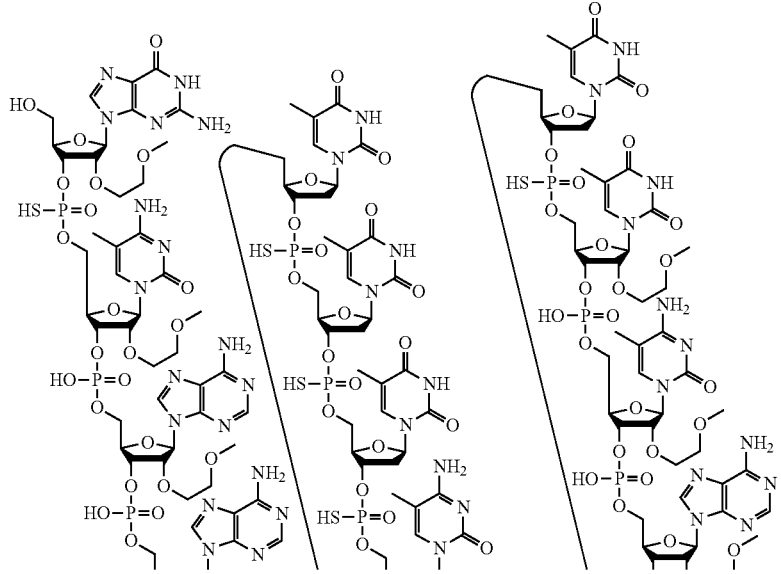

-continued

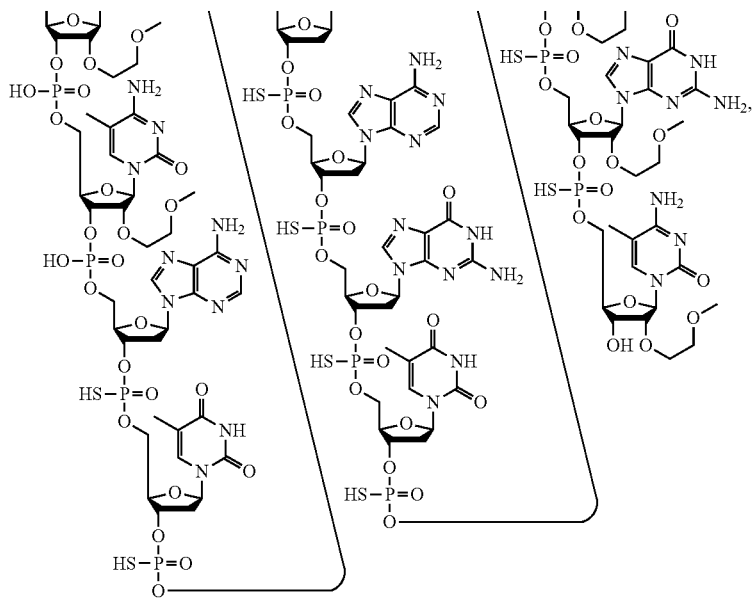

In certain embodiments, the oligomeric compound comprises a pharmaceutically acceptable salt of the modified oligonucleotide represented by Structure 1 comprising one or more cations selected from sodium, potassium, calcium, and magnesium.

In certain embodiments the sodium salt of Compound No. 1435454 is represented by the following chemical structure:

Structure 2. The sodium salt of Compound 143454.

(SEQ ID NO: 19)

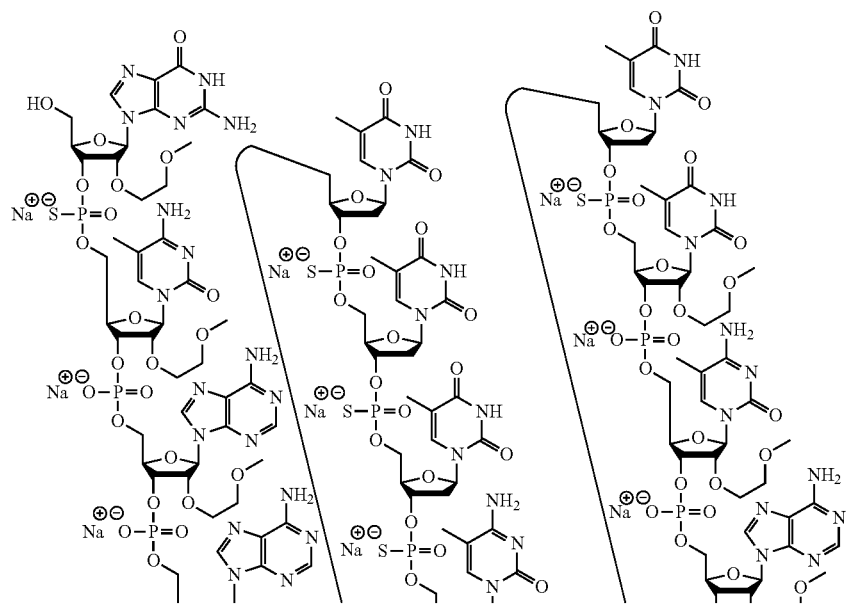

-continued

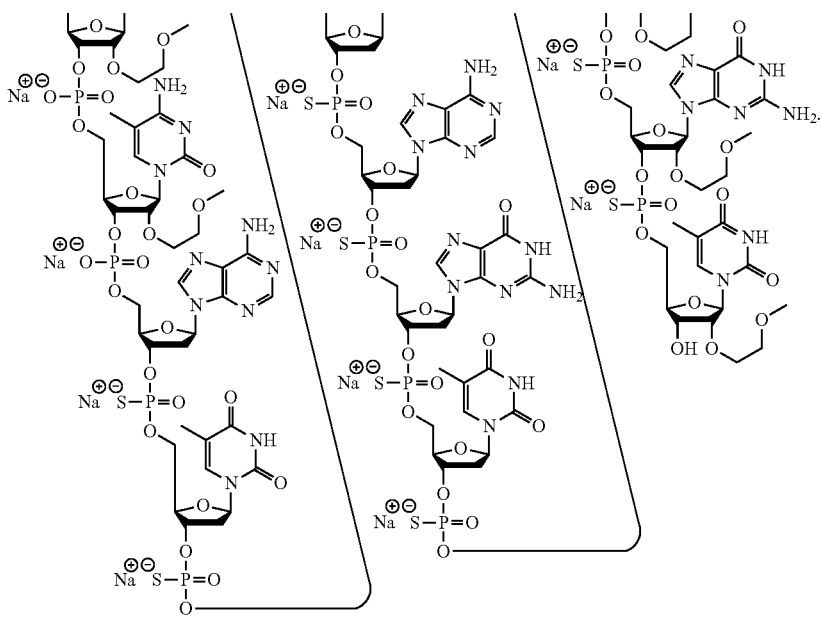

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage. Certain modified nucleosides and modified internucleoside linkages suitable for use in modified oligonucleotides are described below.

A. Certain Modified Nucleosides

Modified nucleosides comprise a modified sugar moiety, a modified nucleobase or both a modified sugar moiety and a modified nucleobase. In certain embodiments, modified nucleosides comprising the following modified sugar moieties and/or the following modified nucleobases may be incorporated into modified oligonucleotides.

1. Certain Sugar Moieties

In certain embodiments, modified sugar moieties are non-bicyclic modified sugar moieties. In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 3', 4', and/or 5' positions.

In certain embodiments, non-bicyclic modified sugar moieties comprise a substituent group at the 2'-position. Examples of substituent groups suitable for the 2'-position of non-bicyclic modified sugar moieties include but are not limited to —F, —OCH$_3$ ("Ome" or "O-methyl"), and —O(CH$_2$)$_2$OCH$_3$ ("MOE" or "O-methoxyethyl"). In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$. In certain embodiments, a 2'-substituted non-bicyclic modified nucleoside comprises a sugar moiety comprising a non-bridging 2'-substituent group of OCH$_2$CH$_2$OCH$_3$.

In certain embodiments, modified furanosyl sugar moieties and nucleosides incorporating such modified furanosyl sugar moieties are further defined by isomeric configuration. For example, a 2'-deoxyfuranosyl sugar moiety may be in seven isomeric configurations other than the naturally occurring β-D-deoxyribosyl configuration. Such modified sugar moieties are described in, e.g., WO 2019/157531. A 2'-modified sugar moiety has an additional stereocenter at the 2'-position relative to a 2'-deoxyfuranosyl sugar moiety; therefore, such sugar moieties have a total of sixteen possible isomeric configurations. 2'-modified sugar moieties described herein are in the β-D-ribosyl isomeric configuration unless otherwise specified.

2. Certain Modified Nucleobases

In certain embodiments, modified oligonucleotides comprise one or more nucleosides comprising an unmodified nucleobase. In certain embodiments, modified oligonucleotides comprise one or more nucleosides comprising a modified nucleobase. Examples of modified nucleobases include 5-methylcytosine. In certain embodiments, modified oligonucleotides comprise one or more nucleosides that does not comprise a nucleobase, referred to as an abasic nucleoside. In certain embodiments, modified oligonucleotides comprise one or more inosine nucleosides (i.e., nucleosides comprising a hypoxanthine nucleobase). An "unmodified nucleobase" is adenine (A), thymine (T), cytosine (C), uracil (U), or guanine (G). A modified nucleobase is a group of atoms other than unmodified A, T, C, U, or G capable of pairing with at least one other nucleobase. A 5-methylcytosine is an example of a modified nucleobase. A universal base is a modified nucleobase that can pair with any one of the five unmodified nucleobases.

In certain embodiments, modified adenine has structure (I):

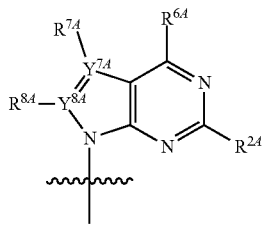

(I)

wherein: $R^{2A}$ is H, $C_1$-$C_6$ alkyl, substituted $C_1$-$C_6$ alkyl, $C_1$-$C_6$ thioalkyl, or substituted $C_1$-$C_6$ thioalkyl, $C_1$-$C_6$ alkyloxy, or substituted $C_1$-$C_6$ alkyloxy; $R^{6A}$ is H, $N(R^a)(R^b)$, oxo, acetyl, formyl, or O-phenyl; $Y^{7A}$ is N and $R^{7A}$ is absent or is $C_1$-$C_6$ alkyl; or $Y^{7A}$ is C and $R^{7A}$ is selected from H, $C_1$-$C_6$ alkyl, or $CN(R^a)(R^b)$; $Y^{8A}$ is N and $R^{8A}$ is absent, or $Y^{8A}$ is C and $R^{8A}$ is selected from H, a halogen, OH, $C_1$-$C_6$ alkyl, or substituted $C_1$-$C_6$ alkyl; $R^a$ and $R^b$ are independently selected from H, $C_1$-$C_6$ alkyl, substituted $C_1$-$C_6$ alkyl, $C_1$-$C_6$ alkenyl, substituted $C_1$-$C_6$ alkenyl, acetyl, formyl, or together form a 5-7-membered heterocycle; excluding where $Y^{7A}$ is N; $Y^{8A}$ is C, $R^{8A}$ is H, $R^{2A}$ is H, and $R^{6A}$ is $NH_2$ (unmodified adenine).

In certain embodiments, modified guanine has structure (II):

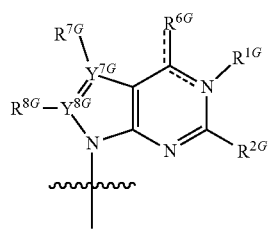

II wherein: $R^{2G}$ is $N(R^a)(R^b)$; $R^{6G}$ is oxo and $R^{1G}$ is H, or $R^{6G}$ is selected from O—$C_1$-$C_6$ alkyl or S—$C_1$-$C_6$ alkyl and $R^{1G}$ is absent; $Y^{7G}$ is N and $R^{7A}$ is absent or is $C_1$-$C_6$ alkyl; or $Y^{7G}$ is C and $R^{7G}$ is selected from H, $C_1$-$C_6$ alkyl, or $CN(R^a)(R^b)$; $Y^{8G}$ is N and $R^{8G}$ is absent, or $Y^{8G}$ is C and $R^{8G}$ is selected from H, a halogen, OH, $C_1$-$C_6$ alkyl, or substituted $C_1$-$C_6$ alkyl; $R^a$ and $R^b$ are independently selected from H, $C_1$-$C_6$ alkyl, substituted $C_1$-$C_6$ alkyl, $C_1$-$C_6$ alkenyl, substituted $C_1$-$C_6$ alkenyl, acetyl, formyl, or together form a 5-7-membered heterocycle; excluding where $Y^{7G}$ is N; $Y^{8G}$ is C, $R^{8G}$ is H, $R^{2G}$ is $NH_2$, and $R^{6G}$ is =O (unmodified guanosine).

In certain embodiments, modified thymine or modified uracil has structure (III):

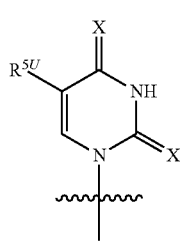

III wherein: X is selected from O or S and $R^{5U}$ is selected from H, OH, halogen, O—$C_1$-$C_{12}$ alkyl, O—$C_1$-$C_{12}$ substituted alkyl, $C_1$-$C_{12}$ alkyl, substituted $C_1$-$C_{12}$ alkyl, $C_1$-$C_{12}$ alkenyl, substituted $C_1$-$C_{12}$ alkenyl; wherein if each X is O, $R^{5U}$ is not H or $CH_3$ (unmodified uracil and unmodified thymine, respectively).

In certain embodiments, modified cytosine has structure (IV):

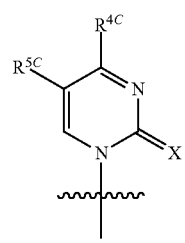

IV wherein: X is selected from O or S, $R^{4C}$ is $N(R^a)(R^b)$; $R^{5C}$ is selected from H, OH, halogen, O—$C_1$-$C_{12}$ alkyl, O—$C_1$-$C_{12}$ substituted alkyl, $C_1$-$C_{12}$ alkyl, substituted $C_1$-$C_{12}$ alkyl, $C_1$-$C_{12}$ alkenyl, substituted $C_1$-$C_{12}$ alkenyl; $R^a$ and $R^b$ are independently selected from H, $C_1$-$C_6$ alkyl, substituted $C_1$-$C_6$ alkyl, $C_1$-$C_6$ alkenyl, substituted $C_1$-$C_6$ alkenyl, acetyl, formyl, or together form a 5-7-membered heterocycle; excluding where X is O, $R^{4C}$ is $NH_2$ and $R^{5C}$ is H (unmodified cytosine).

In certain embodiments, modified nucleobases of a modified oligonucleotide are selected from: 5-substituted pyrimidines, 6-azapyrimidines, alkyl or alkynyl substituted pyrimidines, alkyl substituted purines, and N-2, N-6, and O-6 substituted purines. In certain embodiments, modified nucleobases are selected from: 5-methylcytosine, hypoxanthine, 1-methylpseudouridine, 2-aminopropyladenine, 5-hydroxymethyl cytosine, xanthine, 2-aminoadenine, 6-N-methylguanine, 6-N-methyladenine, 2-propyladenine, 2-thiouracil, 2-thiothymine and 2-thiocytosine, 5-propynyl (C☐C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo (particularly 5-bromo), 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp) Modified nucleobases may also include those in which the purine or pyrimidine base is replaced with other heterocycles, for example, 7-deaza-adenine, 7-deazaguanosine, 2-aminopyridine, and 2-pyridone. Further nucleobases include those disclosed in Englisch, U. et al., Angew. Chem. Int. Ed. 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include, without limitation, Manoharan et al., US 2003/0158403; Manoharan et al., US 2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, each nucleobase of a modified oligonucleotide is selected from unmodified A, unmodified G, unmodified C, unmodified T, unmodified U, $^mC$, or hypoxanthine.

3. Certain Modified Internucleoside Linkages

The naturally occurring internucleoside linkage of RNA and DNA is a 3' to 5' phosphodiester linkage. In certain embodiments, nucleosides of modified oligonucleotides may be linked together using one or more modified internucleoside linkages. The two main classes of internucleoside linking groups are defined by the presence or absence of a phosphorus atom. Representative phosphorus-containing internucleoside linkages include, but are not limited to, phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

-continued

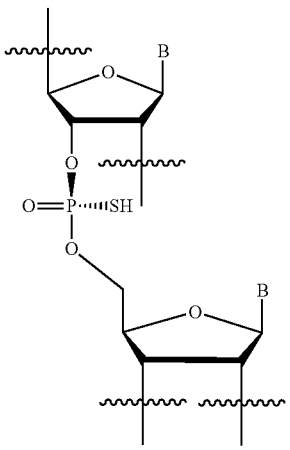

$(S_p)$

Unless otherwise indicated, chiral internucleoside linkages of modified oligonucleotides described herein can be stereorandom or in a particular stereochemical configuration.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. Unless otherwise indicated, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise a deoxy region. In certain embodiments, each nucleoside of the deoxy region is a 2'-β-D-deoxynucleoside. In certain embodiments, the deoxy region consists of 5-12 linked nucleosides. In certain embodiments, the deoxy region consists of 6, 7, 8, 9, 10, or 6-10 linked nucleosides. In certain embodiments, at least one nucleoside within the deoxy region comprises a modified sugar moiety. In certain embodiments, exactly one nucleoside within the deoxy region comprises a modified sugar moiety. In certain embodiments, two or three nucleosides within the deoxy region comprise a modified sugar moiety.

In certain embodiments, the deoxy region is flanked on the 5'-side by a 5'-region consisting of linked 5'-region nucleosides and on the 3'-side by a 3'-region consisting of linked 3'-region nucleosides; wherein the 3'-most nucleoside of the 5'-region is a modified nucleoside and the 5'-most nucleoside of the 3'-region is a modified nucleoside. At least one nucleoside of the 5'-region comprises a modified sugar moiety; and at least one nucleoside of the 3'-region comprises a modified sugar moiety. The three regions (the 5'-region, the deoxy region, and the 3'-region) form a contiguous sequence of nucleosides. In certain embodiments, the sugar moiety of the 3'-most nucleoside of the 5'-region and the sugar moiety of the 5'-most nucleoside of the 3'-region each differ from the sugar moiety of the respective adjacent nucleoside of the deoxy region, thus defining the boundary between the 5'-region, the deoxy region, and the 3'-region. In certain embodiments, each nucleoside of the 5'-region and each nucleoside of the 3'-region comprises a modified sugar moiety. In certain embodiments, the nucleosides within the 5'-region comprise the same sugar modification. In certain embodiments, the nucleosides within the 5'-region comprise two or more different sugar modifications. In certain embodiments, the nucleosides within the 3'-region comprise the same sugar modification. In certain embodiments, the nucleosides within the 3'-region comprise two or more different sugar modifications.

In certain embodiments, the 5'-region and the 3'-region of a modified oligonucleotide each comprises 1-8 nucleosides. In certain embodiments, the 5'-region comprises 1-7 nucleosides. In certain embodiments, the 5'-region comprises 1-6 nucleosides. In certain embodiments, the 5'-region comprises 1, 2, 3, 4, 5, 6, 7, or 8 nucleosides. In certain embodiments, the 3'-region comprises 1-7 nucleosides. In certain embodiments, the 3'-region comprises 1-6 nucleosides. In certain embodiments, the 3'-region comprises 1, 2, 3, 4, 5, 6, 7, or 8 nucleosides.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, each nucleoside of the gap comprises a 2'-β-D-deoxyribosyl sugar moiety. In certain embodiments, each nucleoside of each wing of a gapmer comprises a modified sugar moiety. In certain embodiments, at least one nucleoside of the gap of a gapmer comprises a modified sugar moiety. In certain embodiments, one nucleoside of the gap comprises a modified sugar moiety and each remaining nucleoside of the gap comprises a 2'-deoxyribosyl sugar moiety. In certain embodiments, at least one nucleoside of the gap of a gapmer comprises a 2'-Ome sugar moiety.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification in each sugar moiety of each wing and the gap nucleosides comprise 2'-β-D-deoxyribosyl sugar moieties. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 5-8-5 MOE gapmer consists of 5 linked 2'-MOE nucleosides in the 5'-wing, 8 linked 2'-β-D-deoxynucleosides in the gap, and 5 linked 2'-MOE nucleosides in the 3'-wing.

In certain embodiments, modified oligonucleotides are 5-10-5 MOE gapmers.

In certain embodiments, modified oligonucleotides have the sugar motif from 5' to 3': eeeeedddddddddeeeee; wherein each "d" represents a 2'-β-D-deoxyribosyl sugar moiety and each "e" represents a 2'-MOE ribosyl sugar moiety.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each cytosine is modified. In certain embodiments, some or all of the cytosine nucleobases in a modified oligonucleotide are 5-methylcytosines. In certain embodiments, all of the cytosine nucleobases are 5-methylcytosines and all of the other nucleobases of the modified oligonucleotide are unmodified nucleobases.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl sugar moiety.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate.

In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, populations of modified oligonucleotides are enriched for modified oligonucleotides comprising such internucleoside linkage motifs.

In certain embodiments, modified oligonucleotides have an internucleoside linkage motif of (from 5'-3') sooooossssssssssooss, wherein each "s" represents a phosphorothioate internucleoside linkage and each "o" represents a phosphodiester internucleoside linkage.

C. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

D. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance.

In certain embodiments, conjugation of one or more carbohydrate moieties to a modified oligonucleotide can alter one or more properties of the modified oligonucleotide. In certain embodiments, the carbohydrate moiety is attached to a modified subunit of the modified oligonucleotide. For example, the ribose sugar of one or more ribonucleotide subunits of a modified oligonucleotide can be replaced with another moiety, e.g. a non-carbohydrate (preferably cyclic) carrier to which is attached a carbohydrate ligand A ribonucleotide subunit in which the ribose sugar of the subunit has been so replaced is referred to herein as a ribose replacement modification subunit (RRMS), which is a modified sugar moiety. A cyclic carrier may be a carbocyclic ring system, i.e., one or more ring atoms may be a heteroatom, e.g., nitrogen, oxygen, sulphur. The cyclic carrier may be a monocyclic ring system, or may contain two or more rings, e.g., fused rings. The cyclic carrier may be a fully saturated ring system, or it may contain one or more double bonds. In certain embodiments, the modified oligonucleotide is a gapmer.

In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

In certain embodiments, conjugate groups may be selected from any of a C22 alkyl, C20 alkyl, C16 alkyl, C10 alkyl, C21 alkyl, C19 alkyl, C18 alkyl, C17 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl, C20 alkenyl, C16 alkenyl, C10 alkenyl, C21 alkenyl, C19 alkenyl, C18 alkenyl, C17 alkenyl, C15 alkenyl, C14 alkenyl, C13 alkenyl, C12 alkenyl, C11 alkenyl, C9 alkenyl, C8 alkenyl, C7 alkenyl, C6 alkenyl, or C5 alkenyl.

In certain embodiments, conjugate groups may be selected from any of C22 alkyl, C20 alkyl, C16 alkyl, C10 alkyl, C21 alkyl, C19 alkyl, C18 alkyl, C17 alkyl, C15 alkyl, C14 alkyl, C13 alkyl, C12 alkyl, C11 alkyl, C9 alkyl, C8 alkyl, C7 alkyl, C6 alkyl, and C5 alkyl, where the alkyl chain has one or more unsaturated bonds.

In certain embodiments, a conjugate group has the following structure:

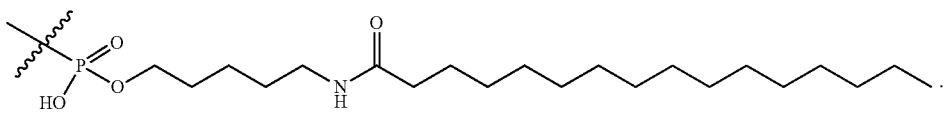 [SMILES: *P(=O)(O)OCCCCCNC(=O)CCCCCCCCCCCCCCC]

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises pyrrolidine.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 1-5 linker-nucleosides. In certain embodiments, conjugate linkers comprise 1-3 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from an amide, an ester, an ether, one or both esters of a phosphodiester, a phosphate ester, a carbamate, and a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

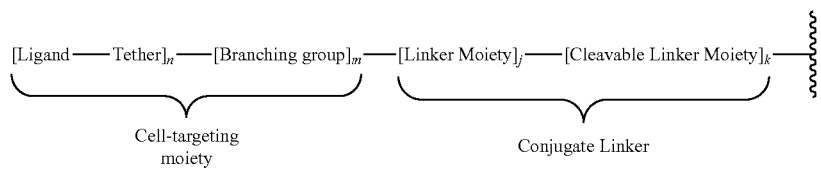

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety targets neurons. In certain embodiments, the cell-targeting moiety targets a neurotransmitter receptor. In certain embodiments, the cell targeting moiety targets a neurotransmitter transporter. In certain embodiments, the cell targeting moiety targets a GABA transporter. See e.g., WO 2011/131693, WO 2014/064257.

In certain embodiments, conjugate groups comprise cell-targeting moieties that have affinities for transferrin receptor (TfR) (also referred to herein as TfR1 and CD71). In certain embodiments, a conjugate group described herein comprises an anti-TfR1 antibody or fragment thereof. In certain embodiments, the conjugate group comprises a protein or peptide capable of binding TfR1. In certain embodiments, the conjugate group comprises an aptamer capable of binding TfR1. In certain embodiments, the anti-TfR1 antibody or fragment thereof can be any known in the art including but not limited to those described in WO 1991/004753; WO2013/103800; WO 2014/144060; WO 2016/081643; WO 2016/179257; WO 2016/207240; WO 2017/221883; WO 2018/129384; WO 2018/124121; WO 2019/151539; WO 2020/132584; WO 2020/028864; U.S. Pat. Nos. 7,208,174; 9,034,329; and 10,550,188. In certain embodiments, a fragment of an anti-TfR1 antibody is F(ab')$_2$, Fab, Fab', Fv, or scFv.

In certain embodiments, the conjugate group comprises a protein or peptide capable of binding TfR1. In certain embodiments, the protein or peptide capable of binding TfR1 can be any known in the art including but not limited to those described in WO 2019/140050; WO 2020/037150; WO 2020/124032; and U.S. Pat. No. 10,138,483.

In certain embodiments, the conjugate group comprises an aptamer capable of binding TfR1. In certain embodiments, the aptamer capable of binding TfR1 can be any known in the art including but not limited to those described in WO 2013/163303; WO 2019/033051; and WO 2020/245198.

B. Certain Terminal Groups

In certain embodiments, oligomeric compounds comprise one or more terminal groups. Examples of terminal groups include but are not limited to conjugate groups, capping groups, phosphate moieties, protecting groups, modified or unmodified nucleosides, and two or more nucleosides that are independently modified or unmodified. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic sugar moieties and/or inverted nucleosides. In certain embodiments, terminal groups comprise one or more 2'-linked nucleosides or sugar moieties. In certain such embodiments, the 2'-linked group is an abasic sugar moiety.

III. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense agents. In certain embodiments, antisense agents have antisense activity when they reduce or inhibit the amount or activity of a target nucleic acid by 25% or more in the standard cell assay. In certain embodiments, antisense agents selectively affect one or more target nucleic acid. Such antisense agents comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense agents or a portion of an antisense agent to a target nucleic acid results in recruitment of a protein that cleaves the target nucleic acid. For example, certain antisense agents result in Rnase H mediated cleavage of the target nucleic acid. Rnase H is a cellular endonuclease that cleaves the RNA strand of an RNA:DNA duplex. The DNA in such an RNA:DNA duplex need not be unmodified DNA. In certain embodiments, described herein are antisense agents comprising antisense oligomeric compounds comprising antisense oligonucleotides that are sufficiently "DNA-like" to elicit Rnase H activity. In certain embodiments, one or more non-DNA-like nucleoside in the gap of a gapmer is tolerated.

In certain antisense activities, an antisense agent or a portion of an antisense agent is loaded into an RNA-induced silencing complex (RISC), ultimately resulting in cleavage of the target nucleic acid. For example, certain antisense agents result in cleavage of the target nucleic acid by Argonaute. Antisense agents that are loaded into RISC are RNAi agents. RNAi agents may be double-stranded (siRNA or dsRNAi) or single-stranded (ssRNAi).

In certain embodiments, hybridization of an antisense agent or portion thereof to a target nucleic acid does not result in recruitment of a protein that cleaves that target nucleic acid. In certain embodiments, hybridization of the antisense agent or portion thereof to the target nucleic acid results in alteration of splicing of the target nucleic acid. In certain embodiments, hybridization of an antisense agent or a portion thereof to a target nucleic acid results in inhibition of a binding interaction between the target nucleic acid and a protein or other nucleic acid. In certain embodiments, hybridization of an antisense agent or a portion thereof to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

IV. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

A. MECP2

In certain embodiments, oligomeric compounds, oligomeric duplexes, or antisense agents comprise or consist of an oligonucleotide comprising a region that is complementary to a target nucleic acid, wherein the target nucleic acid is a MECP2 nucleic acid. In certain embodiments, the MECP2 nucleic acid has the nucleobase sequence set forth in SEQ ID NO: 1 (GenBank Accession No. NC_000023.11 truncated from nucleosides 154019001 to 154101000) or SEQ ID NO: 2 (GenBank Accession No. NM_004992.3). In certain embodiments, contacting a cell with an oligomeric compound, oligomeric duplex, or antisense agent complementary to SEQ ID NO: 1 or SEQ ID NO: 2 reduces the amount of MECP2 RNA, and in certain embodiments reduces the amount of MECP2 protein. In certain embodiments, the oligomeric compound, oligomeric duplex, or antisense agent consists of a modified oligonucleotide. In certain embodiments, the oligomeric compound, oligomeric duplex, or antisense agent consists of a modified oligonucleotide and a conjugate group.

In certain embodiments, contacting a cell with an oligomeric compound, oligomeric duplex, or antisense agent complementary to SEQ ID NO: 1 or SEQ ID NO: 2 reduces the amount of MECP2 RNA in a cell. In certain embodiments, contacting a cell with an oligomeric agent, oligomeric compound, oligomeric duplex, or antisense agent complementary to SEQ ID NO: 1 or SEQ ID NO: 2 reduces the amount of MECP2 protein in a cell. In certain embodiments, the cell is in vitro. In certain embodiments, contacting a cell in a subject with an oligomeric compound, oligomeric duplex, or antisense agent complementary to SEQ ID NO: 1 or SEQ ID NO: 2 ameliorates one or more symptoms or hallmarks of a neurodegenerative disease or disorder associated with MECP2. In certain embodiments, the neurodegenerative disease or disorder associated with MECP2 is MECP duplication syndrome. In certain embodiments, the symptom or hallmark is any of autism, intellectual disability, motor dysfunction, hypotonia, global developmental delays, gastrointestinal symptoms, anxiety, epilepsy, recurrent respiratory tract infections, epileptic encephalopathy, and early death.

In certain embodiments, an oligomeric compound, oligomeric duplex, or antisense agent complementary to SEQ ID NO: 1 or SEQ ID NO: 2 is capable of reducing the detectable amount of MECP2 RNA in vitro by at least 10%, at least 20%, at least 30%, at least 40%, at least 50%, at least 60%, at least 70%, at least 80%, or at least 90% in the standard cell assay. In certain embodiments, an oligomeric compound, oligomeric duplex, or antisense agent complementary to SEQ ID NO: 1 or SEQ ID NO: 2 is capable of reducing the detectable amount of MECP2 protein in vitro by at least 10%, at least 20%, at least 30%, at least 40%, at least 50%, at least 60%, at least 70%, at least 80%, or at least 90%. In certain embodiments, an oligomeric compound, oligomeric duplex, or antisense agent complementary to SEQ ID NO: 1 or SEQ ID NO: 2 is capable of reducing the detectable amount of MECP2 RNA in vivo by at least 10%, at least 20%, at least 30%, at least 40%, at least 50%, at least 60%, at least 70%, at least 80%, or at least 90%. In certain embodiments, an oligomeric compound, oligomeric duplex, or antisense agent complementary to SEQ ID NO: 1 or SEQ ID NO: 2 is capable of reducing the detectable amount of MECP2 protein in vivo by at least 10%, at least 20%, at least 30%, at least 40%, at least 50%, at least 60%, at least 70%, at least 80%, or at least 90%. In certain embodiments, an oligomeric compound, oligomeric duplex, or antisense agent complementary to SEQ ID NO: 1 or SEQ ID NO: 2, is capable of reducing the detectable amount of MECP2 RNA in the CSF of an animal by at least 10%, at least 20%, at least 30%, at least 40%, at least 50%, at least 60%, at least 70%, at least 80%, or at least 90%. In certain embodiments, an oligomeric compound, oligomeric duplex, or antisense agent complementary to SEQ ID NO: 1 or SEQ ID NO: 2, is capable of reducing the detectable amount of MECP2 protein in the CSF of an animal by at least 10%, at least 20%, at least 30%, at least 40%, at least 50%, at least 60%, at least 70%, at least 80%, or at least 90%.

B. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the brain and spinal cord. In certain embodiments, the target nucleic acid is expressed in a pharmacologically relevant cell. In certain embodiments the pharmacologically relevant cell is a MECP2-expressing cell. In certain embodiments the pharmacologically relevant cell is a neuron or glial cell. In certain embodiments, the pharmacologically relevant cell is a neuronal cell. In certain embodiments, the pharmacologically relevant cell is an astrocyte, an oligodendrocyte or a microglial cell.

IV. Certain Methods and Uses

Certain embodiments provided herein relate to methods of reducing or inhibiting MECP2 expression or activity, which can be useful for treating, preventing, or ameliorating a disease or disorder associated with overexpression of MECP2 in a subject, by administration of an oligomeric compound, an oligomeric duplex, or an antisense agent, any of which comprise a modified oligonucleotide having a nucleobase sequence complementary to a MECP2 nucleic acid. In certain embodiments, the disease or disorder associated with overexpression of MECP2 is a neurodegenerative disease or disorder. In certain embodiments, the neurodegenerative disease or disorder is MECP2 Duplication Syndrome.

In certain embodiments, a method comprises administering to a subject an oligomeric compound, an oligomeric duplex, or an antisense agent, any of which having a nucleobase sequence complementary to a MECP2 nucleic acid. In certain embodiments, the subject has or is at risk for developing MECP2 Duplication Syndrome.

In certain embodiments, a method of treating a neurodegenerative disease or disorder associated with MECP2 comprises administering to a subject a therapeutically effective amount of an oligomeric compound, an oligomeric duplex, or an antisense agent, any of which having a nucleobase sequence complementary to an MECP2 nucleic acid, thereby treating the subject. In certain embodiments, the subject has or is at risk for developing a neurodegenerative disease or disorder associated with MECP2. In certain embodiments, the disease or disorder is associated with an elevated level of MECP2 in the subject.

In certain embodiments, the subject has or is at risk for developing MECP2 Duplication Syndrome. In certain embodiments, at least one symptom or hallmark of the neurodegenerative disease or disorder associated with MECP2 Duplication Syndrome is ameliorated. Exemplary symptoms or hallmarks include, but are not limited to, autism, intellectual disability, motor dysfunction, hypotonia, global developmental delays, gastrointestinal symptoms, anxiety, epilepsy, recurrent respiratory tract infections, epileptic encephalopathy, and early death.

In certain embodiments, a method of reducing expression of MECP2 nucleic acid, for example RNA, or reducing the expression of MECP2 protein in a cell comprises administering to the subject an oligomeric compound, an oligomeric duplex, or an antisense agent, any of which having a nucleobase sequence complementary to an MECP2 nucleic acid, thereby inhibiting expression of MECP2 nucleic acid in the subject. In certain embodiments, administering the oligomeric compound, the oligomeric duplex, or the antisense agent inhibits expression of MECP2 in the brain or the spinal cord of the subject. In certain embodiments, the subject has or is at risk for developing a neurological disease or condition associated with MECP2. In certain embodiments, the subject has or is at risk for developing MECP2 Duplication Syndrome.

In certain embodiments, a method of inhibiting expression of MECP2 nucleic acid in a cell comprises contacting the cell with an oligomeric compound, an oligomeric duplex, or an antisense agent, any of which having a nucleobase sequence complementary to a MECP2 nucleic acid, thereby inhibiting expression of MECP2 nucleic acid in the cell. In certain embodiments, the cell is a human cell. In certain embodiments, the cell is a brain cell. In certain embodiments, the cell is a neuron or a glial cell (e.g., an astrocyte, an oligodendrocyte, a microglial cell). In certain embodiments, the cell is obtained from a subject, e.g., a subject that has or is at risk for developing a disease or disorder associated with MECP2. In certain embodiments, the cell is in a subject having a disease or condition associated with MECP2 such as MECP2 Duplication Syndrome.

In certain embodiments, a method of reducing expression of MECP2, for example MECP2 RNA, or reducing the expression of MECP2 protein in a cell comprises contacting the cell with an oligomeric compound, an oligomeric duplex, or an antisense agent, any of which having a nucleobase sequence complementary to an ATN1 nucleic acid. In certain embodiments, the subject has or is at risk for developing MECP2 Duplication Syndrome (MDS). In certain embodiments, the subject has MDS. In certain embodiments, the cell is a neuron or glial cell. In certain embodiments, the cell is a human cell.

Certain embodiments are drawn to an oligomeric compound, an oligomeric duplex, or an antisense agent, any of which having a nucleobase sequence complementary to an MECP2 nucleic acid, for use in treating a disease or disorder associated with elevated MECP2 signaling, or with overexpression of MECP2. In certain embodiments, the disease or disorder is MECP2 Duplication Syndrome. In certain embodiments, an an oligomeric compound, an oligomeric duplex, or an antisense agent is for use in improving a symptom or hallmark of a disease or condition associated with MECP2 Duplication Syndrome. In certain embodiments, the symptom or hallmark is selected from autism, intellectual disability, motor dysfunction, hypotonia, global developmental delays, gastrointestinal symptoms, anxiety, epilepsy, recurrent respiratory tract infections, epileptic encephalopathy, and early death. In certain embodiments, an oligomeric compound, a modified oligonucleotide, an oligomeric duplex, or an antisense agent is for use in reducing MECP2 expression in a subject.

Certain embodiments are drawn to an oligomeric compound, an oligomeric duplex, or an antisense agent, any of which comprising a modified oligonucleotide having a nucleobase sequence complementary to an MECP2 nucleic acid, for the manufacture or preparation of a medicament for treating a disease associated with MECP2. In certain embodiments, the disease is MECP2 Duplication Syndrome. In certain embodiments an oligomeric compound, an oligomeric duplex, or an antisense agent is for the manufacture or preparation of a medicament for improving symptoms or hallmarks associated with MECP2 Duplication Syndrome. In certain embodiments, the symptom or hallmark is selected from autism, intellectual disability, motor dysfunction, hypotonia, global developmental delays, gastrointestinal symptoms, anxiety, epilepsy, recurrent respiratory tract infections, epileptic encephalopathy, and early death. In certain embodiments, an oligomeric compound, an oligomeric duplex, or an antisense agent is for the manufacture or preparation of a medicament for use in reducing MECP2 expression in a subject.

In any of the methods or uses described herein, the oligomeric compound, oligomeric duplex, or antisense agent can be any described herein.

V. Certain Pharmaceutical Compositions

In certain embodiments, described herein are pharmaceutical compositions comprising one or more oligomeric compounds. In certain embodiments, the one or more oligomeric compounds each comprise a modified oligonucleotide. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compounds and phosphate-buffered saline (PBS). In certain embodiments, the sterile PBS is pharmaceutical grade PBS. In certain embodiments, a pharmaceutical composition comprises or consists of one or more oligomeric compounds and artificial cerebrospinal fluid ("artificial CSF" or "aCSF"). In certain embodiments, the artificial cerebrospinal fluid is pharmaceutical grade artificial cerebrospinal fluid.

In certain embodiments, a pharmaceutical composition comprises an oligomeric compound and PBS. In certain embodiments, a pharmaceutical composition consists of an oligomeric compound and PBS. In certain embodiments, a pharmaceutical composition consists essentially of an oligomeric compound and PBS. In certain embodiments, the PBS is pharmaceutical grade.

In certain embodiments, a pharmaceutical composition comprises a modified oligonucleotide and PBS. In certain embodiments, a pharmaceutical composition consists of a modified oligonucleotide and PBS. In certain embodiments, a pharmaceutical composition consists essentially of a modified oligonucleotide and PBS. In certain embodiments, the PBS is pharmaceutical grade.

In certain embodiments, a pharmaceutical composition comprises an oligomeric compound and artificial cerebrospinal fluid. In certain embodiments, a pharmaceutical composition consists of an oligomeric compound and artificial cerebrospinal fluid. In certain embodiments, a pharmaceutical composition consists essentially of an oligomeric compound and artificial cerebrospinal fluid. In certain embodiments, the artificial cerebrospinal fluid is pharmaceutical grade.

In certain embodiments, a pharmaceutical composition comprises a modified oligonucleotide and aCSF. In certain embodiments, a pharmaceutical composition consists of a modified oligonucleotide and aCSF. In certain embodiments, a pharmaceutical composition consists essentially of a modified oligonucleotide and aCSF. In certain embodiments, the aCSF is pharmaceutical grade. In certain embodiments, aCSF comprises sodium chloride, potassium chloride, sodium dihydrogen phosphate dihydrate, sodium phosphate dibasic anhydrous, calcium chloride dihydrate, and magnesium chloride hexahydrate. In certain embodiments, the pH of an aCSF solution is modulated with a suitable pH-adjusting agent, for example, with acids such as hydrochloric acid and alkalis such as sodium hydroxide, to a range of from about 7.1-7.3, or to about 7.2.

In certain embodiments, pharmaceutical compositions comprise one or more oligomeric compounds and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound; esters of the the oligomeric compound; or salts of such esters. In certain embodiments, pharmaceutical compositions comprising oligomeric compounds comprising one or more modified oligonucleotide, upon administration to an subject, including a human subject, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. In certain embodiments, pharmaceutically acceptable salts comprise inorganic salts, such as monovalent or divalent inorganic salts. Suitable pharmaceutically acceptable salts include, but are not limited to, sodium, potassium, calcium, and magnesium salts. In certain embodiments, prodrugs comprise one or more conjugate group attached to an oligonucleotide, wherein the conjugate group is cleaved by endogenous nucleases within the body.

In certain embodiments, oligomeric compounds are lyophilized and isolated as sodium salts. In certain embodiments, the sodium salt of an oligomeric compound is mixed with a pharmaceutically acceptable diluent. In certain embodiments, the pharmaceutically acceptable diluent comprises sterile saline, sterile water, PBS, or aCSF. In certain embodiments, the sodium salt of an oligomeric compound is mixed with PBS. In certain embodiments, the sodium salt of an oligomeric compound is mixed with aCSF. In certain embodiments, the sodium salt of the oligomeric compound is a sodium salt of a modified oligonucleotide.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents comprising an oligomeric compound provided herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in an aqueous solution, such as water or a physiologically compatible buffer such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or salt thereof" or "or a pharmaceutically acceptable salt thereof" expressly includes all such forms that may be fully or partially protonated/de-protonated/in association with a cation or a combination of cations. In certain embodiments, one or more specific cation is identified. The cations include, but are not limited to, sodium, potassium, calcium, and magnesium. In certain embodiments, a structure depicting the free acid of a compound followed by the term "or a pharmaceutically acceptable salt thereof" expressly includes all such forms that may be fully or partially protonated/de-protonated/in association with one or more cations selected from sodium, potassium, calcium, and magnesium.

In certain embodiments, modified oligonucleotides or oligomeric compounds are in aqueous solution with sodium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid.

For example, where a modified oligonucleotide or an oligomeric compound is in solution comprising sodium (e.g., saline), the modified oligonucleotide or oligomeric compound may be partially or fully de-protonated and in association with sodium ions. However, the mass of the protons is nevertheless counted toward the weight of the dose, and the mass of the sodium ions is not counted toward the weight of the dose. Thus, for example, a dose, or dosage unit, of 10 mg of Compound No. 1435454 equals the number of fully protonated molecules that weighs 10 mg. This would be equivalent to 10.59 mg of solvent-free, sodium acetate-free, anhydrous sodiated Compound No. 1435454.

In certain embodiments, where a modified oligonucleotide or oligomeric compound is in a solution, such as aCSF, comprising sodium, potassium, calcium, and magnesium, the modified oligonucleotide or oligomeric compound may be partially or fully de-protonated and in association with sodium, potassium, calcium, and/or magnesium. However, the mass of the protons is nevertheless counted toward the weight of the dose, and the mass of the sodium, potassium, calcium, and magnesium ions is not counted toward the weight of the dose.

In certain embodiments, when an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

NONLIMITING DISCLOSURE AND INCORPORATION BY REFERENCE

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Herein, the description of compounds as having "the nucleobase sequence of" a SEQ ID NO describes only the nucleobase sequence. Accordingly, absent additional description, such description of compounds by reference to a nucleobase sequence of a SEQ ID NO does not limit sugar or internucleoside linkage modifications or presence or absence of additional substituents such as a conjugate group. Further, absent additional description, the nucleobases of a compound "having the nucleobase sequence of" a SEQ ID NO include such compounds having modified forms of the identified nucleobases as described herein.

The sequence listing accompanying this filing identifies each sequence as either "RNA" or "DNA" as required; however, one of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar moiety (2'-OH in place of one 2'-H of DNA) or as an RNA having a modified base (thymine (methylated uracil) in place of a uracil of RNA); and certain nucleic acid compounds described herein comprise one or more nucleosides comprising modified sugar moieties having 2'-substituent(s) that are neither OH nor H. One of skill in the art will readily appreciate that labeling such nucleic acid compounds "RNA" or "DNA" does not alter or limit the description of such nucleic acid compounds. Accordingly, nucleic acid sequences provided herein, including, but not limited to those in the sequence listing, are intended to encompass nucleic acids containing any combination of natural or modified RNA and/or DNA, unless otherwise stated, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position. Finally, for clarity, unless otherwise indicated, the phrase "nucleobase sequence of SEQ ID NO: X", refers only to the sequence of nucleobases in that SEQ ID NO.: X, independent of any sugar or internucleoside linkage modifications also described in such SEQ ID.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, all cis- and trans-isomers and tautomeric forms of the compounds herein are also included unless otherwise indicated. Oligomeric compounds described herein include chirally pure or enriched mixtures as well as racemic mixtures. For example, oligomeric compounds having a plurality of phosphorothioate internucleoside linkages include such compounds in which chirality of the phosphorothioate internucleoside linkages is controlled or is random. Unless otherwise indicated, compounds described herein are intended to include corresponding salt forms.

Herein, the description of compounds by chemical notation (subscripts and/or superscripts to indicate chemical modifications) without reference to a specific Compound No. include only each noted modification, but may include additional substituents, such as a conjugate group, unless otherwise indicated. For example, the chemical notation of "$A_{es}T_{ko}{}^mC_{ez}G_{ds}C$" indicates a compound wherein the first nucleoside comprises a 2'-MOE sugar moiety (indicated by the "e" subscript) and an unmodified adenine nucleobase linked to the second nucleoside via a phosphorothioate linkage (indicated by the "s" subscript); the second nucleoside comprises a cEt sugar moiety (indicated by the "k" subscript) and an unmodified thymine nucleobase linked to the third nucleoside via a phosphodiester linkage (indicated by the "o" subscript); the third nucleoside comprises a 2'-MOE sugar moiety and a 5-methyl modified cytosine nucleobase (indicated by the "m" superscript) linked to the fourth nucleoside via a mesylphosphoramidate linkage (indicated by the "z" subscript); the fourth nucleoside comprises a 2'-β-D-deoxyribosyl sugar moiety (indicated by the "d" subscript) and an unmodified guanine nucleobase linked to the fifth nucleoside with a phosphorothioate linkage; and the fifth nucleoside comprises a 2'-β-D-deoxyribosyl sugar moiety and an unmodified cytosine nucleobase; and the compound may include additional substituents, such as a conjugate group.

Herein, where a specific compound (e.g., with reference to a Compound No.) is described (as in the examples) by chemical notation, each nucleobase, sugar, and internucleoside linkage of such specific compound is modified only as indicated. Accordingly, in the context of a description of a specific compound having a particular Compound No., "$A_{es}T_{ko}{}^mC_{ez}G_{ds}C$" indicates a compound wherein the first nucleoside comprises a 2'-MOE sugar moiety (indicated by the "e" subscript) and an unmodified adenine nucleobase linked to the second nucleoside via a phosphorothioate linkage (indicated by the "s" subscript); the second nucleoside comprises a cEt sugar moiety (indicated by the "k" subscript) and an unmodified thymine nucleobase linked to the third nucleoside via a phosphodiester linkage (indicated by the "o" subscript); the third nucleoside comprises a 2'-MOE sugar moiety and a 5-methyl modified cytosine nucleobase (indicated by the "m" superscript) linked to the fourth nucleoside via a mesylphosphoramidate linkage (indicated by the "z" subscript); the fourth nucleoside comprises a 2'-β-D-deoxyribosyl sugar moiety (indicated by the "d" subscript) and an unmodified guanine nucleobase linked to the fifth nucleoside with a phosphorothioate linkage; and the fifth nucleoside comprises a 2'-β-D-deoxyribosyl sugar moiety and an unmodified cytosine nucleobase; and the compound does not include additional substituents.

Herein, sugar, internucleoside linkage, and nucleobase modifications may be indicated within a nucleotide or nucleobase sequence (e.g., by superscript or subscript, as shown above) or may be indicated in text accompanying a sequence (e.g., in separate text that appears within or above or below a table of compounds).

Where a specific compound is described herein by way of a drawn chemical structure, each nucleobase, sugar, and internucleoside linkage of such a specific compound includes only the modifications indicated in the drawn chemical structure. One of skill will appreciate, however, that drawn compounds may exist in equilibrium between tautomeric forms and/or as salts in equilibrium with protonated or ionic forms. Drawn structures are intended to capture all such forms of such compounds.

While effort has been made to accurately describe compounds in the accompanying sequence listing, should there be any discrepancies between a description in this specification and in the accompanying sequence listing, the description in the specification and not in the sequence listing is the accurate description.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of 5-10-5 MOE Gapmers Complementary to Human MECP2 RNA In Vitro, Single Dose Modified oligonucleotides complementary to a human MECP2 nucleic acid were designed and tested for their single dose effects on MECP2 RNA in vitro.

The modified oligonucleotides in the table below are 5-10-5 MOE gapmers with mixed PO/PS linkages. The modified oligonucleotides in the table below are 20 nucleosides in length, wherein the sugar motif for the modified oligonucleotides is (from 5' to 3'): eeeeedddddddddeeeee; wherein each "e" represents a 2'-MOE ribosyl sugar moiety and each "d" represents a 2'-β-D-deoxyribosyl sugar moiety. The internucleoside linkage motif for the modified oligonucleotides is (from 5' to 3'): soooosssssssssooss; wherein each "s" represents a phosphorothioate internucleoside linkage, and each "o" represents a phosphodiester linkage. Each cytosine residue is a 5-methylcytosine.

Modified oligonucleotides listed in the table below are 100% complementary to SEQ ID NO: 1 (the complement of GenBank Accession No. NC_000023.11 truncated from nucleosides 154019001 to 154101000), to SEQ ID NO: 2 (GenBank Accession No. NM_004992.3), or to both "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. 'N/A' indicates that the modified oligonucleotide is not 100% complementary to that particular target nucleic acid sequence.

A431 cells were treated with modified oligonucleotide at a concentration of 4,000 nM by free uptake at a density of 10,000 cells per well. After a treatment period of approximately 48 hours, total RNA was isolated from the cells and MECP2 RNA levels were measured by quantitative real-time RT-PCR. MECP2 RNA levels were measured by human primer-probe set RTS37209 (forward sequence CAAGGCCAAACAGAGAGGA, designated herein as SEQ ID NO: 3; reverse sequence TTGTCAGAGCCCTACCCATA, designated herein as SEQ ID NO: 4; probe sequence AGAATAAAGGCAGCTGTTGTCTCTTCTCC, designated herein as SEQ ID NO: 5). MECP2 RNA levels were normalized to total RNA content, as measured by RIBOGREEN®. Reduction of MECP2 RNA is presented in the table below as percent MECP2 RNA relative to the amount of MECP2 RNA in untreated control cells (% UTC).

TABLE 1

Reduction of MECP2 RNA by 5-10-5 MOE modified oligonucleotides with mixed PO/PS internucleoside linkages in A431 cells

| Compound No. | SEQ ID NO: 1 Start Site | SEQ ID NO: 1 Stop Site | SEQ ID NO: 2 Start Site | SEQ ID NO: 2 Stop Site | Sequence' (5' t' 3') | MECP2 (% UTC) | SEQ ID NO |
|---|---|---|---|---|---|---|---|
| 1435454 | 32611 | 32630 | N/A | N/A | GCAACATTTCAGTTTCAGC | 10 | 18 |

Example 2: Effect of Modified Oligonucleotides on Human MECP2 In Vitro, Multiple Doses Modified oligonucleotides were tested at various doses in A431 cells. A431 cells plated at a density of 10,000 cells per well were treated with modified oligonucleotides at concentrations indicated in the table below by free uptake. After a treatment period of approximately 48 hours, total RNA was isolated from the cells and MECP2 RNA levels were measured by quantitative real-time RTPCR Human MECP2 primer-probe set RTS37209 (described herein above) was used to measure RNA levels as described above. MECP2 RNA levels were normalized to total RNA content, as measured by RIBOGREEN®. Reduction of MECP2 RNA is presented in the table below as percent MECP2 RNA, relative to untreated control cells (% UTC). The half maximal inhibitory concentration (IC$_{50}$) of the modified oligonucleotide was calculated using a linear regression on a log/linear plot of the data in Excel and is also presented in the table below. Each experiment is presented in a separate table.

TABLE 2

Dose-dependent reduction of human MECP2 RNA in A431 cells by modified oligonucleotides

| Compound | MECP2 RNA (% UTC) | | | | IC$_{50}$ |
| --- | --- | --- | --- | --- | --- |
| No. | 63 nM | 250 nM | 1000 nM | 4000 nM | (µM) |
| 1435454 | 26 | 10 | 3 | 1 | <0.063 |

Example 3: Effect of Modified Oligonucleotides on Human MECP2 In Vitro, Multiple Doses Modified oligonucleotides were tested at various doses in SH-SY5Y cells. Compound No. 1435454, described hereinabove, is a modified oligonucleotide having a nucleobase sequence of (from 5' to 3') GCAACATTTTCAGTTTCAGC (SEQ ID NO: 18), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2-3, 3-4, 4-5, 5-6, 16-17, and 17-18 are phosphodiester internucleoside linkages, the internucleoside linkages between nucleosides 1-2, 6-7, 7-8, 8-9, 9-10, 10-11, 11-12, 12-13, 13-14, 14-15, 15-16, 18-19, and 19-20 are phosphorothioate internucleoside linkages, and wherein each cytosine is a 5-methylcytosine.

Comparator Compound No. 628785, previously described in WO 2016/141145; WO 2016/141236; and in Sztainberg et al., Nature 528 (7580): 123-126 (2015) is a 5-10-5 MOE gapmer, having a nucleobase sequence of (from 5' to 3'): GGTTTTTCTCCTTTATTATC (incorporated herein as SEQ ID NO: 20), wherein the sugar motif for Compound No. 628785 is (from 5' to 3'): eeeeedddddddddeeeee; wherein each "e" represents a 2'-MOE ribosyl sugar moiety and each "d" represents a 2'-β-D-deoxyribosyl sugar moiety, wherein the internucleoside linkage motif is (from 5' to 3'): soooosssssssssooss; wherein each "s" represents a phosphorothioate internucleoside linkage, and each "o" represents a phosphodiester linkage, and wherein each cytosine residue is a 5-methylcytosine.

Comparator Compound No. 912669, previously described in Shao et al., Sci. Trans. Med. 13(583) (2021) is a 5-10-5 MOE gapmer, having a nucleobase sequence of (from 5' to 3'): TATGGTTTTTCTCCTTTATT (incorporated herein as SEQ ID NO: 21), wherein the sugar motif for Compound No. 912669 is (from 5' to 3'): eeeeedddddddddeeeee; wherein each "e" represents a 2'-MOE ribosyl sugar moiety and each "d" represents a 2'-β-D-deoxyribosyl sugar moiety, wherein the internucleoside linkage motif is (from 5' to 3'): sooooossssssssssooss, wherein each "s" represents a phosphorothioate internucleoside linkage, and each "o" represents a phosphodiester linkage, and wherein each cytosine residue is a 5-methylcytosine.

The compounds 628785 and 912669 are 100% complementary to SEQ ID NO: 1 (described herein above). In the table below, "start site" indicates the 5'-most nucleoside to which the modified oligonucleotide is complementary in the target nucleic acid sequence and "stop site" indicates the 3'-most nucleoside to which the modified oligonucleotide is complementary in the target nucleic acid sequence. 'N/A' indicates that the modified oligonucleotide is not 100% complementary to that particular target nucleic acid sequence.

TABLE 3

| Compound No. | SEQ ID NO: 1 Start Site | SEQ ID NO: 1 Stop Site | SEQ ID NO: 2 Start Site | SEQ ID NO: 2 Stop Site |
| --- | --- | --- | --- | --- |
| 628785 | 32133 | 32152 | N/A | N/A |
| 912669 | 32136 | 32155 | N/A | N/A |

SHSY5Y cells, plated at a density of 12,500 cells per well, were differentiated in Neurobasal media supplemented with B27 (ThermoFisher), GlutaMAX (ThermoFisher), and 10 µM retinoic acid (Sigma) for 10 days. Differentiated SH-SY5Y cells were treated with modified oligonucleotides at concentrations indicated in the tables below by free uptake. After a treatment period of 5 days, total RNA was isolated from the cells and MECP2 RNA levels were measured by quantitative real-time RTPCR. Human MECP2 primer-probe set RTS52360 (forward sequence GATCAATCCCCAGGGAAAAGC, designated herein as SEQ ID NO: 12; reverse sequence CCTCTCCCAGTTACCGTGAAG, designated herein as SEQ ID NO: 13; probe sequence CATTAGGGTCCAGGGATGTGTCGC, designated herein as SEQ ID NO: 14) was used to measure RNA levels as described above. MECP2 RNA levels were normalized to human GAPDH Human GAPDH was amplified using human primer probe set RTS104 (forward sequence GAAGGTGAAGGTCGGAGTC, designated herein as SEQ ID NO: 15; reverse sequence GAAGATGGTGATGGGATTTC, designated herein as SEQ ID NO: 16; probe sequence CAAGCTTCCCGTTCTCAGCC, designated herein as SEQ ID NO: 17).

Reduction of MECP2 RNA is presented in the table below as percent MECP2 RNA, relative to the amount of MECP2 RNA in untreated control cells (% UTC). The half maximal inhibitory concentration (IC$_{50}$) of each modified oligonucleotide was calculated with GraphPad Prism software.

As shown in the table below, Compound No. 1435454 is more potent than comparator Compound No. 628785 and comparator Compound No. 912669 in this assay.

TABLE 4

Dose-dependent reduction of human MECP2 RNA in SH-SY5Y cells by modified oligonucleotides

| Compound No. | 7.86 nM | 19.7 nM | 49.2 nM | 123 nM | 307 nM | 768 nM | 1,920 nM | 4,800 nM | 12,000 nM | 30,000 nM | IC$_{50}$ (µM) |
|---|---|---|---|---|---|---|---|---|---|---|---|
| 628785 | 84 | 88 | 64 | 56 | 34 | 25 | 12 | 6 | 4 | 2 | 0.145 |
| 912669 | 94 | 110 | 96 | 85 | 71 | 46 | 28 | 16 | 10 | 4 | 0.737 |
| 1435454 | 76 | 66 | 30 | 27 | 15 | 7 | 3 | 1 | 1 | 0 | 0.031 |

Example 4: Activity of Modified Oligonucleotides Complementary to Human MECP2 in Transgenic Mice A MECP2 transgenic line, MECP2$^{Tg1}$, previously described in Collins A L, et. al., Human Molecular Genetics, Volume 13, Issue 21, 1 Nov. 2004, pages 2679-2689, was used to determine the effect of modified oligonucleotides described herein above on MECP2 RNA.

MECP2 transgenic mice were divided into groups of 2-4 mice each. Each mouse received a single ICV bolus injection of either 350 µg or 500 µg of modified oligonucleotide as specified in the tables below. A group of 2-4 mice received a single ICV bolus injection with PBS as a negative control.

Two weeks post treatment, mice were sacrificed and RNA was extracted from cortical brain tissue and spinal cord for quantitative real-time RTPCR analysis of RNA expression of MECP2 using human primer probe set RTS4253 (forward sequence TGAAGGAGTCTTCTATCCGATCTGT, designated herein as SEQ ID NO: 6; reverse sequence CACTTCCTTGACCTCGATGCT, designated herein as SEQ ID NO: 7; probe sequence AGACCGTACTCCCCAT-CAAGAAGCGC, designated herein as SEQ ID NO: 8) or human primer probe set RTS37209 (described herein above). MECP2 RNA levels were normalized to mouse GAPDH. Mouse GAPDH was amplified using primer probe set mGapdh_LTS00102 (forward sequence GGCAAATT-CAACGGCACAGT, designated herein as SEQ ID NO: 9; reverse sequence GGGTCTCGCTCCTGGAAGAT, designated herein as SEQ ID NO: 10; probe sequence AAGGCCGAGAATGGGAAGCTTGTCATC, designated herein as SEQ ID NO: 11). Results are presented as percent human MECP2 RNA relative to the amount of MECP2 RNA in PBS treated animals, (% control). Each experiment is presented in a separate table.

TABLE 5

Reduction of human MECP2 RNA in MECP2 transgenic mice at a dose of 500 µg

| | MECP2 RNA (% control) | |
|---|---|---|
| Compound No. | Spinal Cord RTS4253 | Cortex RTS4253 |
| PBS | 100 | 100 |
| 628785 | 13 | 26 |
| 912669 | 49 | 52 |

TABLE 6

Reduction of human MECP2 RNA in MECP2 transgenic mice at a dose of 500 µg

| | MECP2 RNA (% control) | |
|---|---|---|
| Compound No. | Spinal Cord RTS4253 | Cortex RTS4253 |
| PBS | 100 | 100 |
| 628785 | 35 | 18 |
| 912669 | 57 | 24 |

TABLE 7

Reduction of human MECP2 RNA in MECP2 transgenic mice at a dose of 350 µg

| | MECP2 RNA (% control) | |
|---|---|---|
| Compound No. | Spinal Cord RTS4253 | Cortex RTS4253 |
| PBS | 100 | 100 |
| 1435454 | 27 | 16 |

Example 5: Activity of Modified Oligonucleotides Complementary to Human MECP2 in Transgenic Mice, Multiple Dose The MECP2 transgenic mice (described herein above) were divided into groups of 4 mice each. Each mouse received a single ICV bolus injection of modified oligonucleotide at various concentrations defined in the table below. A group of 4 mice received PBS as a negative control.

Two weeks post treatment, mice were sacrificed, and RNA was extracted from cortical brain tissue, spinal cord, hippocampus, and cerebellum for quantitative real-time RT-PCR analysis to measure the amount of MECP2 RNA using human primer probe set RTS4253 (described herein above). MECP2 RNA levels were normalized to mouse GAPDH. Mouse GAPDH was amplified using primer probe set mGapdh_2 (described herein above). Results are presented as percent human MECP2 RNA relative to the amount of MECP2 RNA in PBS treated animals, (% control).

TABLE 8

Reduction of MECP2 RNA in MECP2 transgenic mice

| Compound No. | Dose (μg) | MECP2 RNA (% control) | | | | | | | |
|---|---|---|---|---|---|---|---|---|---|
| | | Cortex RTS4253 | ED50 (μg) | Hippocampus RTS4253 | ED50 (μg) | Cerebellum RTS4253 | ED50 (μg) | Spinal Cord RTS4253 | ED50 (μg) |
| PBS | — | 100 | — | 100 | — | 100 | — | 100 | — |
| 1435454 | 3 | 96 | 47.22 | 93 | 25.62 | 89 | 57.85 | 96 | 33.09 |
| | 10 | 97 | | 73 | | 93 | | 84 | |
| | 30 | 69 | | 51 | | 74 | | 60 | |
| | 100 | 24 | | 18 | | 52 | | 33 | |
| | 300 | 17 | | 19 | | 52 | | 22 | |
| | 700 | 8 | | 13 | | 31 | | 18 | |

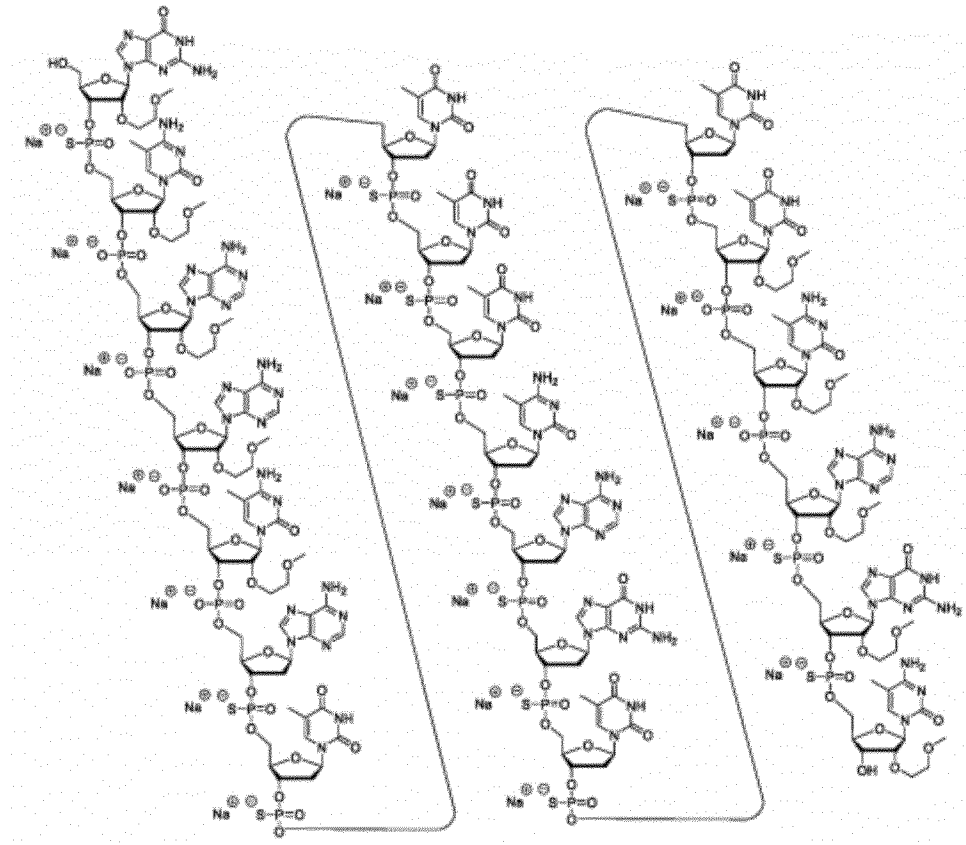

The invention claimed is:

1. A modified oligonucleotide according to the following chemical structure:

(SEQ ID NO: 19)

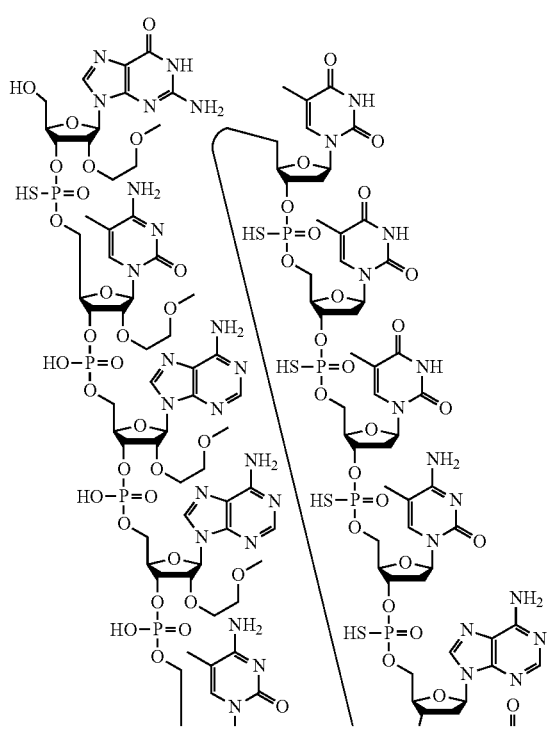

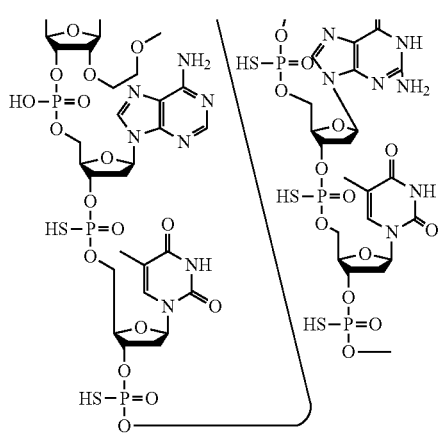

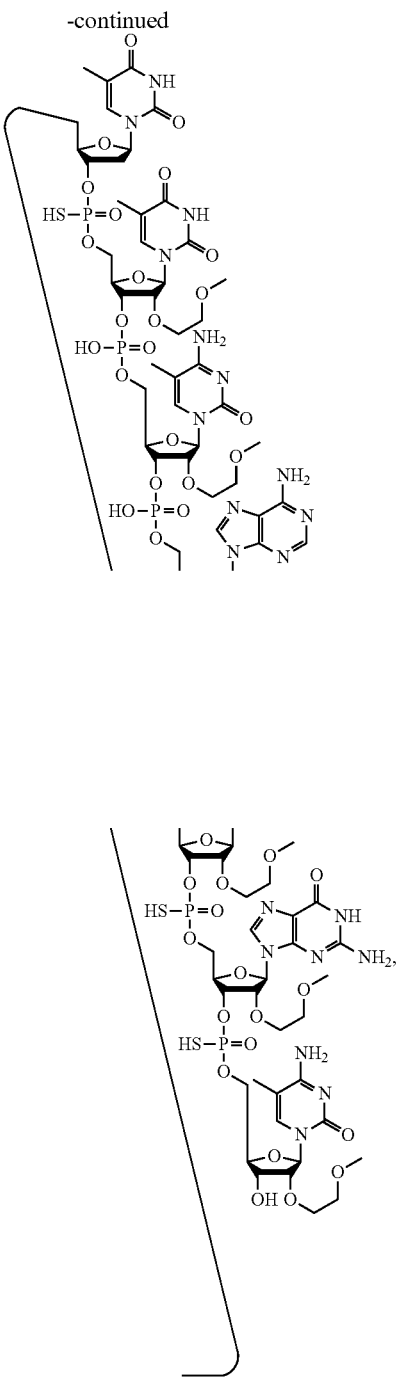

or a pharmaceutically acceptable salt thereof.

2. The modified oligonucleotide of claim 1, wherein the modified oligonucleotide is a pharmaceutically acceptable salt of the chemical structure, wherein the pharmaceutically acceptable salt comprises one or more cations selected from the group consisting of sodium, potassium, calcium, and magnesium.

3. The modified oligonucleotide of claim 2, wherein the pharmaceutically acceptable salt of the chemical structure is the sodium salt or the potassium salt.

4. A modified oligonucleotide according to the following chemical structure:

(SEQ ID NO: 19)

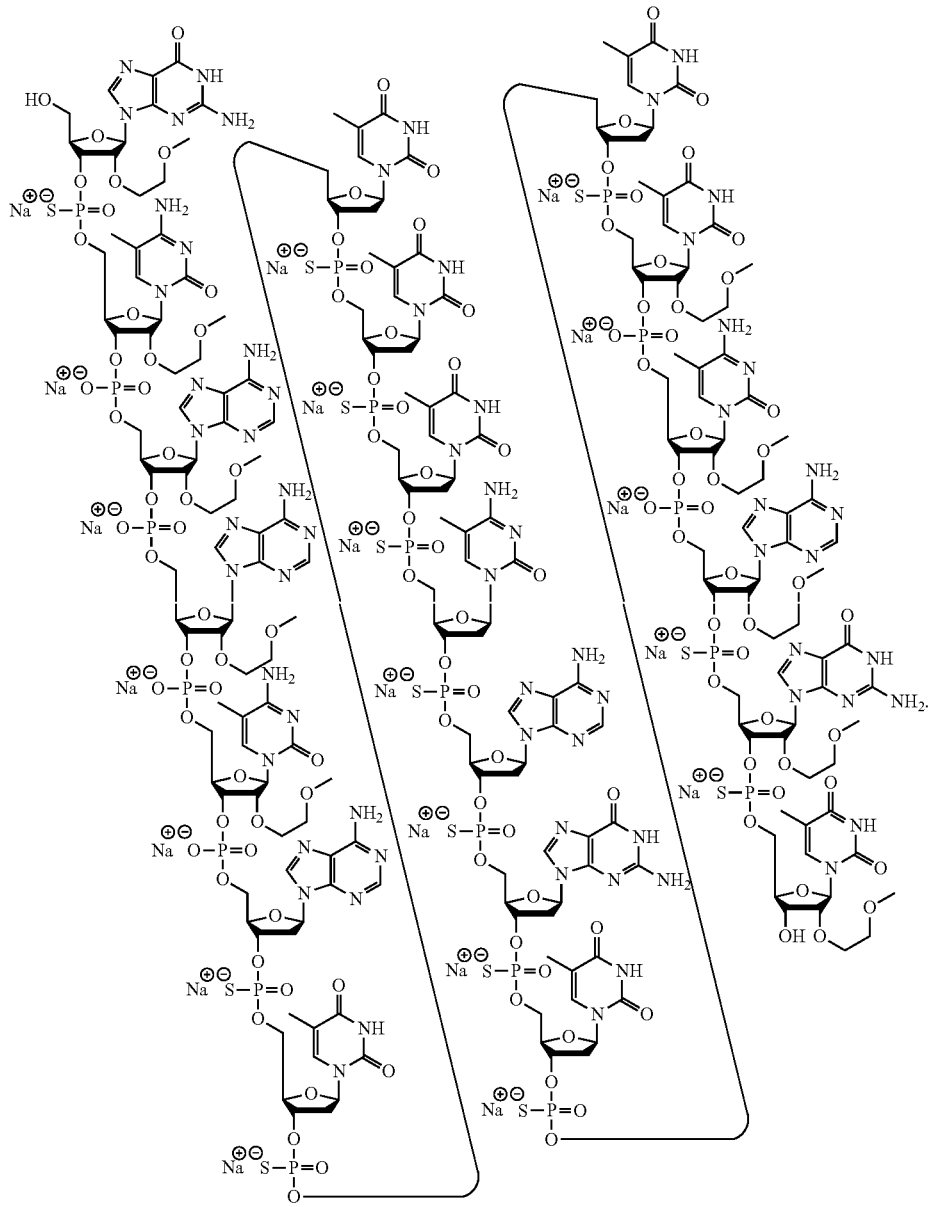

5. An oligomeric compound comprising a modified oligonucleotide according to the following chemical notation:

(SEQ ID NO: 19)
$G_{es}{}^mC_{eo}A_{eo}A_{eo}{}^mC_{eo}A_{ds}T_{ds}T_{ds}T_{ds}T_{ds}{}^mC_{ds}A_{ds}G_{ds}T_{ds}T_{ds}T_{eo}{}^mC_{eo}A_{es}G_{es}{}^mC_{e}$, wherein
A=an adenine nucleobase,
$^m$C=a 5-methylcytosine nucleobase,
G=a guanine nucleobase,
T=a thymine nucleobase,
e=a 2'-MOE sugar moiety,
d=a 2'-β-D-deoxyribosyl sugar moiety
s=a phosphorothioate internucleoside linkage, and
o=a phosphodiester internucleoside linkage.

6. A population of modified oligonucleotides of claim 1, wherein all of the phosphorothioate internucleoside linkages of the modified oligonucleotide are stereorandom.

7. A pharmaceutical composition comprising a modified oligonucleotide of claim 1 and a pharmaceutically acceptable diluent.

8. The pharmaceutical composition of claim 7, wherein the pharmaceutically acceptable diluent is phosphate-buffered saline or artificial cerebrospinal fluid.

9. The pharmaceutical composition of claim 8, wherein the pharmaceutical composition consists essentially of the modified oligonucleotide and the phosphate-buffered saline or the artificial cerebrospinal fluid.

10. A population of modified oligonucleotides of claim 2, wherein all of the phosphorothioate internucleoside linkages of the modified oligonucleotide are stereorandom.

11. A pharmaceutical composition comprising a modified oligonucleotide of claim 2 and a pharmaceutically acceptable diluent.

12. The pharmaceutical composition of claim 11, wherein the pharmaceutically acceptable diluent is phosphate-buffered saline or artificial cerebrospinal fluid.

13. The pharmaceutical composition of claim 12, wherein the pharmaceutical composition consists essentially of the modified oligonucleotide and the phosphate-buffered saline or the artificial cerebrospinal fluid.

14. A population of modified oligonucleotides of claim 4, wherein all of the phosphorothioate internucleoside linkages of the modified oligonucleotide are stereorandom.

15. A pharmaceutical composition comprising a modified oligonucleotide of claim 4 and a pharmaceutically acceptable diluent.

16. The pharmaceutical composition of claim 15, wherein the pharmaceutically acceptable diluent is phosphate-buffered saline or artificial cerebrospinal fluid.

17. The pharmaceutical composition of claim 16, wherein the pharmaceutical composition consists essentially of the modified oligonucleotide and the phosphate-buffered saline or the artificial cerebrospinal fluid.

18. A population of oligomeric compounds of claim 5, wherein all of the phosphorothioate internucleoside linkages of the oligomeric compound are stereorandom.

19. A pharmaceutical composition comprising an oligomeric compound of claim 5 and a pharmaceutically acceptable diluent.

20. The pharmaceutical composition of claim 19, wherein the pharmaceutically acceptable diluent is phosphate-buffered saline or artificial cerebrospinal fluid.

21. The pharmaceutical composition of claim 20, wherein the pharmaceutical composition consists essentially of the oligomeric compound and the phosphate-buffered saline or the artificial cerebrospinal fluid.

22. A pharmaceutical composition comprising a population of claim 6 and a pharmaceutically acceptable diluent.

23. The pharmaceutical composition of claim 22, wherein the pharmaceutically acceptable diluent is phosphate-buffered saline or artificial cerebrospinal fluid.

24. A pharmaceutical composition comprising a population of claim 10 and a pharmaceutically acceptable diluent.

25. The pharmaceutical composition of claim 24, wherein the pharmaceutically acceptable diluent is phosphate-buffered saline or artificial cerebrospinal fluid.

26. A pharmaceutical composition comprising a population of claim 14 and a pharmaceutically acceptable diluent.

27. The pharmaceutical composition of claim 26, wherein the pharmaceutically acceptable diluent is phosphate-buffered saline or artificial cerebrospinal fluid.

28. A pharmaceutical composition comprising a population of claim 18 and a pharmaceutically acceptable diluent.

29. The pharmaceutical composition of claim 28, wherein the pharmaceutically acceptable diluent is phosphate-buffered saline or artificial cerebrospinal fluid.

* * * * *

UNITED STATES PATENT AND TRADEMARK OFFICE
CERTIFICATE OF CORRECTION

PATENT NO. : 12,152,052 B2
APPLICATION NO. : 18/472506
DATED : November 26, 2024
INVENTOR(S) : Susan M. Freier Page 1 of 6

It is certified that error appears in the above-identified patent and that said Letters Patent is hereby corrected as shown below:

In the Specification

In Columns 9 and 10, the structure should read:

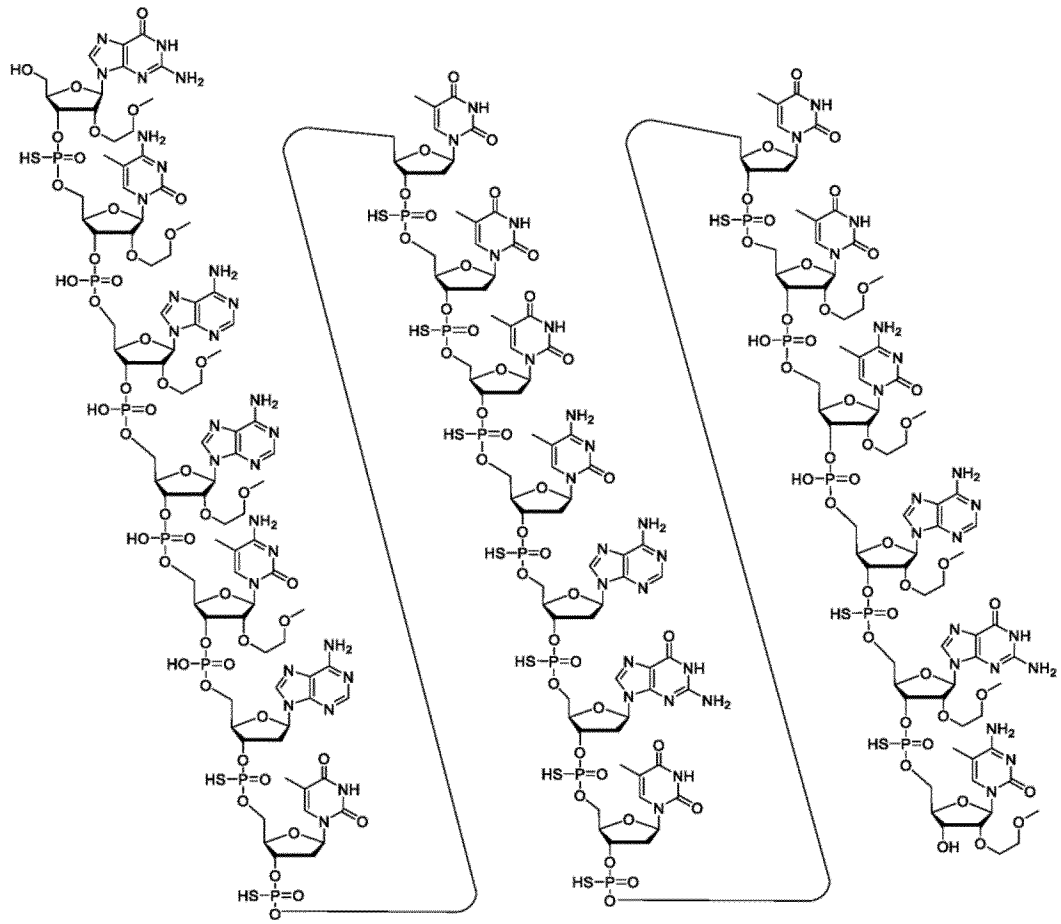

Signed and Sealed this
Twenty-fifth Day of February, 2025

Coke Morgan Stewart
*Acting Director of the United States Patent and Trademark Office*

CERTIFICATE OF CORRECTION (continued)
U.S. Pat. No. 12,152,052 B2

In Columns 11 and 12, the structure should read:

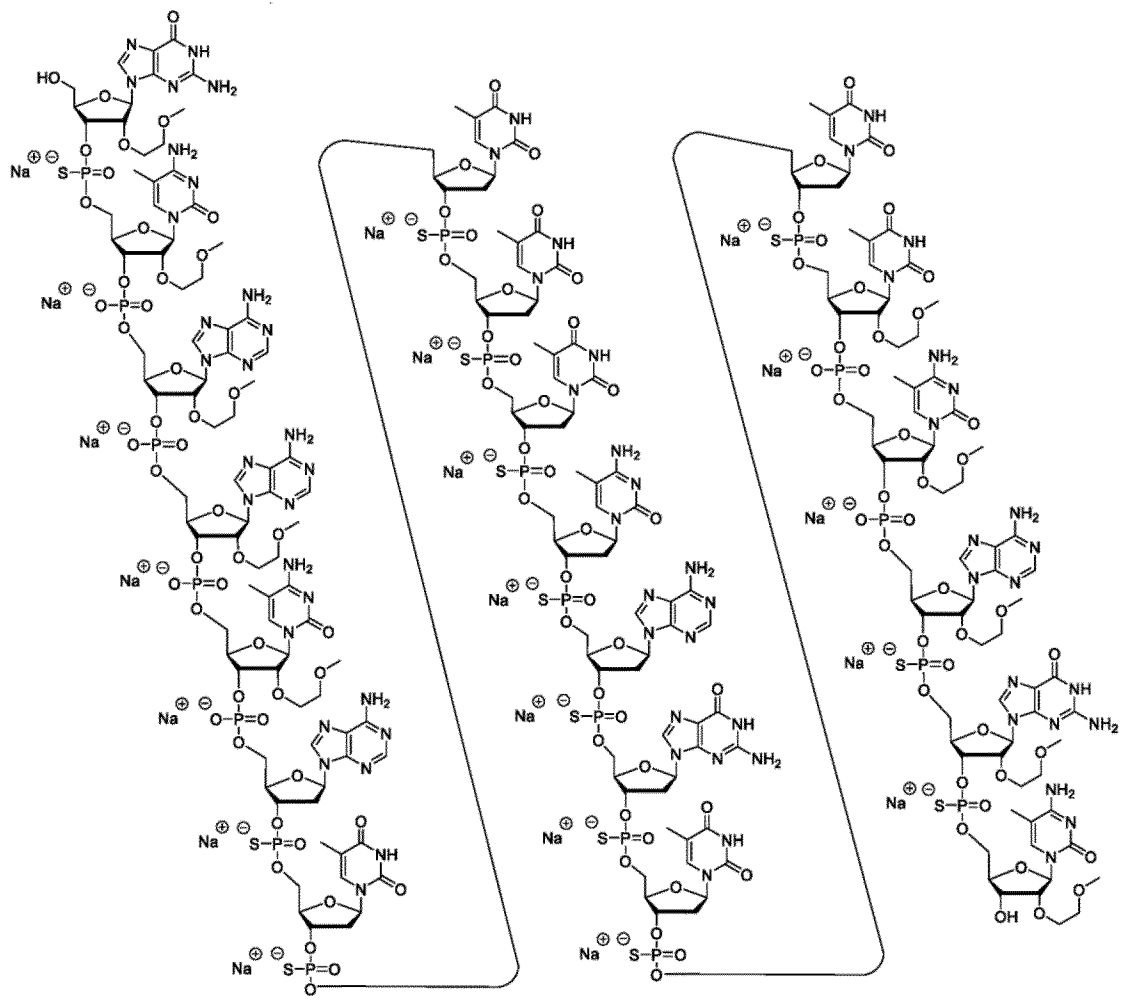

CERTIFICATE OF CORRECTION (continued)

Columns 15-18, the structure bridging the pages should read:

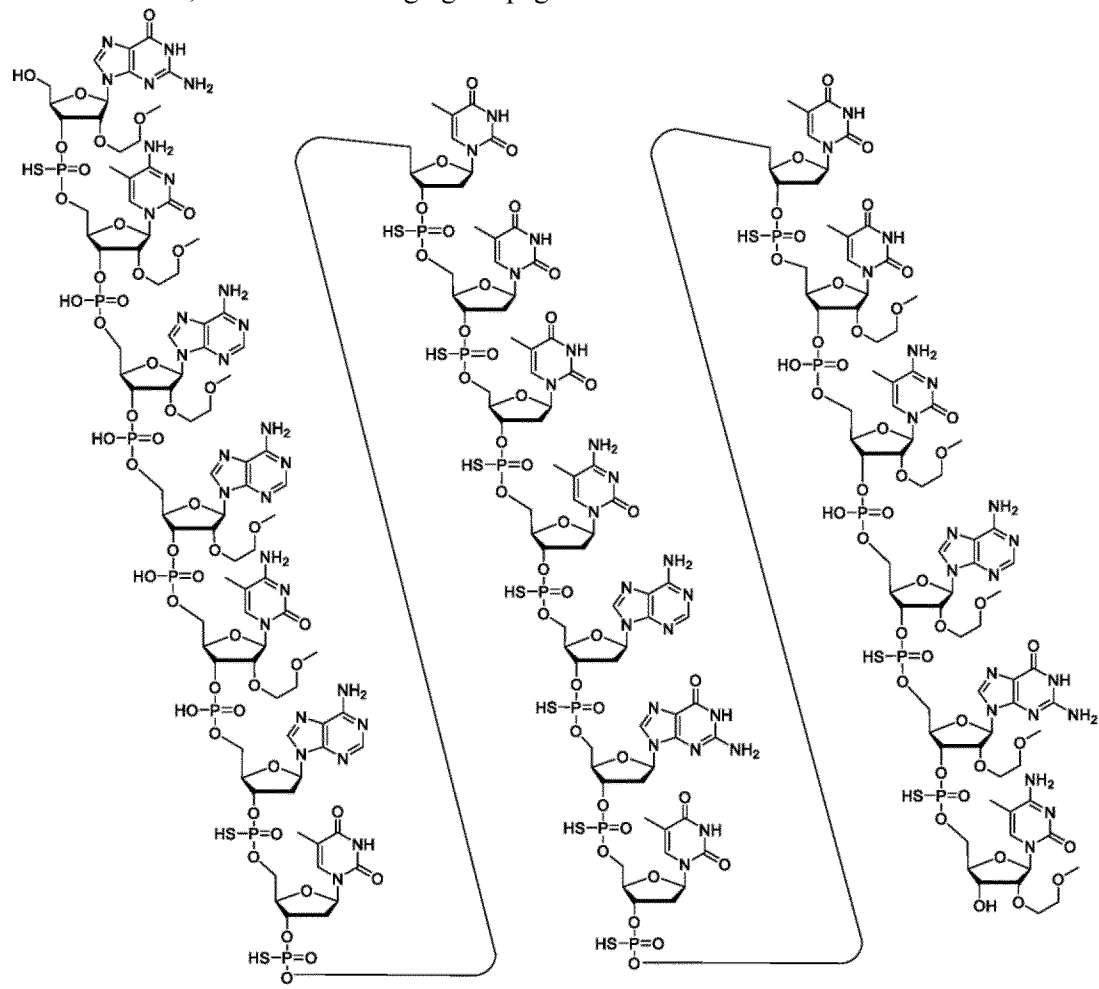

CERTIFICATE OF CORRECTION (continued)
U.S. Pat. No. 12,152,052 B2

In Columns 17-20, the structure bridging the pages should read:

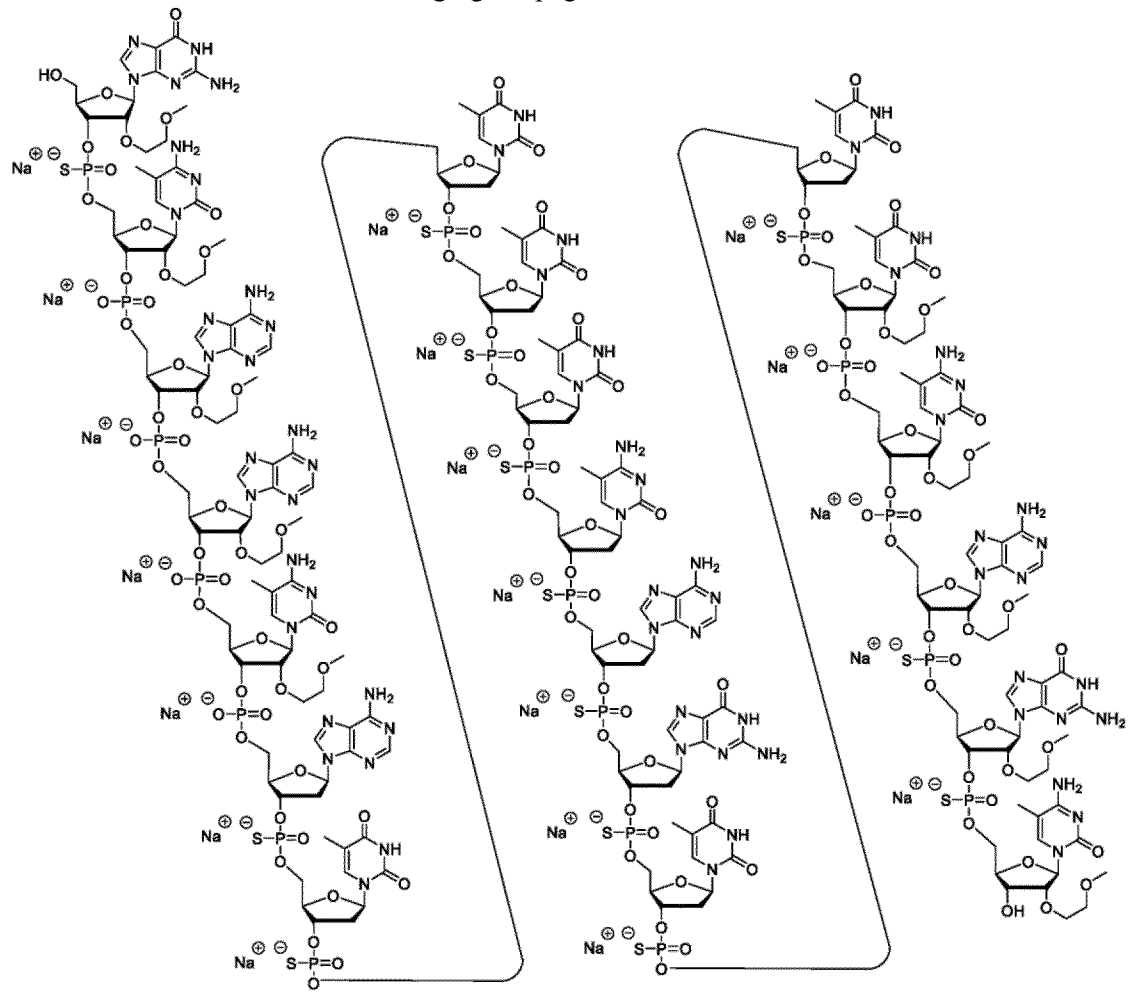

CERTIFICATE OF CORRECTION (continued)
U.S. Pat. No. 12,152,052 B2

In the Claims

In Column 97 and 98, Lines 10-45, Claim 1, the structure should read:

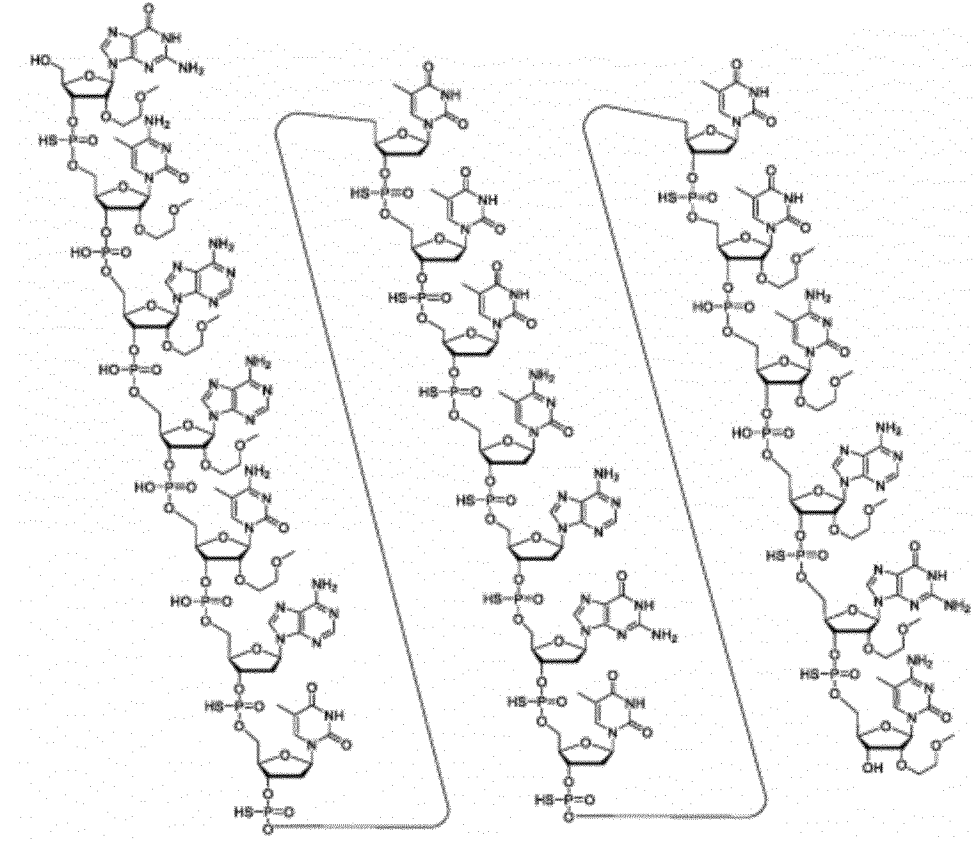

CERTIFICATE OF CORRECTION (continued)
U.S. Pat. No. 12,152,052 B2

In Column 99 and 100, Lines 1-49, Claim 4, the structure should read:

SEQUENCE LISTING

```
Sequence total quantity: 21
SEQ ID NO: 1             moltype = DNA   length = 82000
FEATURE                  Location/Qualifiers
source                   1..82000
                         mol_type = genomic DNA
                         organism = Homo sapiens
SEQUENCE: 1
gacagggtct tgctttgttg cccaggctag agtgcaatgt gcaatcatag ctcactgcag 60
cctcaaactc ctgggctcaa gtgatccttc cacctcagct ttccaggagc ctgggactac 120
aggtgtgtgc caccacgtct gtctaatttt taaattttt ttgtaaagac ggggtcttgc 180
ttcttgctat gttgcccagg cttgtcttga actccagttc tctgattttt aaaaaaaatc 240
ataagtagat gttgaatttt atcaaatgct ttttctgact ctattgaaat aattatgtag 300
tgttttttccc cttaagtttg ttaaggttgg gtttctaatt ttaaaccata tttgcattct 360
taggataaaa ctcaactcgg ttgtgataga tcatatactg caggattcag tttatttgtc 420
tagaatttta aaacttattt ccacatcttg tgtcatactt ttcttggctc atcatagtag 480
atatattagt ctagtaaaat aagtttggag acatttattt cttttctgtg tatgattgga 540
attgcctact cattaaagat ttggtagaag tcatccataa agccctcttg gtctgtttct 600
ctctctctct ctctctctct ctctgtgtgc gtgtgtgtct gtgtgtgtct gcgtgtctgt 660
gtctgtgtgt aggaggatgg gtagcttttt aaatacatag tcaatttcat tgtggttaca 720
gggattttct gtttctaaag tcggttttgg taagctgtac tttcctagga atgtattcct 780
tttgcttatg ttttcaaatt tactgacaca cagtgcataa taaaacctt tcatgagtaa 840
cataatttac ttttctcttt tctctttata tccagcttgt tagaggggtg gcttttgttt 900
ttcagctttt caaagaagca ggtttaaaat tttctcaatc ctctccatca tttgtttcta 960
tttcattaag ttttattcat ccttattttt ctttcttcta cttttgcagg cttactctgt 1020
catttcttta tggcttcttg aattggatgt tcagcgtgat gacttttgga ctgctttagc 1080
cgcatctcta tacttcagca tcgcacaccc aatggcttac tcaacatctc cactttcaca 1140
ccactgggca ccccaagctt aatacagcca aagcagaact cttgatctgc acctctgaaa 1200
atgtactttt cctgtagttc tccccactat ggtgaaaagc acccttattt ccccagttgc 1260
tcaggcccca atctcaggaa tcatccttgt ttcttccctt gctctatgcc tacatccaa 1320
tccttttgtt cagttctgaa aacatatctt gaatctcaca acttctcaga gctgcactga 1380
tgccacccta gttaaagcta ccatcaactc tttctcctag actgttccag ggccttgcaa 1440
ctagccttgt gctgtagttt tgtttcatca cgtccagttc tccactctac acctgcaaca 1500
tagatcagac agctcctggc tcaaaatcct ctgagggctt ctcatcttag aataaactct 1560
cggttctggc cgggtgcggt ggcttacgcc tgtagtccca gcactttggg agtccgagc 1620
gggcggatca cttgaactca ggagtttgag accagcctgg gcaacatggt gaactcccat 1680
ctctatcaaa aatacaaaaa cttagccagg cgtggtggtt cgcatctgtg gtcccagcta 1740
cttaggacgc tgaggaggga ggatcgcttg agctcagggt ggacgttgca gtgagccaag 1800
attgcgccac tgcactgcag cctgggtgac agaatgagac cccatcccca cccccccaa 1860
aaaagaatga actcccagtt ctcatagtgg cccaagctgc cttttcaatc acattccta 1920
ccactctcca gcaacactga cttcctcgtt agtcccaac atgccaggca tagtctctcc 1980
tcatgtcctt tgaacttgcc tggaatgttc ttttcccaga tattcatatg agggagtaaa 2040
atgagggtga aaaccagcag atatctaaat agcacccct tcacttagtt tatctttctc 2100
aaagcccta tcactatgtg aaatgatata ttatacttat ttgtatgcta gtatgaatct 2160
tcccggcaag aatgttagtt tgctgtctgt tcagtaccgt gcatccagag cctggaagag 2220
tgcctggcac atagcaggta gtcaataaat gaatgggggc aagcagccaa atcagaatca 2280
ggttttcttg ctaagcatag aactaacaga aggatcattg aatggattgg ataatgactg 2340
gcatcagggt aaggtcccct taacaaacac tcctgtcctg aacacctggt tagctaacag 2400
ttttctcata ctcttatttt cccaaaacac aattgctgga tctcagctcc aaatcaactc 2460
ttctaggaaa gtgaaaaatt gctggatctc agctcccaaa tcatatcttc caggcagagc 2520
taacattgcc ccttattcac acctccacca aaccatctga tccaacagtg acaggtgtca 2580
cgaggccttg gcatgcactc tcttcccccg ccagagttct gcgaaagcca gggttgcgat 2640
ttgttgtcag tttattcccc gcctctatga gagtgtgagc actgggcagg ctcggatgaa 2700
ataatgcatt gagtaggcct ctgaaaccaa ggccctcag ctggggcaac gtcaggctcc 2760
agggtgggca actttgctgc ttctgccgaa gatagtgata ttgagaaaat gtgggtgcaa 2820
tgaaacgctt attgcagcgc actcggtgca tctgtggaca gagggtcaat cgcccctcag 2880
agcagcgcaa acaggcgtcc caagcctagg ccttcacttg cccccagcatc cgcaagggtc 2940
cattaatcct taacattcaa attccgccca ctaaaccagt ccctccgcgc ccaagccgcc 3000
tctttttccc aaacgacggc cgaaagcagc caatcaacag ctgagggggt ccgccccctt 3060
```

```
ttccctggcc gaaatggaca ggaaatctcg ccaattgacg gcatcgccgc tgagactccc    3120
ccctcccccg tcctccccgt cccagcccgg ccatcacagc caatgacggg cgggctcgca    3180
gcggcgccga gggcggggcg cgggcgcgca ggtgcagcag cgcgcgggcc ggccaagagg    3240
gcggggcgcg acgtcggccg tgcggggtcc cggcgtcggc ggcgcgcgcg ctccctcctc    3300
tcggagagag ggctgtggta aaagccgtcc ggaaaatggc gccgccgcc gccgccgcg    3360
cgagcggagg aggaggagga ggcgaggagg agagactgtg agtgggaccg ccgtggccgc    3420
gggcggggac ccttgccggg gggcgggggt caggggcggg acgtggccgcg ggaggggccc    3480
gcggggtcgg acgacacggc tggcggatgg cgtccctcct ctctaccctc cccctcccgc    3540
cgccgccggt ggcgactctc ccctcggccc gtcacccctg ctcgcgggtg accgtcctcg    3600
gcgcggcctc cctggagccg ccttcgcctg acgcccctct tcctcccgcc ctcgacgcgc    3660
atccggccc ccggccccgc gggcgcccct gtcgccgggg cttcgcctgt cggggctgcg    3720
cgcgctcctg cccttctcgg ggctttgggc cgcggcgccg tcgcgcgccc gcggcccgg    3780
cctctccctg gatcgcgctc tcccctccc tccctcgcgc gcccctctc ccgttactcg    3840
gcccccccac cggcgcgcgt gcgcacttcg cctcccgtcg ggagagtgcg gcacaagggc    3900
tcctgagctc tcaccccat ctctgggctt tgcctccccc tccttctcgc ccattccatg    3960
aatttctgcc ccccgctacc ccccgcgag cgagtaggtc caccggctcc tttcccatc    4020
tagcaggaac aagtaggtgg ggattattat ccacaaaagg gactagacat tgtgttctgg    4080
gtcccacaac tcatcataaa gaggtggtta tagttcccat caggagccgt gggtagggga    4140
ctgtgcgtcc agcagcaccc gaggctcttc ggcgccagag gctctaaggt gcgagcgtgt    4200
ccccagggtg ctcagaggtt cttggagtg ctgtggcctc ggaatgtgag caccctccca    4260
tcctaccctc cccttcgccg gcgatcttcc agttacataa gtggagtggg acatagtagg    4320
taacgggctc tcatcgccct ggagcgctcg ggatcaccgg taccagatgg ggcaagttca    4380
tcgcgacgct gtggctcctg ttaattgtgc ctgaaaggtt atcctctgtt cagtttggtc    4440
atgaccgaat cacccaaact gaaactcaga tgactttat atggcagtgg caatgtttct    4500
gtggttttgc actaaagact taaggtcatt atgaagagtc taaaaggatt gctgtcgcag    4560
gggagaccgt ttatgacatt gctaagtatg gaccccgagg gggaaaaagc tcattcagtg    4620
attgctctgt ggcggttgct tctgttgcga gtgtgttcgg gtgtggggttg gtcacagcag    4680
aaatgggctc caccacaaaa ttgatattcc tgactcatgg tcaggcagat gtgtgcttct    4740
ggttattttt ccaggaacag gaatgggctc tgccgagcct ttcacacgtt gtgtctctgc    4800
tgtgcgggat cagtacccca gactgtgaga taacaggatc ggaattcaggg gttggttggt    4860
gatccaggaa ccataccac ttggatgtga tactgagtgg cctagacgtt gtaggactct    4920
cataagtttt agacattttg ttatactgta aaaatgaagc atatacggcc tcagtagtaa    4980
cattgcacta ataggtaatt attactctag agaattttgg gttccatggc tggaatgttc    5040
atcagtatct cagcaatttc agttaataac cagattagc tgacctcttg agtcttttga    5100
aatctgctgg gtccctataa taagacaggg tctggatttt ttaatcttt gggaatttcc    5160
accaaggatt tagggaaata ggcttttatg ggcttttcag gatttctatt tcaaatccca    5220
atgaggaagt ctaggaaaca cttgcttta ttttcttgcc tgaatatgtc agaaccttaa    5280
atcacccaat caatctagaa gtactacagt tgattaaagt aagtcaccac aggtcaccca    5340
tcgtggcag gtcagctagg tggctgatca ctggaataca gtcatatccc caggcataca    5400
cacgagcctc acttgacgat cccaaagttt gtacatctga gcttgagacg tgacaagttg    5460
aggtctctgc tttgttcttc atagttggca gtttgtctcc tcgggtgccc ctccggttag    5520
ctgtttatca tacgtctagc cctatcaaca gtgcaggcag cttccagagt atagttttct    5580
ctgcaaagtg cctggtggag gggtacctcc ttttccattg tcctaatgcc tccactgggc    5640
ttccatacca gcccttttcca gtgtcttaac agctcaaaga aacccatctg tggctttctt    5700
gttagcactg gcctatcaca ccttcctatt gcctgttaac taaaattttg cctgaaatgc    5760
tttaagctta gagtactggg tctttgtttc acccgattga taggagagtg tcatgcagtc    5820
agccgaactc cgacttctgt gctgttttaaa tccttaggta ggtctggggc aaggcacaaa    5880
ccactgtgta ttcaaagggg tatggtgctt gcattctgtg tgtatatgtt tgtaatttcc    5940
aaccagagtc gtttcccgtg cctgccctgc ctctgtgcaa tctagtctag tagggtaggg    6000
aggcaagctg tggagtttga aaaaaaaaa aaaagctag atgagtttaa taggctgtta    6060
cccctccag aacattcctc ccatgtggag atgaaacgag aagttcattt ctttaaccta    6120
aaataaagaa caacagagat aaaattgtta gttccttatt ggagcctggt ttccattgct    6180
aatgtacctg cttgggactc tgcatgataa atgacgtgtc ctggaacctg aaatctttta    6240
taaaggttaa tatcagcaga aatcttttaa ttagctaaga gcagcttgtt ctcaagctgc    6300
ccgagttatc ttggaggaga gaatcacagg aaatgtttta tatttctagt aaccagtgtt    6360
ttcagtgcgt ggggtaaagc acactcctag actggccagt cccaaagagt gtggcaggac    6420
acctgcttgt tttccctgcc ctctgctatg gtgacatcct tgcagaccag tcttgcgtgg    6480
ctggcagacg caatctttt ttcttgggta gagcattatc accgctgcga tggaaggacc    6540
ttgtcctcgg tgcctccata ccagcccttt ccagtgaaac tactgctgtc ccggcaagcc    6600
cctgtgcgtg tgcatcattc cgggtaggac aagatgtgaa caggtccctc ttctttgggc    6660
ttaagtagaa gttgtgctct tctgctttta cctgtgtgct cttctgcttt tacctgttct    6720
cttctgcctt tctcttgcaa gaaacctgtc gaaagcttgc tttgcatgcc attgcttaaa    6780
tactttgatg gtatgtatgg tatgtgggat aactgagtgg gagccggaat tgggggtgg    6840
gcagggcatc cccacccca cccccacatc aaagggggaa tgaccatttc gttagagaat    6900
aaagcctgag tcttataact tcttcaagca catgtatgct gggtctcctg gcgtgtgaat    6960
gtgttcccgc tgtgctgtgt ggctgttttg cagttactgt agacactgta gtctgggctc    7020
tcattattgc ctctgaagtt gacaggacca agccttagta aggatgcact tgtcttccta    7080
gcccaagagc tagggggtgtt ttatatatat attaactttc tttttttagat ttcataaact    7140
gctctcattt tctcttttct ttctttcttt tttttttttt tttttttgaga cagtctcact    7200
ctgtcaccca tgctggagtg cagtggcacg atctcagctc actgcaacct ctgcctcccg    7260
ggctcaagca gttctctgcc tcagcctccc aagtagctgg gattacaggc acctgccacc    7320
acgcctggct aatttttgta tttttttttt tttttttttt tttttttagt cgagacgggg    7380
tttcaccatc ttggccacgc tggtcttgaa ctcctgacct cgtgatccac ccgccttcagc    7440
ctcccaaagt gcagggatta caggcgtgag ccaccgacc gctcttttctt    7500
tttgacatga aatcttaagt taattatctt aaacttaag aactagaagg attcttagtc    7560
cagcaccatc agtttacaaa caaaaaaaac ttgtgtccct gagaagttgt gacttttcca    7620
gggcctccta gccaggatac cagttggtt tttattatat agctagccga gtaatactat    7680
taacttgact tctgggattt caaagtattc tatgacttga ctgtttaagg gaattatgag    7740
gcctcactga acctcaaaag ataatttag gtaccatcct ggtagctgta gagcagcaac    7800
```

```
agaccagtaa aagacttggt tggtgttgcc cttcttctgg gtttgattac atgagtaatt    7860
gtgtgaatag tctctaagtt gtatgctctg agctttcgtt tttagcttat aaaagtgcta    7920
ctcttgggcc agcatagtat cagaaattag ctaattcata tggggcagtt taggctttaa    7980
ctaggaaatg atggttatct taatgacaaa aaaggtactg acaaaagtcc ttttttgaac    8040
atgtgttcaa aagaaaaaga gaaactatca aactaataac tgagtttgtt gaacatcgag    8100
attgactgat ctgagaggct taaaactgat tgccctgaaa tagacttgca tgttttggat    8160
gatggctttg ggtctcccag agcacttggt ttcccttggt gctgattttt tctctcagga    8220
ttaaagcccc tttatgtgat gttgttacag cagcttattg caacttcatt cagctgcttg    8280
aaaaagaagg gagactgcct ctaggttcca tgtgttcttt agggatggt attttgatgt     8340
tgcgtattct cttgaacatg tattcttccc tgagaatttc tgtgtgccgt ggtagaagaa    8400
atacttgcca gaaatcgcca ctcatggtat gcttttgtag tgtcgaagtg tccctagag    8460
gtgacaaggc ttgtgatagt gttgattcta acaagcatga atctttcctt tattttagca    8520
ctgtgtgtta cgtgccagta atttgcagct tatcctttgt ttctagctag gtaagctggg    8580
aaatagccta gtactttgtc tatgtgttta tcttcaaaat gtcccaaata gccctgggaa    8640
aaaggtcgtg cagctcaatg ggggctttca acttacaatt ttctttgttt taggctccat    8700
aaaaatacag actcaccagt tcctgctttg atgtgacatg tgactcccca gaatacacct    8760
tgcttctgta gaccagctcc aacaggattc catggtagct gggatgttag ggctcaggta    8820
agtaaccttc cttttttttt tttagtata tgtcctggtt tggccatctg ttttttttt     8880
tttaaaaaa aaaaaaaaaa ggaaaagagg aaaaaaatat actactcttg gacagtataa    8940
aagtacccca aagactaaag acataactgg gccaaactgt gccatataat aaaaaaaagt    9000
cacttccctg agccctgaaa ggtcagtgtg tgtagggtta cttggtcgcc acagcgtgat    9060
ctgggggcgg gcgtcagatt agagccggaa ctggtgatct gcaacttcag ttcaccttga    9120
agcaggtcag ctgagctgag agcgcttgca ctgagccctt ttgcgctgct gctgttgcct    9180
tagcggtctt cagcatgtgt ttgctttggt ttggggtaaa tggcttagtg gtcaacatta    9240
gtgagcagtg gtaatgcatt ttcagatatg ggaactggta tgtggttggt tccctagaag    9300
gacaccctcc tgaaagctgt ctcagaacac cgggggccat ggctaatgtc atgtgcttgc    9360
tacactcctc ccatggtaac taaagagagt acccagatat acatctggtt cttgggactc    9420
tagaggagga tgagtacttt gtaaaaacct ggggcccca gtcattctag gtctgacact    9480
caggtgctgt atcagctgca gtttgaacta cttggcacca ttgtgtggac tttagttttg    9540
taaaaatgaa tggttcctta atttctcaac cttcaggctc aacatctcaa gctgtttgtt    9600
gttgttgttg ttgttgttgt tttgttttgt cttttttgatt agtggtcact ccgcatttga    9660
tgttttgaca tgtggatttc agaacttctg tgtggtaaag cagaatgttc caattgaatt    9720
ttcccatttt ttttccccta agcaaaaatg tgagttttca cttatgcggc cattgtgatt    9780
ccgactgaga ccctaagtcg ttctttgttg tctctctagt ggtttctgac acctcagtgt    9840
gaagctgttg tagacatcca taagaaatag cctgcttagg gattatgtga gggcaaggtt    9900
tggctgaagg agaatagaag gtgtggaagg aagcggaaga ccagaagagc atcacactgc    9960
ctcaagtccc aaatttgatt ctgctcctga tcctgtgact caaattgtca ttctctttta   10020
ctgctgtggg gtgtgctctg ggcccagctg acaggacatt ctttgtactc cacgtatttta  10080
tgctggtggg agttgtatgg ctagtgcttt gtgctttgtc tcagaaattg tgtggactaa   10140
atgtaatatg ggcagtgaat gggtttcttc tggaagatgt taggcctgga gggtggtttg   10200
ggttttacg agtctttttc tcagattaca gattacgaat ggatgttata aaacaggcag    10260
tgttgacacc atacagtttc tcctaagaaa tgtacagaga gttcaacctg aggaagctaa    10320
ttgaaaataa actttttaaaa agaaaatgtag aagaggaaaa tttaaaaagt atcttatgaa   10380
tgggaaagat gtagccattt gagcttcaaa gaactttga gggaattctc aaaggacagt    10440
acccgtcttt agtagataaa tgcttgatat ctatttttct tcttttactt tttaaagaat   10500
tactaaaata atacatggat ttatagaaaa atcaaaccac ttaaaaattg atcaggtggc   10560
tgggcaaggt ggctcatgcc tgtaatcaca gcgctttggg aggcctaggc gggtggatca   10620
cctgaagtca ggagttcgag accagcctgg ctaacacggc gaaacccat ctctattaaa    10680
aatacaaaaa ttagctggcc atggtggctt gagcgtgtag tcccagctac tcggaaggct   10740
gaggcaggag aatcacttga acctgggagg cggaggttgc agtgagccaa gatcaccaca   10800
ctgaactcct gcctgggtga cagagtgaga ctcggtctca aaaaaaaaaa aaaaaaaaag   10860
tatcaggtaa aaaaatgaaa gctccccgct taatctctgc tcccactacc cagaataact   10920
gctgttaata gcttaatgta gatccttcta agtcttctaa gactaaactg tgtacttttt   10980
gtgttgtaat taacaggagg gttttgttt tgttttgttt tttctttttt tgagatggag   11040
tcttgctctg tcatccaggc tggagtacag tggcacaatc ttggctcact gcaacctcca   11100
cctcctgggt tcaagtgatt ctcctgcctc agcctcctga gtagctggga ttacaggcgc   11160
ctgccaccac acccagctaa tttttgtatt tttagtagag atgggttca ccatgttggc    11220
caggctggtc tcgaactcct gacctcaggc gatccacctg ccttggcctc ccaaagtgct   11280
gggattacag gcgtgagcca ccgtgcctgg cctcaggatg gtgttatata tacatattct   11340
gcattttttcc atctcatata ttcatcctg cctcatttct tttaaatagc agtgtagtcc    11400
agggctgact taccgtcatg catttcgttg tctctctatg ttattaaaaa tgctacagga   11460
ttgaaattcc tcatgtgcca gtcatttga agaatgctg cctagacttg gaatttctgg      11520
tggataccac cacatcactg tccaaaatgg ctatcccagt tccccaacaa gtctgagaaa   11580
gtgccatttt cccatatcgt cccagaattg gatatacatc tttttaaattg gtcgcgcttg   11640
gattattact gaggctaaac ctcaataatc attgtcatag ctcttaatgt attaaagatg   11700
ttaactcttt gtcatgcaga tatttcctg ttttgtctta cgtcttgatt cttgtctttc    11760
tgatatataa aatttatgtt atgatttatt cttttgcttt catacttagg aaatcctttt   11820
ttactctttt tttttttttt tttttttttt ttgagacgag tctcgctctt gtcgcccagg   11880
ttggagtgca atggcgtgat cttggctcac tgcaagctcc atctccgggt tcattccat    11940
tctcctgcct cagcctcccg agtagctggg actacaggcg cccgccacca cgcctggcta   12000
atttttttgt atttgtgaga cagggtttca ccatgttagc caggctggtc tcgatctcct   12060
gaccttgtga tccgccgtc tctgcctccc aaagtgctgg gattacaggc gtgagccacc    12120
gcgcccgcc aggaaatcct ttcctactct taacaacaga tcaatagtca tctatatttt    12180
cttcctaaaa aacctgatga tgtattatat tcatacatac gtatttaata catacaaaag   12240
ggccagatgc ggtggctcat gcctgtaatc ccagcacttt gggaggctga ggcgggtgga   12300
tcacctgagg tcaagagttc aagaccagcc tggccaagat ggtgaaatcc cgtctctact   12360
aaaaatacaa aaattagcca ggcgtggtgg cgggcacctg taatctcaac tactgggtg    12420
actgaggcag gagaatcgct tgaacccagg aggcagaagt ttcggtgagc caagatcacg   12480
ccactgcact cctgcctggg cgatagagtg aggctctgtc tcaaaaataa aaaataaaaa   12540
```

```
taataatttt atagttaagt tgccctgtgt ttttcctgtg attaaaaaaa aaaatacctg   12600
ttttgtattt aactttgggg tgggataagg tatagcccac ttagtcagtt gtgtctaagc   12660
cacttgatga accagtcaat ccagtcttca cctttaacaa atgctgattt cttcaagtga   12720
gcaaaatatc tcttaaactt tttcctattt tctctataaa gttgcttttt tctgaatttt   12780
ttctttatga ggcttgatgg gcagccctat cagcagacaa tcattcattc acccaacaaa   12840
tatttgagta tctgcttcaa gccaggggca gtgctaagcc ctggaagtgg tatcttctcc   12900
ttatccggga gtgggctac agtgttcatt ccagaagact caagaaaata gcagatcatc   12960
acaaaagtag gttttacata aatgaggagg aatccacagg gttgtgtata tgtgtgtgta   13020
ttttaaattc tgacataagt tggagcttta gggtagactg tgacataaga gtagtttgtt   13080
ttccaactca tgtaattgcc ggctgatttt tgtcttgaat tatgataatg gtaacttctg   13140
ttgaaacaat tctgtattca tcttagcttg gttgggatgc aataaaagtt ttgtactggt   13200
aaaaatgata attttcttcc atgatgattt tgaagctttt ctgtaacacc tgataaaaat   13260
agaggggcca ggcatggtgg ctcatgcctg tagtcccagc tactcgggag gatgaggtga   13320
gaggatccca tgagcccagg agttttaggc tacagtgagc catcatcaca ccactgtact   13380
cctgtactct agcctgggca gcctcgttct ttagagtaag acactgtctc tttaaaaaaa   13440
aaaaaaaaga aaaagaaaa aagaaaagg cttttagtga atatatttt agggtagcaa   13500
gtgtaattttt tataaattgc attatttgaa tctaataaat accctcaaag ctgaagtcga   13560
attctgattt tgattgaaaa tatttttttac ttaaaggaag agggataga taaatgacac   13620
gattaaggaa aagacttctt gtataaggcc gggggttttt aaatgatttt ttgaatagtt   13680
agatggacaa tacggaatta aaaaggtggt gtaaaaagtt atacggggct gggcacagtg   13740
actcacgcct gcaatcccag tactttggga ggccgaggtg ggtggatcac ctgaggtcag   13800
gagttcgaga ccagccttagc caacatgacg aaacatcatt tctactaaaa atacaaaaat   13860
tagctgggct tggtggtatg cacctgtaat ccagctactc gggaggctga ggcagaagaa   13920
tcgtttgaac ccaggaggca gaggttgcag tgagccaaga tcgtgccatt gcactccagc   13980
ctgggcgaca gagtgagact ccatctcaga aaaataataa tagaaaaaag ttatatgggg   14040
ctgggcatgg tggctcatgc ctgtaatccc agcagtttgg gaggctgagg cagcttgatc   14100
acttgaggtc aggaattcga gactagcctg ccaacatgg tgaaactccg tctccactaa   14160
aaatacaaaa attagccaag cgtggtggtg cgtgcctgta gtcccagcta cttgggaagc   14220
tgaggcagga gaatcgcctg aacctgggag gcagaggttg cagtgagcca agatcatgcc   14280
gttgcactcc agcctggacg caaagagcgg aactccgtct caaaaaaaaa aaaaaaagag   14340
ttatattgta aagtatctct gctaccctgc cccaaacatt catttctttc cctggaggca   14400
gccactatta cctgttttctt taaaaaaaaa aaaaaattgt ggccgggcac ggtggctcac   14460
gcctgtaatc ctagcacttt gggaggtgga ggtgggtgga tcatgaggtc aagagatcga   14520
gaccatcttg gccaacatgg taaaaccca tctctactaa aaatacaaaa aattagccgg   14580
gcatggtggc gggcacctgt agtcccagct actcgggagg ctgaggcagg agaatcgctt   14640
gaacctggga ggcagaggtt gcagtgaact gagatcacgc cgctgcactc cagcctggca   14700
acagaatgag actccatctc aaaaaaaaaa gcgtgtgtgt accgtgtgt taaatttta   14760
ttataaaata tatataacag gctgggcgtg gtggctcacg cctgtaatcc cagcactttg   14820
ggaggccgag gcaggctgat cacgaggtca ggagatcgaa accatcctgg cgacacggt   14880
gaaacctcgt cttactaaa aatacaaaaa attagccggg catggtggcg gcgcctgta   14940
gtcccagcta ctctgagagc ctgaggcagg agaatgcgt gaacccagga ggcggagctt   15000
gcagtgagcc gagatcgcgt cactgcactc cagcctgggc gacagaccga gactccgtct   15060
caaaaaatat atatcgatat atataacaat ttacagtttt atcatctta actgtacagt   15120
tcagtggcac tgagtacatt cacattgttg tacagccatt actaccatcc atctctacaa   15180
ccttcgtct tgcaaaactg aaatttcata cctattaaac actaactccc acttctcccc   15240
tttccccac ccaccctct ggcaactact attctactct ttgtctctat tggacatatt   15300
tttgtgtgtt taggtttgtg tatataattt acatgtgtgt ataaatacac aagggtatgt   15360
gggcgttgtg tttttacaca tactataaaa tattgtgcac atttgtttat tttaatgtat   15420
cctgtagatt atttagaatc ggttcataca gagccgtatc attccttta agggttgggt   15480
ttaaatagtc tgttatggat gtaccacaat ttatttaacc agtttttaaa ttttttactt   15540
attttttttta atgttttttt agagacagga tcccactcca tcacccagac tggagtgcaa   15600
cagcatgatc atagcttact gcagccttga actccgggc tgatgtgatc ctcccacctc   15660
aggctctctt gtagctggga ctacaggat gtgccgccat gcctggctaa attttttatt   15720
tttattttta ttttttattt tggtagacac ggggtttcac tgtgttgccc aggctggtct   15780
tgaactcctt gggcttgagt aatcctcctg ccttggcctc ccaaagtgcc gagattacaa   15840
ccatgagcca tggagcccga caagagtagc cttttatttg cagaccatta gagaaaaagt   15900
tgcgtgtaag tagataagca tacgaattta tcactgcaat actgtttgta gagatcacag   15960
agctgttagg ctaggaagaa gttttttagca gttagcacta gaaagcaaaa ctttggaaac   16020
ttccatttca tcaaaagtga cctcatctga gtagggcatg tgagggaagg accttttttac   16080
tcgacaaggg gaacttgccc agttcttgtt tgtgaacctt gaagaaagtg gagcattttt   16140
attttgggac cattctaggt tgtggtagtt ccttggtact cggggttgga gaatctccct   16200
ctgctgctgg accttctgcc tcctcatgct gtaatatgca taagaggtgt cctagaagta   16260
ttcaggaaca ggctgtggtt gctttgttgt tctgtgactg ttgaactctt tatatagcag   16320
tacttttta agctgtacta attgagcatt tattatgtgt cagttactgt cagttacagt   16380
ggaaactatc ctaccctcag cagtcttctg gtctaatggg aggtacagac aggcaaatgg   16440
gctatgactt tacaagaggc taacttcgt gatggagaga agttccagcc actaagggag   16500
cacataaaaa tcagaggaga tcctaccaag aattgggagg taggtcaggg aggagacttc   16560
tttgaaaaat ggcatctaag acctgaacag caaggaaaca ttagctaggt caaggacaaa   16620
gcatcagtgg ggagagatgc atgagtcttt tggaaggaac agcatgtgta gaggctctga   16680
caggagagaa tctctcaggc ccattcgag agtccactgt gtgaagacga ggcatgaaca   16740
accagccagg acatgtggag aggagcattt ttcttttttt ctttttttctt tcttttttttt   16800
tttttttttt tttgagacgt ctttctctgt cacccaggct ggagtgcaat ggcatgatct   16860
cggctcactg caaccccac ttccaggtt caagcaattc ttctgcctta gcctcccaag   16920
cagctaggat tacaggcacc cgccaccatg cccggttaat ttttgtattt ttagtagaga   16980
cggagtttca ccatgttggc ctcaaactcc tgacctagg tgatctaccc gtctcggcct   17040
cccagagtgc tgggattaca ggtgagagcc cccacgcccg gccaggctcg gctttctttc   17100
caggcccgt cacactctta gatgttccct gggcccagaa aggcagcgtg aggtgctctg   17160
cccatctatg ctgtcctttt ccaccccacc ctatccactg ggccctggg gctccctc   17220
cactccaggt ctcttcatgg acccttcttt cccttcactt ctgtcccagg agacctggga   17280
```

```
gactcatggg aacaggcatc atcttctcca gcacagttca ttgtctaatg cacgaaagtg   17340
ctgggctgtg agaaggtcag gagcttacat ggaatgggag tcagctgtgg tacaaagtac   17400
gctgcttagt tctactgatt ttttatttt tatttttaca taagactttg atggtaaagg    17460
aagcagtgtg tgagcaagct gactcctgtc ttgtcaagta ccaggtccac tctgatgagc   17520
ccctgtggac agcactgctg taactcccca agcctggcgt caggaggtgg gccctaagcg   17580
ctgttcccag ctcttcctcc atgctgtcag ctcttccacc attcttcctg gcgtcattct   17640
aaggtcctgt cttcccccgc cctcttcctt cctggcttct acgctcagct caagtagtag   17700
ctgtttgggt acttttcacc cagacttagg aaatgttatc agttggtcgt attcctgtca   17760
gccctcttac tatggaactc aaataggaca gattcagctg aattcccagc cctgtggttg   17820
cactctttgt ctgccctgct tccccaaggt agcctgctcc ctaaaggtca ccgagatact   17880
ccccatgcaa ggttttgtt gtattacaca tgacaacatg gaataaagtg ttttgcaaat     17940
ttactggatg atatcctact atgtggaaca tcctacaact tactcttttc actcaacatt   18000
tgacttttga acctggtctg tactgctccg tgcagaccaa tgttcattca tttgatatgt   18060
ctccttgtgc catagaaata gttttacaat agaagcctgt ccagagccat gagggagaag   18120
gggattgtag agaaacaagg attggcatct ggtttatgtt tacatccttt agtcctgtta   18180
accgagaaga agatatttt atttccatgt ttgcgaaagc tttccacaaa aaaagcatcc     18240
attttctaga cttattaata gggcagtcca aaggttttat ttttagattt gaagaaagc    18300
aaagtaggct tctgagatat gcacatttcc ctgtgtcccct gtctcttttg caacattcca  18360
cattgctgct aaaacttgaa catgagcact ttcaagcatg tgcttacttt ctatgtatga   18420
ctcattttt aaaacattaa agcattttcg gccgggtgtg gtggctcacg cctatattcc    18480
tagcacttta gaaggccgag gcgggtagat cacttgaggt caggagttca agaccagcct   18540
agccaatata gtgaaacccc atctccacta aaaatacaaa aattagccgg gcatggtggc   18600
gggcgcctgt aatcccagct actcgggagg ctgaggcagg agaattgctt gaacccagga   18660
ggtggaggtt gcagtgagca gagatcgagc cactgcactc tagcctaggt gacagagcga   18720
gactctgtct caaaaaaata aaaataaagc attaaagcac tttgtctggt ggtatgtaag   18780
ttttggcatt acttagataa gttgtatttt aagtcttttct acacacaata acttatttt   18840
aaaatacaag tttctgtgta cttccgggtt ttgtgttttt gtaaacagca gaaggtatta   18900
gtccatatta agtactaatt tgttctaata ttttcagctg ttttttggaat tacacttggc   18960
aaaaaaatag acaaatgtct gcagttgtga cagtttgttt ttttgttctt tttaactcca   19020
gaataaataa ttctagtgag tttttttctt ggcttgtaaa aacatgggaa tgattagagt   19080
catcataaca cttaagtagt tatagaaggt tgaacatctg tagtcagttg tataaaattt   19140
cctagtcatc cttccaggtt gtttaagaca aacaaataca tagtatttat taagctctta   19200
taaattttaa ttgtaaaaca tcattgtaca aaactttgaa aatgcgtata ggtacaaaga   19260
taaaaaatta ggcaggcat gccatggctc acgcctgtaa tcccagcact ttgggaggcc    19320
aaggtgggag gatctttga gcccaggagt tcaagaccag cctgagcaac atattgagac    19380
cctatctcta caaaaaatatc ataaaacaaa atagaatcac tctggcgatt ccactatcca   19440
aaaaaaaaaa aaactgctgt taatatttgg tatgtatctt tctagaccaa ggcctccaac    19500
tttggttgag aattcagccg ggtctgtgac cttggatggg aaaaacattc actctttatt   19560
ttcactaatg tctctgaaaa cccagatttt tagctggca tggtggctcg tgcctgtaat    19620
cccagtgctt tggaagcccg tggagggcag atcacttgag cccaggagtt tgagaccagc   19680
ctgggcaaca tagcaagacc ctgtctttta aaaaaaaaaa aaatcagcc gggtgtggtg     19740
gctcatgcct gtaatcccag cactttgaga ggctgaggca ggcagatcac ctgaggtcag   19800
gagtttgaga ccagcctgac caacatggtg aaatcctgtc tctactaaaa atacaaaaat   19860
cagccgggca tggtggtggg cgcctgtaat cccagctact ccggaggctg aggcaggaga   19920
atcacttgaa cccggaaggt agaggttgca gtgagccaag atcacaccat tgcactccag   19980
cctgggcgac agagcgagac tctgtctcaa aaaaaaaaa aaaatccac attttcttca     20040
atgacaattg taagcaacag atcatggtag tattagaata gcagtgactg tcaccagtag   20100
agatcaaaga tactttcata tcatattata gttgttacag atattttgaa atatatatgt   20160
ccatcactgc ttcaaactta aggtaattat tagacccatc tctagatctg gttatttaat   20220
gatttactga agaagcacat attatttgag aacgaactct tgaaatatgt tgttaatttc   20280
tgtgcatttt acacatttca aaacattctt ctgaggaggg gtccagaagg ccaaaagggt   20340
ccatggcaga aaaaggttaa gaacacctgt tctgtacttt gtaccatgtg gctacaaata   20400
taaaaacaga cgttaagccg ggtatggtga tgcacacctg tagttccacc tacttgggag   20460
gctgaggtgg gaaaatcact tgagcccagg agtttgaggc cagcctgggc aacagagcaa   20520
gacccatct cttaaaaacc agtcagctact tgactagtca gttagtgggg gaaaacacag   20580
gtacagtaaa aggagtcaaa attacactta aacttaggtc atcttattat atcaaacatt   20640
tattaacatg tttagtgttt tgtgtatatt atgcaaagtg taatgcaact aaaactgttt   20700
aacacttctc gatatcacat aaatttgttg gtgcataata gcctaaaagt tactttgct     20760
gttggcattt tattttatta cttactatt tatttattta tttatttttt ttgagacaga    20820
gtcacactgt cgccaggctg gagtgcagtg gtgcgatctc agctcactgc aacctctgcc   20880
tccctggttc aagcgattct cccgcctcag cctcctgact agctgggact acaggtgcgc   20940
gccaccatgc ccagctaatt tttgtatttt tagtagagat agggttttcg catgttggcc   21000
aggatggtct tcatctcttg accttgtgat ctgcccacct cggcctccca agtgctagg    21060
attacaggca tgagccacca cgctgggcct gcttttaaacat ccttctagag                21120
tctttcttat ttgcctgtaa gcacgtacac atgttgttgt tgttttgaga caaggtctgt   21180
cgcccaagct ggagcacagt ggtgcaatca cagctcacta cagcttcgac ctcttgggtg   21240
caagtgatcc tcccaatcag cctcccagt aggtgggact acaggtgtcc gctaccatgc    21300
ccagctaatt tttgtatttt ttttgtagag acggagtttc accatgttgc ccagactggt   21360
ctcaaactcc tttgctcaaa cgatccttcc gcctcggcc ccaaagtgc cgggattaca     21420
agtgtgcacc tctgtgcctg gcccacatgt tgtttagat gaatgagatc atatatgtac    21480
ttttgtaact tgctaccttt cctcaacaaa atgttgtaaa tatccatgtc cataaaaata   21540
gacgtatatc ttcactttc cctaaaatga aaataactta acttgcattt tctttttgt      21600
ttttgttttt gttttgagac aggctcttgc tctgttgctc aggctggagt gcagtgatgt   21660
cacagctcac tacagcctcc acctccagtt tcaagtattc cacctacctc agcctccaag   21720
atagctaaga ctacaggcac atgtcacgac gcctggctaa ttttaaaat attttttgca    21780
gaaatgggat ttcactatgt tgcccaggct ggcctcaaac tgctgcctc aagtgatctt    21840
cctgccttgg cctcccaaag tgctgggatt acagtcgtga ccactgtgc ccagcctgca    21900
ttttcttatt ataaaagtaa tacatgttca atggacaaaa aattttcaga aaatatgcaa   21960
agatgaaaag taaaaattgt ccataaatct gtcatctaca gataaagata acttctggat   22020
```

```
aatgttttc taccatcatt tttagtaatc acataacatt tcgttgtatg tctatgcctt    22080
catttaatta agaggcattt ccattatttc tgcatgttca tgactctgaa tgatgatatg    22140
tctgcctgct gatggctaca accctgtttc tgcatttcaa acctctctct tgagctccag    22200
atttgatggc ctcgtcagca tttacttgag ttgctcataa gtgtctcaaa tttaacaagt    22260
cccagtcttg attttttttcc cccttcaaac ctattcctca tgttgtctct atttcagtaa    22320
acaatatcaa catccaccca gttactcagt ccaaaattct aggagtcatc cttgattctg    22380
ctctttcttt ttttttttt ttttgagacg gagtctcgct ctgtcgccca ggccggactg    22440
cggactgcag tggcgcgatc tcggctcact gcaagctccg cttcccgggt tcacgccatt    22500
ctcctgcctc agcctcccga gtagctggga ctacaggcgc ccgccaccgc gcccggctaa    22560
tttttgtat tttagtaga gacggggttt caccttgtta gccaggatgg tctcgatctc    22620
ctgacctcat gatccacccg cctcggcctc ccaaagtgct gggattacag gcgtgagcca    22680
ccgcgcccgg cctcttttt ttttttgata cggagtctca ttctcgtcat ccaggctgga    22740
gtgcagtggt gcaatcttgg ctcactgcaa cctccgcctc ccgggttcaa gcaattcttc    22800
tgccccaacc tcctgagtag ctgggcctgg ctaatttttt gtattttag tagagatggg    22860
gtttcaccat gttggccagg ctggtcctga actcctgacc ttgtgatccg cccacctcag    22920
cctcccaaaa tgctgggatt acaggcgtga gccactgcac ccgcctgat tctgctcttt    22980
ctctcatcat ccctgatctg tcagcaagtc ctgttaggcc aaccacttct cagcatctgc    23040
actgccagta tgctagtcca agccacaaaa cacctctcag aggtacgcaa caggacttg    23100
ttgttgttgt gtgtgtgtgt gttttttttt tttacggta gaattatttt ataacttgaa    23160
gtgtagggat gaccttcctt ttaaaatttt atttattttc ttaattttt attcccatag    23220
atttaggggg aacaggtggt atttggtgac atgagtaagt tctttaatgg tgatttctga    23280
gattttggtg cacccatcac ccgagcagtg tacactgagg ccaatttgta gtcttttatc    23340
cctcaccccc tcccaccctt tccctcaagt ccccaaagtc cattgtatca ttctgatgcc    23400
tttgcatcct catagcttag ctcccactta tgagtgagaa catacagtgt ttggttttcc    23460
attcctgagt tacttcactt agaataatag tctctagttc catccaggtt gctgtgaatg    23520
ccattaagtc attccttttt atggctgagt agtattcctt tgtatatata tgccacaatt    23580
tctctattca ctttctgatt gatgggcatt tgggctggtt ctatattttt gtaattgtga    23640
attgtgctgc tataagcatg cgtgtgcaag tatcattatg caacgggact tcggatgaca    23700
tattgaacaa cttcctcact gatatccttg tgaaacgcta catatttcat gggtctgttt    23760
gttataccaa cactcaattc tgaatgatgg aattatttca catttagtct cttttttcatc    23820
tagccattat agtttagttt aaacaccaag ttccattcct gctgcatgct gaaggatttg    23880
cagtacatca ggctatagtc catcaattca ttccacaatt gagtaagtaa ggtatctata    23940
gtacctcagg ccctgtgtta ggcagggatg gggtaaccta gacagatttg gtacctgtcc    24000
tcatggagct tgactttagc ggcagagaca gatcttagat aattgtacca gtacttaagt    24060
gttcagaagg acaagtatgg aggtgggagc cactccagtc ctctacagtc acgtgctgca    24120
caacaacgtt tcaaccgaca acagagcaca catacagtgg tgttcccata agattagaat    24180
gccatatttc tactgtacct tttctatgtt tagatataca aatacttacc attgtgttcc    24240
agtgatctac agtattcagt atagtaccat gctgtacagt tttatagccc aggagcaata    24300
ggctatatac cgtatagcct aggtgtgtag tatgctacac catcagatt tgtgtaagaa    24360
cactctctga tgttagcaca aataaatcgc ccaatgacac atttctcaga acatatccct    24420
gttgttgagc gactcatgac tgtacaatgg gggaacagct cagcctgcct tccccaagga    24480
ggcaacgccg atgcagggaa ccgagggttg aacagaagtg ggcaaggtgc agagaggaaa    24540
aaggctttcc agatggagaa gagcatgtgt gaaggcccctc agtctggcaa gagcttagtc    24600
ctgtgtggca ggagctgaac gaggggttag gggagagtgg caaagggtcc gggccatcag    24660
agaggtcaac aggggctgga tcatgcagga ttttgaatgt taacatcaga gcgatagaaa    24720
acatgaaggg taaggtggtt tgggttttga attttttatca aaatattgca actactcggc    24780
aacaagttag atataacaaa agaggtcatc gtaaaaacag cagtctaccc cttcccctctc    24840
ccttccctga ctcagacatg acagctttta actgtttctg atttttagttc ctttgatggt    24900
tacctccaaa attaaatcat atgcttatac atctttcttg atttgccaac tttagggaac    24960
tgtgttaact ccctgaaatg aaagagaatg acttagctta cgttacctcc ccatgttgaa    25020
attcatatttc acatttctct gtaatttttt ttttgagatg gagtctcact ctgtcgccca    25080
ggctggagtg cagtgatgtg atctcggctc actgaaacct ctgcctcccg gttcaagca    25140
attctcgtgc ctcagcctcc tgagtagctg ggactacagg cgcacaccag tgcactgggc    25200
taattttgt atttttagta gaggcggggt ttcaccatgt tggccaggct ggtcttaaac    25260
tcctgacctc aggtgatctg cctgccttgg cctcccaaag tctgggatt acaggtgtga    25320
gctaccatgc caagcccaca tttctctgta aattttaaac agtattttag tccatatgtc    25380
agttcccctc tgtttaagat aaggatatta ataaccctac ttttccttcc actttccctc    25440
cttaacttct gcgtcttaaa agctgtactt gaccataccc attcttgcat tgttaacat    25500
gtgtgtttctg ccctgcaacc agcccaagt tgtagcttaa ttctaaagtc gaaaataaca    25560
ttatttacat tattcacacat gtgagtattg ttcttggcga gaccaaataa tgaatgtgcc    25620
caggattaca tttccttctt tacagatctg gaccactcaa aggagaatga ccaatcaagg    25680
tcaaatggat tcccttttct tagactctgt cacctgctta aaatccttgc taggatttaa    25740
tctacttcat attcaaacct tggcttgctt atatagctct ttgttttgcc caccatttct    25800
agttgccttt ttattttgtt tactattcct ccttgattat gttgtaaaat gctattagca    25860
gtgctgttta tttcgtacga ttcggctttt tccccactga agacctttct cttgaaggc    25920
ctctgccctt ctgcaatctg ggcaagtatc tgctctttga tttaaggttg catatacagc    25980
tgtacctgga ccttctcctc actgggctct tgggttggag cccgtgtctt aaacccata    26040
tcttcctttc acatggttta ctccctcgtt ttctggactg catccttaaa taatgtgctc    26100
agatagagtg catgggagt aaactgtagt ggataccgtt gtcacctacc ccatatccat    26160
ttcttctttg cccattccta acagaatcct gatattattc accttctac cttattccca    26220
acttcagaaa ggatccttaa gtcattccac acattgcatt cctttggcaa ctgttactgg    26280
tcaaggatga acatacgatc taagttggtt cactcagact gaagggaagg acttccatgg    26340
cacgttcagg gaagactttc tctttttctc tcactggagt aagtgagaaa ggtgttgctg    26400
tgttaacctca gactgaggga caaagcctga ggataaagcc tgctcaccaa    26460
ggaaggcgga gcagagaaac gggaagaacc tgggtcttga tgccgttgct tagctggtga    26520
ttgcactgtg gctgggcct gtcctacctg agctagggac tcagatagga tggacttct    26580
tactgaatga gccagcttca gttttctttt ctgttacttg taaccaaaag cattgtaaca    26640
gataggtctt ctgagtcact gcatgcctga aatacctttc ttctactctt acacttgatt    26700
ggctgagtat agggttccaa gttgaaaatc atttttctc ctaactttgg aggcatctct    26760
```

```
tctagtatgc agagtaacaa atgcaacaaa tgcctgatgc caatcttatt atggttcttt   26820
tgtaggtgcc cttcttttct cttccttccc tggaagtttt taggatttcg tctccttatt   26880
tttagtgtcc tgaaatctca tgagaatatg tctagagttg tgtcttgttc actcgttgta   26940
ctgtggtcat tcaatctgaa tacttttgtc aactcttttt tttaaaaaaa aattactaat   27000
ttacatgctt tcattttctc tatggggact actgtttaac tttggacctc ttatattggt   27060
cttctgtctt ctctcatatt tttcatttat tgggcggtgg ggggtgctct gaattttgga   27120
agatctcctg catttatttt cttttccctt ttttctttt tttgaggca gagtcttgct    27180
ctgtcaccca ggctggagtg cagtagcctg atctcggctc actgcaacct ctgccttcca   27240
ggttcaagca attctgcctc tgcctcccac gtagctggga ttacagacct gcaccaccac   27300
gcccggctaa ttttttgtatt tttaatagag atggggtttc accatgttgc caggctggtc   27360
tcgaactcct gacctcaagt gatccgcccg cctcagcctc ccaaagtggt gtgagccacc   27420
gcacccagcc tcctgacttt attttctatc ccttctgtta aattctttat ttcagccaaa   27480
cctttttttt tttttttta acttactgtg aagcctgtgt gcctactgcc tagattagac    27540
aattgttaac attttggcgt attttcctgg tctgtataga tagggtgcat tttatacct    27600
ttttgctcac cattaaaag gaactcacag atgtcacgac atttcacccc taagtacttc    27660
agtatacatc tcctaaaaat aaggacattt tccaatataa gcacaatacc ccgatcacat   27720
cttaaaagt taacaataat tctctaatgt tatcaggcac ccactttaa ttcagatttc     27780
ctccaaatgt ctcttatcgc tgttgagggg ctccaaagca attaagattt atacattgca   27840
tttgaatatg cttcctttgt ctcttattta tttatttatt ttattttgag acagagtctc   27900
gctgtctccc aggctggagt gcagtggtgt gatctcagct cactgcaacc tccgccttcc   27960
aggttcaagc gattctcctg cctcagcctc ccaaatagct gggattacag gtacgcacca   28020
ccacgcccag ctaactttt tgtattttta gtagagacag ggtttctact aaaccatgtt    28080
ggccaggctg gttttgaact cctgacctca agtgatctgc ccgcctcggc ctcccaaagt   28140
tctaggatta taggcgtgag ccaccatgcc cagcccttt gtctctttta acaagaacag    28200
cctacccacc tctccttcac ttgtgatact gactttttga agcagtcagc ccaattgtca   28260
tctagaaggg cccacatttt aagatacata tttttagaga tggcgtgtca ctatgttgcc   28320
taggctggcc ttgaactcct ggcctcaagt aatcctcctg cctcagcctc ccaggtagct   28380
gggactacag gcttgtgcca ccacgactag ctggcccaca ttttagatgt ctctcttttc   28440
ttgtgatata atttaacttg tttgtccata tatattactt gtagacaaga agttaggtct   28500
acaggcatgt tcaggttaaa catttttgggc aagaatattt cataggcagt actgtgtact   28560
tcatatagca tcagctcacc aggcacttaa tggttggtta ccctgtggtt tgtgatgcta   28620
cgttttaaca cttgattaaa gaaggaggtg actgccaaat ctccccattg tagacataca   28680
gttttcctgt ggtaattgat atataatctg tgatgtgatg ctttggcacc atacaaatat   28740
cctattgccc aacagccatt tgcataatta ttttagcatt cattgatcct tgcctgaaac   28800
cattattaca ttgggggttg caaaatgata gttttttttaa ttgtcacctc ttctacattt   28860
agtactgtca ttcctctgta atgaattttc cctcatcaaa taaggaggca ttatatttcc   28920
tcctaaaaag acagtataga tgcttaatct ttgcctttat tacatttcag agtaaggagt   28980
tggtagaata atccacctca atggtggcaa aatatttgct gttgtgtttc cttttctctt   29040
tcatgtcaat atggactcat agggatttat ttattaaatg ttttacaatt caaattgggt   29100
caacaagagt cccttcatgt tggttcctat attctcctgg catacccctca ttaattagtc   29160
tttgagcaat ttcttgtttt ctggcacaag atattccatc ccaatatgtg cttttcgtgt   29220
cctagaactg attccaagga gctctggttc cttatagtgg caacggtatt tagaatccaa   29280
catgtgggta ctaaatgtgc tgattcttac tggggtaaca ttatatctag gcactttcag   29340
aggacatcgc tagaaaatat attcagtttt tatttttttat tttttaattt tttgtagaga   29400
caaggtctca ctatgttgcc caagctggtt tcgaactgag ctcaagcgat cctcccacct   29460
cagcctccca aagtgctggg attacatctg tcagggcaaa ctgctggtaa atattttcac   29520
aaaagaaaaa taaaaaaacc aaagtgctgg gattacagat gtgagccact gtgccctcca   29580
ttttttttttt aagtcataaa tacataatga tgtcttctat ggcaatttaa cattacaggg   29640
ttcttcctta actttttttt tttttttct tttttttgag gcagggtctt gctctattgc    29700
ccaggctgga gtggtgcagt ggtacaatcc taattcactg cagcttcaaa tgcctaggct   29760
tcaaacaatc ctcctccctc agcctcccga gtagctaaga ctacaggtgc atatcaccat   29820
gcccagctaa ttttttaaaaa ttttttgtag atatggggggg tctcgttgcg ttgcccaggc   29880
tggtctcgaa ctcctggcct caagtgatcc tcccatctcg atttcccaaa gtgctgggat   29940
tacaggtgtg agccaccatg cctggccaac ttttatttga tctgtatata tcttttcctt   30000
acactgaaaa tgttgggtct tactaatgtt aacatagtta cttatttgct ttatcttgta   30060
atagacataa aattacaaaa ttataatacc aatattacga taaatagctg ggcatggcgg   30120
cgctcgcctg tagtcccagc tactcaggaa gctgaggtgg agggactgct tgaacctaag   30180
agttgaagc tgcagtgagc tgtggttgtg ccactgtact cctacccgga caacagagtg    30240
agtgggggga aaaaaagaa ataatggaag atccagagaa agcccccaaat attttaaaaat   30300
taaacaatac acttgcagc ttcctcacct ctctcagcct tcatagaatt gaagagagtt    30360
agggccttgc actagattag gctttgcctt aaggaaatgt tgtgtttgat ttgatccttt    30420
atccagacca ttaaaacttc cttaacgttt attagtaata aggctattc actttcatat    30480
catttgtgtg ttcactggag tagcactttt agtttccttc aagaacttg attcacaact     30540
tggctaactt tggtacaaga ggcctagctt ttggcctttcc ggcttcaac atgcctctca   30600
ctaagcctga tcatttggtt tttggtttaa agagaaaagac atatgactct tccttttact   30660
tgaatgctta gaggccattg tagggttatt aattggccta atttcagtac tgtcttgtcc   30720
aagggaatag ggaggcccaa ggagagagag agagatgggg gaacagctga ttggtggagt   30780
agtcagaata tacacattta tcacttaagt tttgccatct tttcttttc ttttttcttt    30840
ttttttttga gacagtcttg ctctgtcacc caggctggca tgcagtggca tgatctcagt   30900
tcactgcaac ctctgcctcc tgggctcaag caattctcct gcctcaacct cccgagtagc   30960
tggtattaca agcgtgcgcc accataccca gctaatttttt atattttta gtagagacag   31020
ggtttgccat gttggccagg ctggtctcga attcctgacc tcaagtgatc cacccgcctt   31080
ggcctcccaa agtgcgggga ttacaggcgt aagccactgc cgcctggcca gtttgccac    31140
ctttttttat tttttttactt tttgagatgg agtctcactc catcacccag gctggagtgg   31200
agtgatgcaa tctcggctca ctgcagtctc tgcctcctgg attcaagcga ttctcctgcc   31260
tcagcctccc gagtagctgg gactacaggc atgtgccagc acgccagct tgttttttgt     31320
attttagta gagacggggt tcaccatgt tggccaggct ggtctccaac tcctgacctc      31380
aggtgatctg cccggctcag cctcccaaag tgctgggatt acaggcgtga gccacccgc     31440
ccggccaagt ttgccatctt ttatgggtgc agtttgtggt gccgcaaaat gatgatagta   31500
```

```
gtaacatcag agagcattga tcacagatca ccataacaaa tataataatg agaaatttga   31560
aacattgtga aaattaccaa aatgtgacga agacatgaag taagcacatg ctattggaaa   31620
aatggcactg gtaaacttgc ttgatgcagg gttgccacac accttcaatt tgttaaaaac   31680
tcagtatctg cgaagtacag taaagcaaag cacaatcaaa tgaggtgcgc ctgcatatta   31740
caaccaagag gcttttcgca gaaacacgag tgtgcttcaa cattcaaaaa tcagttggtg   31800
taattcacca cattaagata ataaggagg ccgggtgcgg tggctcacac ctgtaatccc   31860
agcactttca gaagccgagg tggacagatc acttgaggcc aggagtttga gagcagcctg   31920
gccaacatag tgaaatcctg tctctactaa aaatagaaaa attagccggg cagggtggca   31980
cgcacccttta gtcccagcta ttcgggaggc tgaggcaggt gaatccttga aaccaagagg   32040
cggaggttgc agtaagctga gatcacgcca atgcattcta gcctgggcaa cagtgagacc   32100
cagtatcaaa aaaaaaaaaa aaaaaaaaaa aagataataa aggagaaaaa ccatatagtc   32160
tattcaataa atacagaaaa cgcatctgac aaaattcagt gcccttttcat gataaaaatt   32220
cagcagatta gaaatagagg aagtgcatgt atgaaagagc tacagataga ttgtacttaa   32280
ttgtgaaata ttgaacatgt taccccgaaa atcaggaaaa aggcaaagat gtccactcta   32340
accacttcta ttcaacatta tactagaggt catagccagt ataatgaggc aagaaaaaac   32400
ataagaggca ttaatattta aaggaagtaa aactgtttct atttgtaggt aatgtcgaaa   32460
atgtgaaaga aactatcaga acctgctaga actaaaaagt gaattcagca aggtctcagg   32520
gtacgagatc attcaaaaac taatcagaaa tgaaatttca aatgcaatat cgttaggaac   32580
aatttaataa gaaatgtaca agattttacac gctgaaactg aaaatgttgc tgaaagaaat   32640
taaagaccta aataaatgga atgttgtacc atgttcatca gctgaaagac taagtgtctt   32700
tacagtgtca gttctcccctt cattgaactg tagattcata accccagtca taactgcagg   32760
gttttttttg tagaaattga ttgtaaaatg tatatggaag ctgggcacgg tggcttatgc   32820
ctgtaaacca gcactttggg aggctgaggc agacagatga cttgaggtca ggaatttgag   32880
accagcctgg ctaacatgac gaaaccccgt ctctacaaaa aatacaaaaa ttagccagac   32940
atggtggcac acacctgtaa tcccagctac ttgggaggct gaggcatgag aatcacttga   33000
acccgagggt ggaggttgca gtgagccaag atcatgccac tgcacgcccg cctgggcaac   33060
agagtgagac tttgcctcaa ataaataaat aaataaaacg tatatggaaa tgcaaaggac   33120
ctagaacatc caaagtaaac ttgaaagaga acaaaattaa ggggcttatg tgatgtgact   33180
ttatagtcat ttgattttta acagaggcac cagaacagtc cggtgcggga aaggaaagtc   33240
ttttagcacg tgccggatga tggcaaatga catccatacc agacaaaaat gaaccttgac   33300
cttaccctaa atattagttt cttagagttg ccacaaacta ggtggcttaa aaccacagaa   33360
atttggctgg gtgcgtggc tgacgcctgt aatcccggcc tttgggaggc cgagtcgggc   33420
agatcacctg aggtcaggag tgcaagacta gcctggccaa cgtggtgaaa ctttgtctct   33480
actaaaaata caaaaaactt agtcaggtgt agtggtgcac acatataatc ccagctagcc   33540
aggaggctga ggcaggagaa ttgcatgaac ctgggaggtt tgcactgagcc aagattgcac   33600
cactgcactc cagcctgggt gacagagtga gactccgtct caaaacaaaa ccacagaaat   33660
ttgctgtctc ataattccag agtctagaag tccaaaatca actgtcatca gggccatggt   33720
ctctgtgaaa cctgtagggg agtccttcct tgcctcttcc tagcttccag tggttggcaa   33780
cctttggcat tcttttgattt gcagctgcat tacttcaata tctgtcttcc tcatcacaca   33840
gcattctcca tgtatgtctc tgtctttaca tggcctcctt cttgtaagaa caacagtaat   33900
attggattgg ggcctgccct actccagtgt gacctcacct taactaatta cacctgcaac   33960
aacgctgttt ccaactaagg tctcagtgtg aggtactgag ggttaggact tcaacatatc   34020
tttttttggg gacatagtcc aacccatgac actacttcac accatacata aaaattaatt   34080
catgagagat tatagaccta aatgttttaa aagctaaaaa tataaagctt ctgcaagaaa   34140
acataggaga atatctgtgc agtccaaaga ataaggtttt ttttaaacac aatttcactc   34200
tgttgcccag gctggagtgc agtggtgcga tctcagctca ctgcaacctc tgcctcccga   34260
gttcaagcga ttcccatgcc tcagccttcc aagtagctgg gattacaggt gtgcgccaca   34320
atgcctggct aatttttgta ttttttagtag aggcagggtt ttgccatgtt ggccaggctg   34380
gtctcaaact cctgacctca agtgatctgc ctgcctcggc ctcccaaagt gctgggatta   34440
caggtatgag ccaccgtgcc aggccaaaaa aagatttatt aggatacatg aagcaatagc   34500
tattaaaaga aaaaataaat tggacttcat taaaatttaa aactttttggt cctcaaaaga   34560
taccattaag aaaatgaaaa gacagagctg ggcgtggtga ggcttgcctg tagtcactac   34620
tgggtacttg agaggctgag gcaggaggat cacttgagcc caggagttct aggcaacat   34680
aggcaatata gtgagacagt gtctcttaaa aaaaaaaga aaaagaaaaa acaaaagaaa   34740
ataggctgag agctgtggct catgcttgta atcccagcc tttgggagta caaggcagat   34800
ggattgcttg agctcaggag ttcaagacca gcctgggcaa cagtgaaatc ccatctctac   34860
aaaagataca aaaaattagc caaccatggt ggcgtgcacc cgtagtccat agtcccagct   34920
actcgggaag cagaggcagg aggattgctt gatcccaagg aggtcaaggc tgcagtgagc   34980
tgaggtcgcg ccaccgcacc ccagcctggg tgactgagtg agaccctgtc tcaaagaaaa   35040
tgaaaagaca agtccaccaa gaaaacagtt gagaccagtc atagaaaaaa tagaaagtca   35100
tatctgacaa aggatttgta ttcagaagaa ttcctataac tcggtaataa aaagacaacc   35160
tgattttttaa agggtgaaaa tattttaatg gatactttt tttttttttt tgagacagag   35220
tctcactgtg tcacctaggc tggagtgcag tggtgccatc atacatagct cactgcagac   35280
tcgaactcct gggctcaagt ggtcttcctg cctcagcctc ctgcgtagct aggactacaa   35340
gcacgtgcca ctatgcctgg ctaattttta aattttttgt agacatgggc tggtgtgtgt   35400
ctgtgttgtc taggctggtc ttgaactcct gggctcaagt gatcctccca cctctgcccc   35460
ccaaagtgct gggccaccac gcctggtgtg tgtcaccag agatgagcca ccatgccctg   35520
cctgatactt ttctttttatc atctgttttat ttcttgttta tgggtgtttc tgttctgatt   35580
ttatgactat tctgtatttct aagatttctc tgagaatatt atttgttttcc tctaaggaca   35640
gacttggtct ctcttccatg gggctggttc ttgagccgcc agggatgggg ggaggacctg   35700
ggtagctgct gcgctgcccc ttctctgctg tggtggagtg gcccgttgcc tgcggggtct   35760
gtctctgaag ggtggtttgg agaagttctg tggaggcgag gcaggggtca gctcttgccc   35820
catggaccct cagagactgg gaaaaggtag gcatcacctg ggctgctgcc agccacatca   35880
agagccttg gggtgggtgg ggtggggc gggaagggga aggttctagc tgttgattta   35940
gaaaagaccc attgatttct tgcctgaggg aagaagtggc accttgccac tccaagtttg   36000
ctctgctcac cagcccaac agcatcagcc tcacctggga gcttattgaa ggtgccctgc   36060
cccaaagctt gtgggtcggg atctggcagt cagcagcccc caggtgttgc acacatgaca   36120
gcactgcttg ccctcctct cgtctggtct ggtctggtct ggtctggtct ggtctgagag   36180
cttcctttggg gctctgacag gtatacaggc tctcatctgc tctacagctc tcttgtagta   36240
```

```
cattcctctc tgttccatta gtcaacatgt tcttgcctac ttccagcatc tagaaatttg    36300
ctgagtgtat cttatccgtt cagaggtcct ctcctgctat tgcctctgtt agaaatttct    36360
tccctttcat atgtctgtac ttcggttttct ttgaggtttg aagggtcaag tgcaattac    36420
atgtaggcag ttggccatcc tctggtgaag gctttaaagc ccaggaataa caagatccat    36480
tatgtctaaa actagcaaaa accctacctg tcacatgctg aactgaatta gaggtgatgg    36540
ggacagaagc cagattggag tgagtggaag gtgagggagt ggagattggg tatagacaac    36600
tctctttaag aagttttgtt gtgatggtga ccagaaaaat aggagtgggg tagaggggga    36660
tgagggtgtt tttcacgtgg gtgaaatatga gagcatgttt acatccttct gggaatggcc    36720
caggagagag gggagcgtga gaaggaggaa atggggacct ggaggagcag actccttgtg    36780
tggagggggg aagcggcatc tagagctgtt gcaggaggtg ggctttgagt aaatgcttcc    36840
tctttggtaa agacggggaa cgggaacggt agaagttgca cggacccttt gttaaagctc    36900
agaagctgag cgagaattag agcttaagtt tatggagtag tcagaataaa gtaccctaa    36960
ctgtattctt gcacagtgca ggaagccagg ggtctgaaat caagatgttg cagggctcca    37020
ttcccccag agcctctagc atggatcctt ccttgcctct tccagctttt ggtggctgcc    37080
tggcagtcct agactttcct tggcttgcag ttgcattgct ccattctctg cttgtgtctt    37140
cacatggcct tctctgtgtc cccgtattct tctctggatg cttgtcactg tattaggccc    37200
acccctaaatc caggatgatc tcatatcaag atccttcact taattacaga agcaaagacc    37260
ttccaaataa ggtcagagcc acagggtctg gggttaaga catacaccta actattcggg    37320
gctaccatcg aaccctgta gaagcctgtc catttccagg atagcagagc ccaaggaagg    37380
gccagagtc cccccaaaac agttgtttgc attcaccaga ttctaagcta taagcagatg    37440
ggcagtggca gtcggtccta atccatatac cattggcaac aatagtttag ttcactgtag    37500
acataatgag atgcttatct tctgctaagt agtcctcatg ataacagcca tattactcct    37560
ggctttgagt gacagcgctg tgctcttgtc tggtgcccat atacttcagc agctggaaac    37620
aagacagtgc tcatgattca ccggaaagtt tctgtagtta aaatcaagtg atcccttgag    37680
tctattctaa tatttgtctg taccatgttc tgtgacgaga catggaaaca aaacattaag    37740
aagtgaaagt atctttgatt atgctcttga agacaacttt ttgttttgtt gtttttgttg    37800
acgggagtt tcactcttgt tgcccaggct ggagtgcaat ggtgtgatct cggctcactg    37860
caacctccgc attcccgggt tcaagcgatt ctcctgcctc agcctcccaa gtagccagga    37920
ttacaggcat gcaccaccac gcctggctaa tttttttat tttagtagag acggggtttc    37980
accatgctag tcagactggt ctcaaactcc tgacctcagg tgatccgcct gcctctgcct    38040
cccaaagtgc cgggattaca ggtgtgagcc accgtgcctg gccgaagaca acttttttaaa    38100
gatgcatatg ctctgggctg ggtgtggtgg ctcacacctg taatcccagc actttgggag    38160
gccaaggcgg gcagatcacc tgaggtcagg ggttcaagac cagcctggcc aacatggtga    38220
aaccacgtct ctactaaaaag tataaaaatt agccgggtgt ggtggcgggt gcctgtaatc    38280
acagctactc aggaggctga ggcaggagaa tcgcttgaac cccagaggcg gaggttgcag    38340
tgaattgaga ctgtgccact gcactccagc ctgggcgaca gagtgagact tggtctcaat    38400
aaataaaata aaataaagat gcatatatgc tctgaaggct ggctacattt tattttttct    38460
caaacaactt ttacagtgga tagtgctgta aaagttgttt agctctggtc atttttatctt    38520
ttttgtgatc tgcaaaagga gatccttttc cttttcactg cctctaatac ccaactccaa    38580
tactcctttg acctcacagg cacttagaat ccatcagtgg ctccatcttt tctcagactt    38640
cacctccttc gtatccttat tcctctcctt tgtagcttca gtgccagtca gacgtcgtta    38700
ctccctggca cactacctca gcccttcggc acttttcttgc tttgttatat tcagtcgaca    38760
aagcccccagc ctcatgaaat tcagtcatgt ctgccccatg cctccgt cctgaagctg    38820
aatgtgactc cttcattgat tccccctttta agttcatgtc taccccaggt aaacttcttg    38880
ccgccaagcc cacctgcata ctgcagttcc ccggtctctc ctagcccctc ccaccctcct    38940
catcagctgt cacacctcct tgcagctgat atcttagttc ccagagagca cagaagcaag    39000
ctcaagagag tgtctacagg ccagcgtcta ctccttcgct ctgcctccct catgctgtca    39060
cggagcgcct gtcccaggcc ctcactcctg ttctaaggca tctctccagt cctctactgc    39120
actctcccccc atcagagatt cctccctcgc ctgccctaga aacttgttgc tacttctccc    39180
accttgacaa aagctgctcc caacccccca cctgtctagc atctctgttt tcctttacca    39240
gcaagactcc agtccctgtc tccacacct cttcaacctt ctccagttgt tccttttgca    39300
ccacagctct gccaagctgc tccatgaggt ctccagtgat gaccttcatg ttgttaaatc    39360
tgggagctgc ttgtcacttc ttttcccaga gctgtcgtcg tcagttaacc ccaatacccca    39420
tacgagacaa tccttccct cccttgagtc tctgcactga tgtgcacctt ctcagtgcaa    39480
accacagctt ttgtctcttt ctagctgaat acatgactga ctgtgcttat cttagctgtc    39540
accccctgctg gagcagaagc tccacaggac aggattgtct ccttgattca cagatgtagc    39600
tcaagctcct agaacagtgc ctggtgtctg tgggtcctca ggaagtccta ggtgagtgtg    39660
tgaatgtctg tcctcctcgg tcttttctgt ttcgcatgtg atgttggaag gcctcaggtt    39720
caggcttttc ttctccaccc tcactcccga agtgattccg tccagcctca tggctcccaa    39780
atttatgtct ccaggctgac tgggtcacgg gaactcctta tcctcccctag accttctctt    39840
tccctggtct tctcctttcc agtaaacagc aactccaact cctgctcctc aggccagaaa    39900
cctggcgctg gttacctcat tgttcacaa atactgttac tccacctgca agatggatac    39960
aaaatctcat gagttcccct gcctccatgg ccccacccct ggtccaggtg tccagcttcc    40020
ctgcctctgc ccttgcccc tgttctttg tttagtcctg caatattgtc ttcttctgtt    40080
cagaaccctc cagtgggtcc ctgcttgctc agagtcacag cccaacagga tcacctctct    40140
tgccactctc ccaccactca tgcactgcgg cctcactggc ctctggctc ctccctggac    40200
cctccaagta tgcccctgcc tcaaggcctt gacctctcct ctgccctctg tcccaggtat    40260
cacacatgtc tgctcaagtg tcaccttccc aatgtgactt tccccgagca caccatgtc    40320
tgtaagtcag gcagcctgcc tctgcccccac cagtccccca tgcctagcat aggacttgtc    40380
accatctgcc acaagctgtg ttactgcttg gttttgtttg tgctctccca ctcccttccc    40440
ctccctcct ctcccaccc ctatagaatc tgagtcccat gaggacagag atttttttt    40500
ttgcctcttc tcaatatat ccccagtgcc tagaatcatg catattttaa tttattgagt    40560
gaattaacaa ataaatttctg cagtgggaca ttgctctaag gttttgtctt ataagaggga    40620
cagaagaaca tgcagcctgc tctgctgttg gctccttagc ttccatgg ctaacaggaa    40680
caatattgtt tatgagataa tcaaagccat agtcatgagt tagaaggtac atataaaggc    40740
aaaatatgtgg agattgagtt actttggcgg gggcggaggg gtgtgtagtt atctgaaaac    40800
atggaacaaa tcaatgagag tctaaatagc acccacatat tgccctctct tttaaaacat    40860
acctcctta tgagtgtaga atttaacagc acagtttccc agtgcagctt tgcgaaacaa    40920
gagaaatgaa ttttaaaggc tgtcaggtgc cttttgcaatc tgtggcttag tatttgtgta    40980
```

```
acaacatttg tgttttgcca acagatgtac tgcttaaagt acccatgaga atggcctctg    41040
tggttttcta ctttctcgga tggaaccttg ggaactgatt attgagaaga ggctgatact    41100
gcccacctca gctcccaggc aggcttcagg gccttggtta ctactccttt gggccctcac    41160
tgacccttgc agacgtcttt tgcaacctct gtagccagaa gagacaactg ctttctggca    41220
tgttgctctt tccctaatgg ctttatgagc ttcttgaaca ccaaagcctg tgtgacttcc    41280
tcacgccttc ccctgtatag tatagcaccc ctaactgtat gtgtaaggag aaggagtgag    41340
caattgatgg cgtccccctg gatctccaag ggaatgggaa ggggcagggt ttctggattc    41400
agtcatgtgg aatctggtcg ttggtgtcta aatgtgcctg ttacttgtgc ccaatgtcca    41460
ggttcaccag gaggcttagc ctgctcattt ccctgctagt agctatattt tgggagagca    41520
tttttttatgc tctaattgaa ctttgtgggt ctcagcaatt tgaacaatgt tttgttttc    41580
ttctggtcag gttacaaagg aaagaaaagg aatctggtgt tgtaggaggt ggtgtgttgt    41640
gtaattactt gttttttttt tttaagtttt tttatatttt tgcaacaagg caagttttct    41700
ttgaataaat aatgctggga gcttatcaca tagaaggcat atgtgttgta ctcagtacat    41760
tctgaattat ctgggtttat ttttatctct tgaattcact tataaacaat tcaaaggctg    41820
cttttttagc taacagaaat aggaagagaa tctcagaatc tgtttttgtca tttttttcaat    41880
gggttgagtt atagtgatta tgctaactcg gtggaaaagc agtgtagtga gtaaaccca    41940
catacgcat atcatgaaca ttttgttgct ttttggctt ctgaccatgt tcatacctttt    42000
ttttgtgtta aaagtctccc cattgtgtat atcttagtaa gaggcaggtg gaccctagtt    42060
tctacctaag aaaacctgaa gatggggttg ggggcctgtg gtgtacttcc ttctcatgct    42120
gtccatgacc actgcagtgg cttttgtaagg atccaggacc cagggcccct cagtgggtgt    42180
cttccatttc tcaagattgc ctcttggttg tgagatgacg gttgctgctc tagtcattgc    42240
atccactcct ccaggtagga agaaagaggt cataggggaa aggcaaaatg gcacttgaca    42300
tcttaacttc taggcccatt caatatttcc atttccatct tcacacccat catcttgtcc    42360
tagggaacaa acagcaccag cagctcagta gctataacag caattattat ttctcacaca    42420
tgggtctggg tcagctgcaa gatgggattc agatctgttc tcaagcctgt cgttccagga    42480
cccagggaa agaagcagct gccagggaga gtctcttcgt aggcggaggt caggagtcca    42540
agaggagtga gcagagtcac agaagcctct taaagcctct tcttccccca tcccatcaac    42600
acgtgagcaa gcccagagtc agtgggtggg aggtgtgctc cgcccatagt cagtagaaca    42660
agagcaagct tgaaagagaa cgatgaacag gagtgcactc ggccactgtc tccttagcca    42720
taacgtagtc ccatggtctg ctgggaagcg gggaataact ctccttagct gagcgcaggg    42780
tctcattagt aaggcagatg gagaacatgg atgttggggg acaactggca gtgcctgcca    42840
caggggaatg gatatattcc ctcccccttgc tctctggaaa ctaggggatg gcgatgaagc    42900
ctaggtttgg ccaaacccat tctgccttca gggactttga ctcttgaggg acagtgaggg    42960
attagtcatg gtggtggcag ttgagtcaca aaaccagcag tggtggctaa tgtccagtga    43020
tgacatgcaa cagtgcccag ggtgggtgtc ccaaccagca ggtccctgca gtataacctt    43080
ggctgtgttt gcagtggtgc agcctctatt cctgctgctt ttctgagcct agttctctag    43140
ttctctctcc atttccagat ctgctgccca agaactcctt tgtgattgaa tttaaccaga    43200
gttgatttct gttgcttgaa actcaggacc ttgatgcagt gtgcagggtc tgggcaaggt    43260
aaaaacacac tttcatgatt tcgcctcaag tatagtagat gagcttaggc tttttgagcc    43320
aggtagcctt gggattaatt ctcagctctt gcacctagca ggtgacctca gcaatcaagt    43380
cacttgccct ccttgagcct cagtgttgcc ctcagttaaa cattgctctc gtgtgttgct    43440
gagcattcag tgagattgta tataaagtga tcattgtgaa ggtattggga cataaatttgg    43500
gaaagcgtcc tggtctaagc ttttgattgg ctctccatca tttgggtaat gggatagtga    43560
tttaggagta tcatagcagc tcaagggccc ttctggaaa gggtatgagg aaggtcaggg    43620
acaagtctga aatgaatcat cctaggctta atgcctgtga ctgggcagtg ggtacaatta    43680
tctcaggcta gtcagtagtc atttattgtg agaatacatg ggcagatttt ttaatttcct    43740
tctcagtcta gacttgaatg caaacagttc ttattgctaa cttaccacta gtcaccacta    43800
atgaacaaag actatgaaca ggaaattcat aaaagaagag atacagatgg ccaatgaaga    43860
taggaaaaga gttctgcctg ctggtaatca aagagatgca aacgagaaca aaaatgatgc    43920
cttttcacct accaaatttg tcaagattaa aaagaaagca aagagccagc gtcagctgat    43980
gttcatacct gcacctgctc ggtagcttgc taatgttcct cctgctccac acgccaggcc    44040
agcctccacg cgcagccag gtgaggcctt tccttgtata caggcacgtt tggattcact    44100
gttgcataag tgagacatgt gcatgcttca caattcagga agtgcaaact ccagagtgat    44160
gcaaggtctg agtgtccctg ctgccctggt ctcccagctg cctaggcctc tcttcaggga    44220
acggctgcat cagggtctt gtctgtgtct tttgaggtgt tctatgtaca cgcagacaca    44280
tctaaaccta ttttatttt ccctgcacct gcttgggcta ctgtaagctg ttaaattttt    44340
ttttctagga atttgtccat tttgtctgac tagcataaag ttgttcatgt tatagtttat    44400
acatttgcaa catctgtaat tatgtctgct ttttcattcc tagtgtttgt tgtttacttg    44460
taccttctcc cgtttttcct tgtcttggta aaagctcatt aggttcattg gtcttacaag    44520
aagcagacat gtaggcatta ttgccctgta ttactctgtg tctcttttct agttcattaa    44580
attctgcttt tgctttttatc tttattattt tttctatggt cttagagtac attctctgtg    44640
ttttgttgtt gttgttgttg ttgtttgttt ttgttttga gagagagagt cttgctctgt    44700
cgcccaggct ggagtgcagt agtgcaatct cagctcactg caacctccac ctcctgggtt    44760
caagtgattc tcgtgcctca acctcccgag tagctgagat ttacaggcat ttgcccacca    44820
cccggcaaat ttttttgtatt tttagtagag atgggggtttt ggcatgttga ccaggcgggt    44880
ctcgaactgc tgacgccagg tgctccaccc gccttggcct cccaaagtgc tgggattaca    44940
ggcatgagcc accacgcctg gcctaactt cttaagttat aaatttggtt cattgatttt    45000
tctaccctttt tttcaaatgt aaacatttaa ggctaaccct ctggaactac ttcaactgta    45060
tctagcaagt tctgatagta ttgtcacttt aagttagccc aaagatattt taaattttct    45120
ttgtttcttc ctttgactca catattattt taaaatgtgt ttttcaattt ccaagcacat    45180
ggctttgggt ttgttttttt ttttttcctag ttgctctaga aaaaaaaatt gactgcatga    45240
ggtggctcat gcctgtaatc ccagcacttt gggaggccga ggcggcagaa tcacctgagg    45300
tcaggagttc gagaccagcc tggccaacat gccaaaacct cgtctctact aaaaatacaa    45360
aattagccgg gcatggtggc acacacctgt agttccagct actgggaggc tgaggcagg    45420
agaatcactt gaaccgggag gcagtggtca cagtgagcca agattgtgcc agtgtactcc    45480
agcctgggca acaagagcaa tactccgtct caaaaaaaaa aaagaaaaaa agaaaaaatc    45540
aacttctaac taaatggcac tgtgatcaaa gaacttggtc tgtgtgacac cagttcttgc    45600
agttggttga gaagtgctcc atgacacatt atccacaacc agtggacaga atatgtcacc    45660
accaagcatg ggtgcaggat tctacatata ttcattacct ctgtcttatc cgtttgttgt    45720
```

```
gaaagtattt tctcttctta ctgtcatttt gtttacttga tttatcaact gatggaatac   45780
gtgttaaaac ctactgtggt gatggacaca tcagtttctc cacagagttt ggtcattttc   45840
attttattat ttattttgag gccacatttt cagtttaga tacagtttca cattcctggt    45900
gtattgaacc ctttggtatt atgaagcgac catactaata tgttattttt ttttaaatta   45960
ttatttattt tatttatttt tcttctttt ttttttttt gagacagggt ctccctctgt     46020
cacccagtct ggagtgcagt ggtgcaatct cagctcactg caacctccgc ctcctgggct   46080
caagtggtcc tcccacctca gcctcctgag tagctgggat tacaggcttg caccagcgcg   46140
cctggctaag ttttgtatt tttagtagag acagggtttt gccatgttgc ccagactggt    46200
ctcaaactcc tgggctcaag cagttcacca gccttggcct ctaaaagtgt tgggattaca   46260
ggtgtgagcc accacgcccg gccatcccag tttttattt tcctcctttc tgtgtcttta    46320
tgcatcagtg aggtggagct tttgaaaatg tcagatagct agattttttt ttttgagac    46380
ggagtttgc tcttgttgcc caggctggag tgcaatggcg tgatctcggc tcactgcaac    46440
ctccacctcc caggttcaaa acaattctcc tgccgcagcc tcctgagtag ctgggactac   46500
aggcacgtgc caccacaccc ggctaatttt gtattttag tagagatgtg gtttcaccat    46560
gttggccagg ctggtctcaa actcctcacc tcagctgatc cccgcctca gcctcccaaa     46620
gtgttggaat tacagacgtg agccaccatg cccagctgat agctagattt ttttttttt    46680
tttttttttg agacggagtc ttgctctgtc gcccaggctg gagtgcggtg gcgcgatctc   46740
ggctcactgc aagctccgcc cccgggttc atgccattct cctgcttcag cctccagagt    46800
agctgggact acaggtgccc gccaccacg gtgggctgatt tttttttttt ttttttttt    46860
gtattttag tagagacggg gtttcaccgt gtcagccagg atggtctcga tctcctgacc    46920
tcgtgatccg cccgcctcag cctcccaaag tgctgggatt acaggcgtga gccaccgcac   46980
ccggcctcga gatttttaa aaaatcatt gtctgttttg tcctttaaca tctatttgat     47040
ttctgatgta tttagattca tttatagcat atttgtgcat tctatttttc catatttct    47100
gttcttttaa atttttcctc tcctttcttg ccttctctta gacttttaaa aaaattgtag   47160
taaaatacac atcacctaaa atttaccatt tttaaatgta cagttcagtg gcattaaata   47220
caaattggag gccaggcatg gtggctcatg cctggaatcc cagcactttg agaggctgga   47280
gtgggaggat tgcttgaacc tggaggtcga ggttgcagtg aggtgtgatc acactactgc   47340
tatagcccag gcaacagagt gagaacctat ctaaaaaaac aaacaaacaa acaaacaaac   47400
agattggcat cacacagtgt gtgtgctgct gtgctgtgct gttatcattt aacattaaaa   47460
cataaacatc acactgttta tggactgaat gttttgtgtcc cccaaaattc cagtgttgaa   47520
gctcaaacct ccaatgtgat gttatttgga gatggggtat ttgagaggtg gttaggttta   47580
gatgaaatca ggagggaggg tgggtttcgc atgatgagat tagtgtcctt ataacaagag   47640
acagcagaga gcttgctttc tccaccatgt gagtatgcaa tgagaaggca gccatctcca   47700
agtcagaaag agagccctca ccaggggctg aatgtgctga caccttgatc ttggacttct   47760
agcctccaga actgtgagaa atttcagttg aataggcccc ccagtctgta ctatttgtt    47820
atagcttgag cagactaata cacccatgtt atgaaaagct ataaacatcc ctttaaaggc   47880
cacctaacgc gtcgtattac ctcatgcatc ttctctgctg agctttccaa aagagtggct   47940
taggctgggc ctggtggctc atgcctgtaa tcccagcact tgggaggcc aaggcaggtg    48000
gatcacctga ggtcaggagt tcaagaccag cctgaccaac atggagaaat cccgtcccta   48060
ctaaaaatac aaaaattagct gggcgtggtg gcgcatgcct gtaatcccag ctacttggga   48120
ggctgagcca ggagaatcac ttgaacctgg gagatggagg gtgcagtgag ccgagatcgt   48180
gccattgcat tccagcccgg ccaacaagag cgaaactcca tctcaaaaaa aaagagtggc   48240
tggccgggcg cagtggctca cgcctgtaat ccccgcactt tgggaggccg aggtgggtgg   48300
atcacgaggt caggagttca aaaccagcct ggccgagatg gtgaaacccc gtctctacta   48360
aaaatagaaa aactagccag gcgcagtggc aggcgcctgt aatcccagct acttgggtgg   48420
ctgaggcagg agaatcgctt gaacctgggg ggcggaggtt gcagtgagcc aagatggtgc   48480
cactgcactc cagcctgggt gacacagtga gaccccgtct caaaaaaaaa aaaaaaaaaa   48540
aaaaaagtgg cgtatgttcc cggtctccac ctctcattcg ccagcccctg tgaccaaacc   48600
cctgggatta gatctccatc gggtccctcc cctcacccta acctcacatg cagtggttcc   48660
tgagaagctg ctgtttatct gatcacggga tccagcagga tctgagggct cattcactga   48720
atctgtacta cccaacaagg caggcttgtc cttacccaca cttttcaggt gaaaacttaa   48780
tcagattcaa gcgtttatct tagtggcctc ttcgtggtgt gtgatttcct tcttgcagct   48840
ctttactggc taaaactctt cactgggagt taaaccaggt gtggtccttg accctcatca   48900
ttttgtccca tctcctatgc tgggctctgt atccttgtct ccaagcagtc tcgtgtgaca   48960
gggaagttac ctattattgt atggtcccct cttcttgtca cctctggtgt ggcacttgtt   49020
ccatttcttg ttcaatgaat gtgatttgtg aatgtgccac atctgtggga ggaaggcagt   49080
tcgcagcaag agttgtagtt cccttgcttt gccctgaggg ccaggacttt acactagatt   49140
tttttgttgc attcctgcac tcataaagta cacgtaaact tagaggtggt gtgttaaatg   49200
ctagaactta aaactgagtt cagctaggct caagtgcccc acaattttg tccaccaga    49260
caatttcatg aatatctaca gattgttccc tcaatatgcc tcaatattgg gcatattga    49320
tttgggagc acagacaagt caaggttgat gtgcatccgc tgaacatgat cttaagttgt   49380
tgaagtaggt attattaatg aacgaacgtc tattttagct ccaagagccc ctggtcttcc   49440
agaagagact cccaatgatc ttccagaagc agctgggctt cttttggtcc tcccccaccc   49500
aggtgcagtc ccgttctccc tgcctgggtg agtttgattc tctgccgtg gaatagccta    49560
ggctgctacc tcttgagcct cttccaccag gccatccatt aggtggcgac agagagcact   49620
aaaaggaact actatggaaa taaaacttgt tttgcttctt ggggggaaaa aaaagaaaa    49680
aggcttgtgg ggcgtgtgtg catttttagtc agattttact gtgcaaaaca tttgagagat   49740
ttctgccctc tttctccctt ccattcttct caacccactg ggcgccctac caccccgtc    49800
tccttcaaga taaggtagat cagaagacca aatagacaaa tgccatgtcc actgtttct    49860
gtcacagttg atagccatac cagtcaccca agctggaaac ccaacaggcc cctgcccttc   49920
actgcccaca tccaagggag ccaccaagtc ccacaaattg ttcctttaac tgtttgtccc   49980
tcttttgtct tctgtcatcc cttctaccgc tgtcctggtt caatccctca tcttgctctg   50040
ggactcccat gataacttat gatctttcct ccacctctct atcttccaca caatcccat    50100
catcaatctc attccccttg tttaaaccca agagtggcac cctgtgtttg agtgacatca   50160
gggccctca tgtggctcct gcttctcttt gtggcccctt ctgttgctgc tgcttttctt    50220
atggacatag ccctcagcag tccaggactg cttgtagttc ctccaggta ccatgttcct    50280
tgcactcctg gcctttgtca ttggctcccc tgcccaagtc cccttctctt ctcctttcct   50340
tccctgtgtg ccttgcttg tcgtgcttat ccttgaagac cctgtcaggt atctcttccc    50400
caaagagccc tgcctaacca ccgccccct ccccccgcg acacacacac ctgggttagg    50460
```

```
ccctgcctct ccacgcctgt gcctcctgcc aagtcctcag aggtctctga tcccatgtgc  50520
ctccaggcat ggcataggqg gactgtgaca cagcctctcg gcccacagac ccctgattgt  50580
gggcttgctc actgccccag tcagtcctct tattgaggat tccgtgccag ttcctgactc  50640
cagcacacac acgcatgtag gccgcctcc tagtgcctgg ctccttccct gtctcttctg  50700
ccactcattc ccatggtcgt atcctggagt tggtcatctc tggaactcca cccacggagt  50760
tctaacttag ctctgcctat gatgaggact tactgtcttc ccagcttgca gtgtcaacca  50820
ctgtttgatg cccctgggac tccattggtc ttccctcctc ttgtgaactg tgcccatcac  50880
cagacgaact tgttttagaa tttaccatcg taactgagct cccttcagcg catacctcct  50940
tggctcctgc tcagtctctg ttttctccttt tagccaaact ctctaagagt tctctccact  51000
catgggccct cttccttgcc tgctgctcct tgctcagctt gctccatgaa cacttgcttt  51060
tccacattcc atgaaataat cttaacagtc atcagtggct gtcactcctt ctcagccctt  51120
tccttgtgtc tcttctggta cctcatactc tccaggtggc catctcacct cacatcttga  51180
accctctggg tttgggagaa ttctcacctc acgagttgat gggaggcctg gcgacctctg  51240
attgtagtca ctgcaaatgc cagatgctta tttgcctagc ttccctttcg gtcagggcag  51300
cagttggcaa acggtatctc aagggccaag tccggcccac tgcctgtttt cgtaaatgaa  51360
gctttaccag gacccagttc caccccgtcc tttgtgcatt gtccaagact gctctcctgt  51420
acaacagcag gtgggctggt tgtgacagat actgtctggc ccacaaggtg gaaaatacta  51480
tctggcccct tacagaaaga aattacctga gttctacacg agggtgtagg tatgtacccct  51540
ggcctctgcc agtcagactc acatgctagg aggagcaggg ccaggcagga gagccgtgtc  51600
tcctggcatt ggggctgcag gaaagacgag ctccctaggcc acagtgccag tggccagtgc  51660
tgctgccttg cagggtcgca caggcagtgc tggctgtttg gactggcttg gcagaaggat  51720
ttgaagtatt gttcctagcc aactggactc aaacctgttc ctccaaccct ctagggattc  51780
tcttatcacc cagtagcctt ttcccccctag ttttaaaat tgcagtaaaa tacacaaaag  51840
ataaaatgta ctgccttaac catttttaag tgtacaattc tgtggtattg agcacattta  51900
tattgtgcaa ccatcaccac atgcatcttc aatagctttt catcagtcct tgtctgcata  51960
aatcagctag agttggtttc tattgattgc caccaataat cttgacagat atgtctgatc  52020
ttccttctct gcactgactc tctctttctctc gtctcctctg ctgattcttt ctcctcatca  52080
caactccaaa tagcaggggg agggttgttt acacttatat tcagcacgcc ctcacgcact  52140
cgcctggctc ttcagacctc tcccctgaac tccagattca tacatccagc tgcccttttag  52200
gcctctagaa agctaaatac ctcagtatca aaaacatgag aaacggaagc cagagtcctg  52260
gatctctcgc cctttcgctg tcccggtgcc catgccctcc agggatggca cctagaccag  52320
ctccctgcat ccctgcctag actctgcagt agtctcacgt ggcagacccg gaggtcactc  52380
tcctctctgg atgccctgcg gacactccgg ttagcctcag ctgcaagagc ctcctcaccc  52440
aaggtcacgc catttccagg acagccaccct ggtgactgag cgaggtaagg gtacaaggcc  52500
cttataggggc cttctctttg acttcttccc acctccctttt atggatgtca gttcctgatg  52560
aacatcttac acctcaaacc gtgacccaac atctgcttct gcagagcccc cctgtggcat  52620
cttgtgcccct cctgccccac tccctctact ctatatcttc ccatagttag aatgggcttt  52680
tttttttttt ttttgagata aggtctccct ttgtcaccca ggctggaatg caatggcaca  52740
gtcacgactc actgcagcct caacctcctg ggctcaagca gtcctcccac ctcagcctcc  52800
caagtagctg agactacagg tatgcaccac cacacctggc taattttttat attttttgta  52860
gagactgggg tctcccctatg ttgccgggggc tggtctcgaa ctcccaggct caagcaatcc  52920
tcccgccttg gcctcccaaa atgcaggatt acaggcgtgt accagtgtgc ccagcctcag  52980
atgggctctt tgaaaatgt ttattagatc aggttactcc cttgagaaaa acctctcag  53040
aataaaaccc gaagtccatt acttgaaagc agagccagct tcatgggcct ttgtaactgc  53100
ccatgggctt gctggaaccc aggcttgtt taatactcta ctctcaccat ctcaaaattc  53160
ttaattttttg aacaagaggc cctgcatttt cattttgcac caggctccac aaattgtgta  53220
actgggctgg cctcagcagc cacatggaac atgatccctc cttgcctatt tgagctcatt  53280
ctctaccatt ctctcccttg ctcacctggc tcccactcct cttgctcttc ctggaacttg  53340
ccataatgtt gctagagtca gagccttggc tcttgctgct cctcattggc tggacccctc  53400
tttacttgac ctgctccctc accactcact tccttcagat ctgtgttcag atttcgtctt  53460
ctcagagagg ctttttggcc ctgtccatct ctctgaatt acctctgacc tctccccccac  53520
caccactgcg ctaagctgcc tcagaacttt gtagacattc tgtctggtct tctgatgttt  53580
cccccttgga agaatcccaa ggtgctgaa gaatgctttc ttttatccttg aagttgagta  53640
ggttgactag agtctggctt gctattgagc attcttttatc aaattgtcct gggaacatgg  53700
tgtattcttt cagtctgcag atgtagtcgt tgctgttttca ggtcagctct cttatggatc  53760
tttgacagca tcttctgttc catttgttga gttctgtact tcagggacac aaattcctca  53820
tgttggattg tctttgtctc tcttccaatg ctattagctt tgccgtaatt ggtttagctt  53880
ttgtcttttt catctgcatt cactttgtct aatttgattt tcagctatgt atattctgtt  53940
tctggctgtt tttcaatgta tttattagtt tcataatgat gtgttttggt ctgcagtttg  54000
tttctctaga ttggaaattt gtcttttcat cttattctgt tttatcatcc catctttgaa  54060
ctctttatt gggaacatgt tcttatgaag ttgtgggggaa ttttttttccc ttccttgtgt  54120
attctcttct tggtggggaga ctttgccttt ctcgtgccat ctccctccct gggcctcttt  54180
tttttcttct ggccataata tgtttgccta gttaccatgt cacttctttt cgtcttggct  54240
caggcttgga tggctctgca tagtcgttcct gtttgcttttg agacagtgga ggaattcttg  54300
gctctctctt cccagtttct tggcatcttc tcttgctgtt ttcccctctg agctatcgcg  54360
tgcaggcttg ttatcttgta tccggagaga atttgcacgc tggagggagc tgcagccatg  54420
tagtcttcag ccctatctgg attcttctct ttgttctaag aactgtgttg gatgtcttac  54480
taaggctcac tctagctgca cgagggatgt gtgtgccatt tccatgggga taggggggcac  54540
ctcagtctct gggtggttcc ataatctgtg tatacctaag agcagtttgct tcccacagag  54600
ctgggctggc tcactgggca ctttgccatt tctcctgcac ctcccagctg gagtttctgg  54660
gtctaaaagg aaaaagtgaa ggactcccac ttggttgctt ctctccagct tactgactgc  54720
aaattcccag ggcgttgccc gctccctagg gtggtttctg ggggacgggg caggagcctg  54780
gctttgctgc tgctttgtcc tctggagtct tttctcgac tgctttgaat tacaccccttt  54840
tcctttgtgt gctgaaatct tccctcaca ctctccttcc ctgcctttct tttgtgtctt  54900
atcttactag gactggaaga gggcagttgt gcaggaggtc tgcatctaat tccctaatcc  54960
atgtgagagt gctcctgttg tgtgcttgt gacatgatgg tgagaaatac tccctagagc  55020
agtggctacc agaaggaagc catccccccc cctgcacaca cacacacaca cacacacaca  55080
cacacacaca cacacacaca ctccttctgg ctgtcctcag atgcctattc taggtaaatg  55140
tcagattcca agaaaatcc agttgagatc ttttttctt ttttgagacg agagtcttgc  55200
```

```
tgtgttgccc aggctggagt gcagtggcac aatctcggct cactgtaacc tccgcctcct   55260
gggttcaagc gattctcctg cctcagcctc ccaagtagct gggactacag gcgcgcacca   55320
ccacaccagg ctaaaatttt tttgtatttt tagtagagac agggtttcac tgtgttggcc   55380
aggctggtct cgaactcctg acctcgtgtt ctgcccgcct cagcctccca gagtgctggg   55440
attacaggct tgagccatcg cgcccggcct ccagttggga tcttgactgg aatgactggt   55500
gttcaatcat tatagtttcc acctaatttg tatttgtaca caggacagtt actaatttgt   55560
tggtactgt ttgatcccca gtccctagag ttgtttatgg ggtggagctt cagtccctgc   55620
tgcttcccct gtggcagcag ctggagtcag ggtggggacc cagggtgctg ctggcagatt   55680
cttgagacag gtagaatctc ctctatattg gtgtctctct ctgtcccagc agtgcccagg   55740
aaaacctggc cagcctgtca ctgacctctc cacctagggc actggtggtt caggtccttc   55800
tatttgccac cggcaaaccg tacttctgcc agtctggctc ttaggcccag tttctctgat   55860
cttgcagatt ttcttgggct ctgctacgga atcctcatac ctccggcagg tccctccttt   55920
gcccatgtgt ttaactgtgg tggaatcgtg tgagagctgc ttctctcgca tggatcccag   55980
ccacaccaca ttctacagcg gttcctctga aggcattgat agagatattt cctcctgttc   56040
tgcatttcgt tggtcatttc agtagaatca gggtgaaata aacatggggg ctcagatgtc   56100
agcattacga accaagtacg tcaggcaggc tgatgtggac tgacctacac tagtgagacg   56160
caagatgacg aaaacaaggg cactcactcc aagttactga tgagatgttt ggatcaaatg   56220
agccagtcct taagcagagt tctctagtaa aagagatctc cttctgccc tttcttgttc   56280
cccaaaatgt gttgccttca tggtgaaaat ttatttggc agattttctc ttctttgata   56340
aaagcagcca acacttgtt aaagtctgt gaaacttatt tacatgaagt atgtaaaggt   56400
aagaaaaaaa cattatcaac aagaaatgga gaaagccagc agctgaggac agaaaagtca   56460
tgcacagtgt cagtgtctat ggaaacaggc cacttggacc ttgaggacta ggtatttgga   56520
attggaggtg agcttggcct ggtgagtctc taaccacttg tgtgtaggat cagtgtgaga   56580
accctgctag aatatagtgg cagagatgca agggaaatc attggagaag ttaccaggga   56640
atgatgagct aatctgaaaa aaatacatgt ttctaagttg ggcgtggtag ctcatctgta   56700
gtcccagcta cttgagagcc tgaggcagga ggatcgcttg agcccagcct gggcagcaca   56760
gcgagaccct atctccctaa aaaaaacttt ttcgttgttt agttttggga ttttttttt   56820
tcctggtctt ttttcccct ttttgtgaat aacgggatct cactatgttg cccaggcaga   56880
tctcgaactc ctgggcccaa gcaatcctcc tgcctctgcc ttcctaagat tacaggtatg   56940
agccactgtg ttaagcaaaa aaacttttttt aaatgaaaat catttttaaa aagacaggct   57000
ttccagggga gggtattatt ccacttatat gaagtgtcaa cagtaggcag atttgtggag   57060
acaaatagat tagtggttac caggggctga gaggagtggg agtggggagc aactgcttaa   57120
tgggtaaagg gttgtctttg gaactagaga gtagtgatgg tcgcatgaca ttgtgaatgt   57180
actaaatgct attaatgata aattttatgt tatgtgtatt ttaccacaat taaaaaaaaaa   57240
agatcaaatg tcctcagaat agccaacaac cttccacttg gctaaatgcc tactcattaa   57300
acttcttgaa ctaaattcct ttctgattgt catggttatt gtgtcctggg cttcagagtt   57360
tcacattcag gttggcttgg tccagtctgt catgtatcac tataggtccc cacattggcc   57420
tcttcctcag acggacagcc catctatctg ccggggctct gtgccacagc cagatagact   57480
tgctctgaga cagctgtgtg ggctctgagc actggccagg catcacaaaa cctatcttta   57540
tgatttagaa taattggtgg tcagctgctg ttttaatgtt gttgttttt ttaatttaga   57600
tataattcac ataccatgaa atttactcat ttaaagtgta caattcattc ttcagtataa   57660
ttcataggct cacagaaaaa attgtttaaa aataaaatgt gcaattcagt gtcttttagt   57720
acattcacag agttgtgcaa ccatcgcctc tgtgtcattc caacaactt tcagcaccca   57780
aaagaaaccc cagacacagg agcagtcacc tcttattacc cgcagcccct ggcaacaact   57840
catccacttc ctgtctctat ggatttgcct attctggaca tttcctataa atggaattat   57900
gcactatttg gccttttgtg tctggcctct ttcactgagc gtaatgtcct caaggttcat   57960
ctgcattgta gcatgtgtca gaatttctt ccttttgag gctgaatgat attatatcct   58020
atagataatg aggttttgat tatccaccca tcccttggga atgcatattt gggttgcccc   58080
caccatttgg ctgttgtaaa ctgtgctgcc atgaacactg gtgtacggat atctgtttgg   58140
ttactggttt tggttttttg tttgtttgtt ttggtttttt gagacaaggt cttgctctgt   58200
cgcccaggct ggattacagt ggcacgatct ctgctcactg caacctccac ctcccaggtt   58260
caagcaattc tcctgcctca gtctcctgag tagctgggac tacaggtagc actcaccacc   58320
atgcccggct aaattttttt gtatttttag tagagacaag gtttcgccat attggccagg   58380
ctggtctcaa actcctgacc tcaggtgatc caccacctc agcctcccaa agtgctggga   58440
ttacagacgt gagccaccgc acccggcata gtttgtgctt tttgagagtg tatggctagg   58500
agtaaaattg ccaggtcata tggtaactcc atgtttaaca tttgagaaac tgccaaactg   58560
ttctccacag caggaatttt ttaacctgta tgtggtgggc ttgtgtttcg gttttcattt   58620
tacacatcta taaagatgag atttgctgta tggcactggt tgcctgtatt tggggagggt   58680
tctgcttttg gttggcaaga actgcatttt atttaagctt agcaaaacat aactggtttc   58740
tcgcatcttc tcaaaagtgg aggattaaga aatggactgc gaattcagag cagggcagct   58800
gaacctcagg ctccacccct gtagccttca agctgaacct cattctctct tgctcccctgg  58860
agaccactga gacactctgc ctgtgccagt ttgatttctc acatttttaa agggccaaag   58920
cttgtgtctc aaagtgctat agcctttatt gattcatgca gagaagcctc cttgattccg   58980
taattctgca gctaatactg gaagtagaaa gaattgaaaa caccatctgg atgacacttt   59040
agggtggaag cagccagtac aaggggggc tcattatttc ctctggtccc agactgttca   59100
cctggagctg tagccaccac cctgcccttta ggttaactgc ctcgagtggt agtttagctc   59160
tttgtgctgt gccgagggat aactggaagt gaaaggtgct gagaaatgcc atctcctgaa   59220
agtggcgagc atgagtgaat ttacgaaagg ttgggatatt gctgggctc tggaagtttc   59280
tctggagctc actccagggg acagggaggg ggctggattc caattcaagt gaaaaatacc   59340
tttcatctgc cttgttcacc tggctttttt gccttttgt aaaatctgaa aacctcaggg   59400
attgagtagt ctttccttaa ctgcagttgc ctgtctggcc acacctgcca gctgttgctt   59460
gtaccctgtg aatttgcacg gccttccggg ccttctcac aagatcactg caggtcacat   59520
tcatgaggaa aatgcaggca gttcctgcca tcagacccct caggatgtca tggtttggcc   59580
tgaaaacaag attcctgcaa ctctaatttt ccttgctga atcaaatgaa ggattgatc   59640
taatgtttgc attctagcag caaaatcatt gaatatttta tttcttaaga gccttacttc   59700
atattttgta ggtatttaa gattttgtaa aggcctttct gcttcaacgt gtgatgtgtg   59760
cattcttaga aaaagatctt gtgttctgta aatcacacaa taaaaacatg agttcgtgca   59820
ggaaaaactg gggcggggtg gatcactcca aacttgtgtg gtgtggtaac tggagctcac   59880
tgatgaaacc atgaacagtt ctggctgaaa gaaccccaca gtacactgag gtctgttggc   59940
```

```
atcgccgcca gcaccgcccc ggtcccttg tgcgcgccac cacacctggc taatttttta    60000
tttttagtag agaggggtt tcaccatgtt ggtcaggatg gcctcgaact gacctcgtga    60060
tccgccacc tcagcctccc aaagtgctgg gattacaggt gtgagcctcc gtgcccagcc    60120
ttcagctttt tttcttaatg tctttgtgta atatgaaggc attctcttta attgttaaaa    60180
agcttgccta ccactgcttc aaaatattac tgtcagttga catagctcct gattatattg    60240
atgtcatctc ccttcttta aacatgttac catattggca ctgtatttcc cctagcccat    60300
tgatcacttg agagttagtc atagtcctcg tgctgtttca ctcctaaacg tttaagcatg    60360
cctttcctaa gagcagacag tacagttaag acactcagga agtttagcaa tgagctaaca    60420
cagaaccttca catttctcca catacccat aaatgccttt tttagagctt ttgagcctga    60480
aatgcagagt ccaggactgt gtgttgtatt cgattgtgtc atcccttcag tctccttat    60540
cagaaatgtt cccccacccc cttgtttct ctcatcatct tgagtccaga ccgtggttgc    60600
atggcacgcc ctctctggac tcttcctgct gtctcctcac ggtaagcttc agtctcctac    60660
tcgtgatgct ggttcatctc agcagcactg aggggcctga gctcagtttg tcgtgtgtt    60720
aaggtggtgc ctgccagatt tctccacaga aaagggcccc gtactttat ttgctcttca    60780
gcctgtgtat tccttcctt cttgccagct tgtgggtggc ttctctagca gcttctgtaa    60840
gatactcagt ttggcagttg tagttgtttc agcaggagag gtgtctgcat acctgaccac    60900
cacatggcta gaagtcgatc catcctctgg cgtaaccatc ctccatgcta ctgtcccgg    60960
ggcactgagg ccctccccag tgacttcctc cacctcatct tccgccatct ccaagccacc    61020
agtgtccaac ggactactga tatgtcccaa actcatcatt tgtttattca ccaattcaga    61080
gcccacttt ttttcagcac tgagctagcc tctccttgct agaagcttac ggtcgaaggt    61140
ctccagccat cagaagaagc acgtggagcg ctgcgtccgt gttgtggtta ttcatccagc    61200
atgtgttgag taagggttgc acctgctgcct ggcattatgc attgagcggg gagatggggg    61260
ttggcacgca cagtggggtg ttctaagtac actgagggct cgggtgccct ggctcataga    61320
gcagggaggg aggcaggagc agggaaggtg tctcagaagt gccatctttt tttttttttt    61380
tttgggaagt ggaatcttgt tctatcgcct ggtctggagt gcaatggcac tatctcaact    61440
cactgcagcc tccgcctccc aggttcaagc gattctcatg cctcagtccc cgagtagctg    61500
ggaccacagg cgcacaccac cacacccggc aaatatttg tatttttagt agaggcggag    61560
ttttgccatg ttggccaggc tggtcttaaa ctcctggcct caagtgatct gctcacctcg    61620
gcctcctaag gtgttgggat tacaggcatg agccactgcg cccggtctag aagtgccatc    61680
ctaactgaac ctgaaagatg aaagttctcc agatgaacct aaagttctc caaatgaaaa    61740
ggtgggaggg ggtgacaggg ttaggcccag agcctctggt gacacagggt gggcatcatt    61800
ggtcactttt tcctcgaggg aggggcgtca cacgggtgat agggtgggag ctataaccat    61860
gttgatagtc ccgcctctgc ccatctggcc tggcatgccc tgagccctct gtcccacctg    61920
tggaactcat aagccctgac agcccactca ctcctgattc attatccaca ccctgtgct    61980
tccgctgtgc ctggagcaag ctttcttcag ggggaaggga ggctggaact atgttgtagt    62040
tacctatttg tcctcccttc caaactgtga gttcttggag gtggaaggat gctgcaggat    62100
ctggctcagg acgaaggcag ttggtgaaca gacacgtgtg tttttgactc acggtgatct    62160
cagacaagtt cctctgtcta gtcgaacttc ttttttttcc tctgtaacac tcaggagttg    62220
aataggtggt ttttctgagg atacttcaac tgtaaaatgt atgaacttgt gaactagcta    62280
tttagttctc ctcataatca agattgtgtg tgtgtggggg gttctgatta gagggaggat    62340
gaagagaggt gtatgggtt tttttgttt tgttttctgt ttgtttgttt gttttttgaga    62400
tggagtctca ctctgtcacc caggctggag tgcagtggca cgatttcggt tcactgcaac    62460
ctctgcctcc tgggttcaag tgattctcct gcctcagcct gtgagtaac tgggattaca    62520
ggcatgcacc accatgccca gctaattttt gtattttaa tagagatggg gttttcgcca    62580
tgttggccag gctggtctcg aactcctgac ctcaggtgat ccacctgcct cggcctccca    62640
aagtgctggg attataggca tgagccacca cacctggcag gtttctttga aaagttttgt    62700
gtttcggcaa acaccataaa ccccctgggg gacagccttg ggagtcacc tggcaccta    62760
gcccagcctc cctcccttgg gtcctgcagt gaaggcttag tgagggtgtg caaatgccca    62820
ggtcaccctg ggactgggca ggccctctgg gctaagggta aactcatttg gaatacctgt    62880
tttctatcat tgtttttat ttgttaaatt taaagggtac aagtgcagtt ttgttgcgtg    62940
gatatattgt atagtagtga agtctgagct ttcagtgtaa ccatcacctg aatagtggac    63000
attgtacccg ttaagtaatg tctcatccct cacccctcc cacccttccc agtctctcca    63060
gtgtctgcca ttcctcactc tgtccatgtg cacatgctat tcagctcctg cttctaagtg    63120
agaacgtacg gtatttgact ttctgtgtct gagctgtgtc actgaagaca atggactcca    63180
gctccatcca cgtttttat cattttacc tgcactccac acccagcaca atccaggctt    63240
ctttgtgggt tttttgaaat ttgtcttaa ttataaaagt agcagccagc aaattaacaa    63300
acacccatgt gcctttcatt gcacagaatt gaaatcatc atactatatt tgcttcaagt    63360
aattccatt agaaagaact agaatattac agtagagtta aagacccttt atttcccatc    63420
ttcagtgctc ttaaaagttc attttagggcc aggcaggtg gctcacacct ataatcccag    63480
cactttgaga ggcccaggtg ggtggatcac ctgaggtcag gagttcaaga ccagcctggc    63540
caacatggcg aaacccccatc tctactaaaa atacaaaaat tagctgggcg tggtggtgcg    63600
catctgtaat ctcagctact cgggaggctg aggcaggaga atcgcttgaa ctcaggaggg    63660
aggcagagcc tgtatgcagt aagccgagat tgcgccacca caccccagca tgggtgacag    63720
agcaagactc cgtctcaaaa aaaaaaaaaa aaaagttcat tcattgtaca cttagaaata    63780
gttaaaaagg taaactttgt tttgtgtgtg tgtgtatata tatatatata tatatatata    63840
tatatatata tatatgta tttttttttg agacatatat gtgtctggtt tgttcgccca    63900
ggcaggagtg cagtggcatg atcaacggct cactgcagcc tcaacttcct aggctcaagt    63960
gatcctcctg cctcagcctc ccgagtagct aggattacag gcacacacca ccatgcccag    64020
ctaattttt ttttttttt tttttttgt agagacaggg ttttgctatg ttgcccaggc    64080
tggtctcaaa ctcctgagct caagcgatcc acctgcctca cctcccaaag tgctgggatt    64140
acaagtgtaa gccaccacac ctgacctgtt ttgtatattt taccacaata aaagccttt    64200
aaaaccccaa gcagacagtt cattttcatt caggcccaac tcagaatctg atcacagcgg    64260
ggttccccc ctttctagcg agtagctgaa gaactgtttt ctccttga tggtataact    64320
gtctctgtgg gtgttgctcc cctgccgctc cagtgttttt ttgttttttt ttttttttt    64380
gagacgagt cttgcgatct cagctcactg cgacctctgc ctcctggtt caggcgattc    64440
ttctccctca gccttccatg tagctgggac ttacaggcac ctgccaccac gcccggctca    64500
tttttgtatt tttagtagag acggagtttc accatgttgg ccaggttggg ctcgaactcc    64560
agacctcagg tgatccacct gcctcagcct cccacagtgt tgggattaca ggtgagagcc    64620
actgcaccca gccggcccct cagtcttttc cttctcaatc agtggcacca ccatcttccc    64680
```

```
aggctttgga catggtccct gactcaccct tgccctcac cccacacta atccacctgc   64740
gagctctgtt gcttcaccac ctagaccagc cccaaatcct caactgcccc cacctgggc   64800
cacacctgga ccactgctag aggcctctca tgggccctcc ctgttttct cttgcactcc   64860
ccgggctttc tggcacaaga tgccccagaa gcagaatcac atatctctcc tgggagccaa   64920
tctagtgtgt ttactgcccc tggagtgtta ttgttgaccc tagaatatgt cccactacag   64980
gtttgcagag cactgtagtc aaaagtcatt tgaaataaat cttttctctg tggtatattg   65040
tcaatttgat atagaattaa atttgttct ttctttttt cttttcttt tttttttttt     65100
taagagacag ggtcttggcc aggcgtggtg tctcatgcct gtaatcccgg cactttggga   65160
agccaaggtg ggtggatcgc ctgaggtcag gaattcaaga ccaacctggc cagcatggtg   65220
aaaccccgtc tctgctaaaa atacaaaaat tagccgggcg tgatggcagg tacctgtaat   65280
cccagctact cgggaagctg aggcaggaga aggcttgaac tcaggagtcg gaggttgcag   65340
tgagccaaga tcacgccatg gcactctagc aagactctgt ctcaaaaaaa aaaaagaga    65400
gagagagaga cagggtcttg ctctgtcact caggctggag tgcagtgatg tagtcatggc   65460
tcactgcagc ctcatactcc tgacctcagg tgatcgaccc gcctcggcct ccgcttagcc   65520
tgggatcgta ggctgaagcc accatgcctg gcccgaactc atttgtttt atttgcatta    65580
agtgtaataa ggttttgtta cttttagttt gaatttatt ttgggtaata taaacattta    65640
catgattcag aagtcagaat tacactgagg catgttcagc taggcctcac tcctgtgcct   65700
gtacccttac cttttccc ctaccccatg cagggaatca atttcattag ttcctggtgt     65760
gtccttcctt aatacccccc cttctttctt tggtagaatg cagtagatat gtttgcgctt   65820
tgctccctt gcttcacagt ggatcctgga aatgactcca tcgcagttct tagagctctt    65880
gtttagtccc tttggatctg cacagtactc cagtgtgtgg gcgcaccata agtttattca   65940
gcaagtgccc tggtgatagg gatcgggggt atttggaagc tttggctggt aaaaataatg   66000
ttgtagcaaa taacatcatg catatgttct ttgagatttc tggaggtgtc tcttagcat    66060
agattctag aaggcattcc ttacgtcacg tttaggttta tagttgacc tcatggtgat     66120
taaggtattt gggaaatgca aatgagagtt tcgaagaagc cagatctttc ccattagttc   66180
actgtttttc tctgacatta ggacctccg ggttctaggg agcagccctg gcgttaggca    66240
gtgccatgat ggattgtgta gaagtagcga ttcccatctg tctgctttct tggcccactc   66300
tgctggtggc tccccttccc tcctcctttt atggggagct ggggagctgc ctaggggtcc   66360
attctcaaag gctgatctct ggtgggcaac aggccacacc tagcttcca gggttcttcg    66420
tcatttccca ttgagagctg taagactcag agacatgaaa aggaagctct ggctgggcac   66480
ggtggctcac gcctgtaatc ccagcacttt ggggaggctga ggcgggtcga tcacctgagg   66540
tcaggagttc gagaccagcc tgccaacat ggtgaaaccc cgtctccact aaacatacaa     66600
aaattagcct ggcgtggtag cacacgcctg tgatcccagc tactccggag gctgaggcag   66660
gagaataact tgaacccggc aggcggaggt tgcgatgagc cgatattatg ccatcggcaa   66720
cagagcgaga ctccatctca aaaaaaaaac aaaaaacaaa acaaggcgag ctctgtgctg   66780
ggacagatta gggaccctc tttacagcaa gaaagactgc tctgtgggtt gtaggatgcc    66840
tttgtgtatg cagtggctct aggtgactct ggcagccaca ctctgggccc taaacttctg   66900
gaggaagata caggataggg aggaactcag gggtgagtca tggtggggac aagacattcc   66960
ctcactctaa gaccttgtca ctagattgga acatctcttg cctccctaca cctgacctga   67020
tggttctgga gagatacgtc cttgcagctt ctgagtccca gcactaagca gcctttggta   67080
acttccctac atcatttgag ttctggtttc ctaaggatgc ttgccagtga gtgccatggt   67140
gccctcattg cacagtctgt gcagtgtaga caagagggga agtctcttgg ggtagaccag   67200
ccgcaaggcg gtgactagca ctgatgtgaa ccacatggga cagggagtt gtggggctga    67260
gaacacggag ggtgggagta gtcatgctct tttccagaat gaactgctaa cgaagggact   67320
cgcaggtggc tgctgcttct ttccaagctg cccctgttgt tgcagaggct ctggagtcct   67380
aggaggtttc acgtggcat actcgacaga gtactagagc atcatggcca gatagtgatg    67440
ctggggtgg gggcctcacg gtggccattt ctgacgagac cccaccggc caaagtgatg     67500
tgtagagaag gagctgcttc ggtcaccaga aaagaacggg gaagcctccc acactgaat    67560
aggtagggtg ctcttctcca ccggcaggaa ggggatgtat ggctctgcct ggaccacacc   67620
tttttccttg ctcttccctc cgcatctgct gtggccgagg ccattcctca tcagggaaca   67680
tgtgttagag gctcacgcca cctgggacca ctttgtcttat caccccagg accctaggcg     67740
gtagtttcct gtggcctgag ttagctgata tttatatagt gccattgtgc cttttctcct   67800
gtgatgctca cagtcaaggat gcctagatgg ggttaccgtg tgtcaagata aggaaactga   67860
agcacagaat gctgaggtca tttgctgggt tcatgtttgg aaagcggcaa aggatttcag   67920
tgcaggttgg ggctgctcaa acctgtgtgt gctttccatg acactgtact gtgtgcctca   67980
ttgagcctca ttctagaaaa ccaaaaacac acccaaggcc cggccttcac aaaggagacc    68040
cctccccat ttggctccct ttccagcagt cgacggcctc ttgtcagcca tcgagccag    68100
agtcccttga agtgcgactc atgctgggt gtatgctca ggagccgcag tgtttccgct     68160
cagaggaaag ggctctgatt ctcctgcagt gctaggagac ttgtgggtgg ccacagtgca   68220
ggtcaggcac accggccagc accacccaca gcccaaattc ctaaagaaat atttgggtcc   68280
cagcttggcc cgagtctctg ttgtcctggg gaaggacatc aagatctgag tgtatgatgg    68340
cctgggggcct tgcatgtggt gggggtccaa gcctgcctct gctcacttgt tctgcagact   68400
ggcatgttct ctgtgatact tacatacttg tttaacactt cagggaagaa aagtcagaag   68460
accaggacct ccagggcctc aaggacaaac ccctcaagtt taaaaaggtg aagaaagata   68520
agaaagaaga gaaagagggc aagcatgagc ccgtgcagcc atcagcccac cactctgctg   68580
agcccgcaga ggcaggcaaa cagagacat cagaagggtc aggctccgcc ccggctgtgc    68640
cggaagcttc tgcctccccc aaacagcggc gctccatcat ccgtgaccgg gacccatgt    68700
atgatgaccc caccctgcct gaaggctgga cacgaaagt taagcaaagg aaatctggcc   68760
gctctgctgg gaagtatgat gtgtatttga tcaagtaagt aagagcaact cctatctcta   68820
cagggcaggg agggcaggga caaggatccc tcatggagca ggaaaatgta tgtgcccagg   68880
gtgggtcgg gggaacata aacaatgaac actgagacca ggtgtgcttg aaatgaccgt      68940
gtacagaggt cgctgccctg agtgggaagt tctcaaggta gcaggcctc tatcctctcc    69000
acacctcaag tctttatctg gggatggaat agctgcggaa gcagaggaac ttgcagagct   69060
aggggttcag aggggtgaag aacatgttt cagttctgcc ttttaaatga tcccaaaag    69120
gttagcagtt ttcaaatgac attgcagac agcctcattt aattccatga aagggtgag     69180
caaaggatta tcttgttgaa actgattcct ggagagactg agcaccgtac ctgagttcaa   69240
acttgggaat gttctagatg gtgactcagg cccaggcacc aaccagcaga atgggcctca   69300
gcctgacaac ccttctgtac caggcctgac tcttgggttt ctgaactttg gagaggcctg   69360
gggggtcag cggcaggcag acgagtgagt ggctttggtg acaggtcctc aggggcagcc    69420
```

```
aggcagtgtg actctcgttc aatagtaacg tttgtcagag cgttgtcacc accatccgct  69480
ctgccctatc tctgacattg ctatggagag cctctaattg ttccttgtgt ctttctgttt  69540
gtccccacag tccccaggga aaagcctttc gctctaaagt ggagttgatt gcgtacttcg  69600
aaaaggtagg cgacacatcc ctggacccta atgattttga cttcacggta actgggagag  69660
ggagcccctc ccggcgagag cagaaaccac ctaagaagcc caaatctccc aaagctccag  69720
gaactggcag aggccgggga cgccccaaag ggagcggcac cacgagaccc aaggcggcca  69780
cgtcagaggg tgtgcaggtg aaaagggtcc tggagaaaag tcctgggaag ctccttgtca  69840
agatgccttt tcaaacttcg ccaggggca aggctgaggg gggtggggcc accacatcca  69900
cccaggtcat ggtgatcaaa cgccccggca ggaagcgaaa agctgaggcc gaccctcagg  69960
ccattcccaa gaaacggggc cgaaagccgg ggagtgtggt ggcagccgct gccgccgagg  70020
ccaaaaagaa agccgtgaag gagtcttcta tccgatctgt gcaggagacc gtactcccca  70080
tcaagaagcg caagaccgg gagacggtca gcatcgaggt caaggaagtg gtgaagcccc  70140
tgctggtgtc caccctcgt gagaagagcg ggaaaggact gaagacctgt aagagccctg  70200
ggcggaaaag caaggagagc agccccaagg ggcgcagcag cagcgcctcc tcacccccca  70260
agaaggagca ccaccaccat caccaccact cagagtcccc aaaggccccc gtgccactgc  70320
tcccaccct gccccacct ccacctgagc ccgagagctc cgaggacccc accagccccc  70380
ctgagcccca ggacttgagc agcagcgtct gcaaagagga gaagatgccc agaggaggct  70440
cactggagag cgacggctgc cccaaggagc cagctaagac tcagcccgcg gttgccaccg  70500
ccgccacggc cgcagaaaag tacaaacacc gaggggaggg agagcgcaaa gacattgttt  70560
catcctccat gccaaggcca aacagagagg agcctgtgga cagccggacg cccgtgaccg  70620
agagagttag ctgactttac acggagcgga ttgcaaagca aaccaacaag aataaaggca  70680
gctgttgtct cttctcctta tgggtagggc tctgacaaag cttcccgatt aactgaaata  70740
aaaaatattt tttttctt cagtaaactt agagtttcgt ggcttcaggg tgggagtagt  70800
tggagcattg gggatgtttt tcttaccgac aagcacagtc aggttgaaga cctaaccagg  70860
gccagaagta gctttgcact tttctaaact aggctccttc aacaaggctt gctgcagata  70920
ctactgacca gacaagctgt tgaccaggca cctcccctcc cgcccaaacc tttcccccat  70980
gtggtcgtta gagacagagc gacagagcag ttgagaggac actcccgttt tcggtgccat  71040
cagtgccccg tctacagctc cccagctcc ccccacctcc cccactccca accacgttgg  71100
gacagggagg tgtgaggcag gagagacagt tggattcttt agagaagatg gatatgacca  71160
gtggctatgg cctgtgcgat cccacccgtg gtggctcaag tctggcccca caccagcccc  71220
aatccaaaac tggcaaggac gcttcacagg acaggaaagt ggcacctgtc tgctccagct  71280
ctggcatggc taggaggggg gagtcccctg aactactggg tgtagactgg cctgaaccac  71340
aggagaggat ggcccagggt gaggtggcat ggtccattct caaggacgt cctccaacgg  71400
gtggcgctag aggccatgga ggcagtagga caaggtgcag gcaggctggc ctgggtcag  71460
gccggacaga gcacagccgg gtgaggagga ttcctaatca ctcagagcag tctgtgactt  71520
agtggacagg ggaggggca aaggggagg agaagaaaat gttcttccag ttactttcca  71580
attctcctt agggacagct tagaattatt tgcactattg agtcttcatg ttcccacttc  71640
aaaacaaaca gatgctctga gagcaaactg gcttgaattg gtgacattta gtccctcaag  71700
ccaccagatg tgacagtgtt gagaactacc tggatttgta tatatacctg cgcttgtttt  71760
aaagtgggct cagcacatag ggttcccacg aagctccgaa actctaagtg tttgctgcaa  71820
ttttataagg acttcctgat tggtttctct tctccccttc catttctgcc ttttgttcat  71880
ttcatccttt cacttcttc ccttcctcca tcctcctcct tcctagttca tcccttctct  71940
tccaggcagc cgcggtgccc aaccacactt gtcggctcca gtccccagaa ctctgcctgg  72000
cctttgtcct cctgctgcca gtaccagccc caccctgttt tgagcccga ggaggccttg  72060
ggctctgctg agtccgacct ggcctgtctg tgaagagcaa gagagcagca aggtcttgct  72120
ctcctaggta gccccctctt ccctggtaag aaaaagcaaa aggcatttcc cacccctgaac  72180
aacgaggcctt ttcacccttc tactctagag aagtggactg gaggagctgg gcccgatttg  72240
gtagttgagg aaagcacaga ggcctcctgt ggcctgccag tcatcgagtg gcccaacagg  72300
ggctccatgc cagccgacct tgacctcact cagaagtcca gagtctagcg tagtgcagca  72360
gggcagtagc ggtaccaatg cagaactccc aagacccgag ctgggaccag tacctgggtc  72420
cccagccctt cctctgctcc ccctttttcc tcggagttct tcttgaatgg caatgttttg  72480
cttttgctcg atgcagacag ggggccagaa caccacacat ttcactgtct gtctggtcca  72540
tagctgtggt gtagggggctt agaggcatgg gcttgctgtg ggttttaat tgatcagttt  72600
tcatgtggga tcccatcttt ttaacctctg ttcaggaagt ccttatctag ctgcatatct  72660
tcatcatatt ggtatatcct ttttctgtgtt tacagagatg tctcttatat ctaaatctgt  72720
ccaactgaga agtaccttat caaagtagca aatgagacag cagtcttatg cttccagaaa  72780
cacccacagg catgtcccat gtgagctgct gccatgaact gtcaagtgtg tgttgtcttg  72840
tgtatttcag ttattgtccc tggcttcctt actatggtgt aatcatgaag gagtgaaaca  72900
tcatagaaac tgtctagcac ttccttgcca gtctttagtg atcaggaacc atagttgaca  72960
gttccaatca gtagcttaag aaaaaaccgt gtttgtctct tctgaatgg ttagaagtga  73020
gggagtttgc cccgttctgt ttgtagagtc tcatagttgg actttctagc atatatgtgt  73080
ccatttcctt atgctgtaaa agcaagtcct gcaaccaaac tcccatcagc caatccctg  73140
atccctgatc ccttccacct gctctgctga tgacccccc agcttcactt ctgactcttc  73200
cccaggaagg gaaggggggt cagaagagag ggtgagtcct ccagaactct tcctccaagg  73260
acagaaggct cctgccccca tagtggcctc gaactcctgg cactaccaaa ggacacttat  73320
ccacgagagc gcagcatccg accaggttgt cactgagaag atgtttattt tggtcagttg  73380
ggttttatg tattatactt agtcaaatgt aatgtggctt ctggaatcat tgtccagagc  73440
tgcttccccg tcacctgggc gtcatctggt cctggtaaga ggagtgcgtg gcccaccagg  73500
ccccctgtc acccatgaca gttcattcag ggccgatggg gcagtcgtgg ttgggaacac  73560
agcatttcaa gcgtcacttt atttcattcg ggcccacct gcagctccct caaagaggca  73620
gttgccagc ctcttccct tccagtttat tccagactg ccagtggggc ctgaggctcc  73680
ttagggtttt ctctctattt cccccttct tcctcattcc ctcgtctttc ccaaaggcat  73740
cacgagtcag tcgcctttca gcaggcagcc ttggcggttt atcgccctgg caggcagggg  73800
ccctgcatct catgctgc ccctgccttg gggtcaggtt gcaggaggt tggagggaaa  73860
gccttaagct gcaggattct caccagctgt gtccggccca gttttggggt gtgacctcaa  73920
tttcaatttt gtctgtactt gaacattatg aagatggggg cctctttcag tgaatttgtg  73980
aacagcagaa ttgaccgaca gctttccagt cccatggggg ctaggtcatt aaggccacat  74040
ccacagtctc ccccaccctt gttccagttg ttagttacta cctcctctcc tgacaatact  74100
gtatgtcgtc gagctccccc caggtctacc cctcccggcc ctgcctgctg gtgggcttgt  74160
```

```
catagccagt gggattgccg gtcttgacag ctcagtgagc tggagatact tggtcacagc   74220
caggcgctag cacagctccc ttctgttgat gctgtattcc catatcaaaa gacacagggg   74280
acacccagaa acgccacatc ccccaatcca tcagtgccaa actagccaac ggccccagct   74340
tctcagctcg ctggatggcg gaagctgcta ctcgtgagcg ccagtgcggg tgcagacaat   74400
cttctgttgg gtggcatcat tccaggcccg aagcatgaac agtgcacctg ggacagggag   74460
cagcccaaa ttgtcacctg cttctctgcc cagcttttca ttgctgtgac agtgatggcc   74520
aaagagggta ataaccagac acaaactgcc aagttgggtg gagaaaggag tttcttttagc  74580
tgacagaatc tctgaatttt aaatcactta gtaagcggct caagcccagg agggagcaga   74640
gggatacgag cggagtcccc tgcgcgggac catctggaat tggttttagcc caagtggagc   74700
ctgacagcca gaactctgtg tcccccgtct aaccacagct cctttccag agcattccag    74760
tcaggctctc tgggctgact gggccagggg aggttacagg taccagttct ttaagaagat    74820
cttgggcat atacatttt agcctgtgtc attgccccaa atggattcct gtttcaagtt     74880
cacacctgca gattctagga cctgtgtcct agacttcagg gagtcagctg tttctagagt    74940
tcctaccatg gagtgggtct ggaggacctg cccggtgggg gggcagagcc ctgctccctc    75000
cgggtcttcc tactcttctc tctgctctga cgggatttgt tgattctctc cattttggtg    75060
tcttctcttt tagatattg tatcaatctt tagaaaaggc atagtctact tgttataaat     75120
cgttaggata ctgcctcccc cagggtctaa aattacatat tagaggggaa aagctgaaca   75180
ctgaagtcag ttctcaacaa tttagaagga aaacctagaa aacatttggc agaaaattac    75240
atttcgatgt ttttgaatga atacgagcaa gcttttacaa cagtgctgat ctaaaaatac    75300
ttagcacttg gcctgagatg cctggtgagc attacaggca aggggaatct ggaggtagcc    75360
gacctgagga catggcttct gaacctgtct tttgggagtg gtatgaagg tggagcgttc     75420
accagtgacc tggaaggccc agcaccacc tccttcccac tcttctcatc ttgacagagc    75480
ctgcccccagc gctgacgtgt caggaaaaca cccagggaca taggaaggca cttctgcctg    75540
aggggcagcc tgccttgccc actcctgctc tgctcgcctc ggatcagctg agccttctga   75600
gctggcctct cactgcctcc ccaaggcccc ctgcctgccc tgtcaggagg cagaaggaag    75660
caggtgtgag gcagtgcaa ggagggagca caacccccag ctccccgctcc gggctccgac   75720
ttgtgcacag gcagagccca gaccctggag gaaatcctac ctttgaattc aagaacattt     75780
ggggaattttg gaaatctctt tgccccaaa ccccccattct gtcctacctt taatcaggtc   75840
ctgctcagca gtgagagcag atgaggtgaa aaggccaaga ggtttggctc ctgcccactg    75900
atagccccctc tcccccgcagt gttttgtgtgt caagtggcaa agctgttctt cctggtgacc   75960
ctgattatat ccagtaacac atagactgtg cgcataggcc tgctttgtct cctctatcct   76020
gggcttttgt tttgcttttt agttttttct ttagttttc tgtcccttt atttaacgca     76080
ccgactagac acacaaagca gttgaatttt tatatatata tctgtatatt gcacaattat   76140
aaactctttt tgcttgtggc tccacacaca caaaaaaag cctgttaaaa ttatacctgt    76200
tgcttaatta caatatttct gataaccata gcataggaca agggaaaata aaaaagaaa     76260
aaaaagaaaa aaaacgaca aatctgtctg ctggtcactt cttctgtcca agcagattcg    76320
tggtcttttc ctcgcttctt tcaagggctt cctgtgcca ggtgaaggag ctccaggca     76380
gcacccaggt tttgcactct tgtttctccc gtgcttgtga aagaggtccc aaggttctgg   76440
gtgcaggagc gctcccttga cctgctgaag tccggaacgt atcggcaca gcctggtcgc    76500
cttccacctc tgggagctgg agtccactgg ggtggcctga ctcccccagt ccccttccgc    76560
tgacctggtc agggtgagcc catgtggagt cagcctcgca ggcctccctg ccagtagggt    76620
ccgagtgtgt ttcatcctc ccactctgtc gagcctgggg gctggagcgg agacgggagg    76680
cctggcctgt ctcggaacct gtgagctgca ccaggtagga gccaggggc cccagaatca     76740
tgtgcgtcag tccaaggggg cccctccagg agtagtgaag actccagaaa tgtcccttc    76800
ttctccccca tcctacgagt aattgcatt gcttttgtaa ttcttaatga gcaatatctg   76860
ctagagagtt tagctgtaac agttcttttt gatcatcttt ttttaataat tagaaacacc   76920
aaaaaaatcc agaaacttgt tcttccaaag cagagagcat tataatcacc agggccaaaa   76980
gcttccctcc ctgctgtcat tgcttcttct gaggcctgaa tccaaaagaa aaacagccat    77040
aggcccttc agtggccggg ctacccgtga gcccttcgga ggaccagggc tggggcagcc    77100
tctgggccca catccgggc cagctccggc gtgtgttcag tgttagcagt gggtcatgat     77160
gctcttttcc acccagcctg ggatagggc agaggaggca aggaggcgt tgccgctgca    77220
gtttggccgt gaacaggtgg gtgtctgcgt gcgtccacgt gcgtgttttc tgactgacat    77280
gaaatcgacg cccgagttag cctcacccgg tgacctctag ccctgcccgg atggagcggg    77340
gcccacccgg ttcagtgttt ctggggagct ggacagtgga gtgcaaaagg cttgcagaac   77400
ttgaagcctg ctccttccct tgctaccacg gcctccttc cgtttgattt gtcactgctt     77460
caatcaataa cagccgctcc agagtcagta gtcaatgaat atatgaccaa atatccaccag   77520
gactgttact caatgtgtgc cgagcccttg cccatgctgg gctcccgtgt atctggacac     77580
tgtaacgtgt gctgtgttg ctcccctcc ccttccttct ttgcccttta cttgtctttc     77640
tggggttttt ctgtttgggt ttggtttggt tttatttct ccttttgtt tccaaacatg      77700
aggttctctc tactgctcct cttaactgtg gtgttgaggc ttatatttgt gtaattttg     77760
gtgggtgaaa ggaatttgc taagtaaatc tcttctgtgt ttgaactgaa gtctgtattg     77820
taactatgtt taaagtaatt gttccagaga caaatatttc tagacacttt ttctttacaa   77880
acaaaagcat tcggagggag ggggatggtg actgagatga gagggagag ctgaacagat     77940
gaccccctgcc cagatcagcc agaagccacc caaagcagga gccccagga gtcccactcc     78000
aagcagcaa gccgaatagc tgatgtgttg ccactttcca agtcactgca aaccaggtt     78060
ttgttccgcc cagtggattc ttgttttgct tccccctccc ccgagattat taccaccatc    78120
ccgtgctttt aaggaaaggc aagattgatg tttccttgag gggagccagg aggggatgtg    78180
tgtgtgcaga gctgaagagc tggggagaat ggggctgggc ccacccaagc aggaggctgg   78240
gacgctctgc tgtgggcaca gtcaggcta atgttggaca atgcagctct tcctggacag    78300
gccaggtggt gggcattctc tctccaaggt gtgccccgtg ggcattactg tttaagacac   78360
ttccgtcaca tcccacccca tcctccaggg ctcaacactg tgcatctct attccccacc    78420
ctccccttcc cagggcaata aaatgaccat ggagggggct tgcactctct tggctgtcac    78480
ccgatcgcca gcaaaactta gatgtgagaa aacccctttcc cattccatgg cgaaaacatc   78540
tccttagaaa agccattacc tcattaggc atggttttgg gctcccaaaa cacctgacag    78600
cccctccctc ctctgagagg cggagagtgc tgactgtagt gaccattgca tgccgggtgc   78660
agcatctgga agagctaggc aggggtgtct cccctcctg agttgaagtc atgctccct      78720
gtgccagccc agaggccgag agctatggac agcattgcca gtaacacagg ccaccctgtg   78780
cagaaggga ctggctccag cctggaaacc tgtctgaggt tgggagaggt gcacttgggg    78840
cacagggaga ggccgggaca cacttagctg gagatgtctc taaaagccct gtatcgtatt   78900
```

```
caccttcagt ttttgtgttt tgggacaatt actttagaaa ataagtaggt cgttttaaaa    78960
acaaaaatta ttgattgctt ttttgtagtg ttcagaaaaa aggttctttg tgtatagcca    79020
aatgactgaa agcactgata tatttaaaaa caaaaggcaa tttattaagg aaatttgtac    79080
catttcagta aacctgtctg aatgtacctg tatacgtttc aaaaacaccc cccccccact    79140
gaatccctgt aacctattta ttatataaag agtttgcctt ataaatttac ataaaaatgt    79200
ccgtttgtgt cttttgttgt aaaaatcaag tgattttttc ataaggttct tttactattg    79260
gaaaagatgg gcagcacgca gttttatttt attttttgtaa gttttttaat acatgtgaaa    79320
gcaaagaata ctcagcatgc ctttctaagt gacgcgtttg caccttttgt tgggaagtac    79380
tgtatcctgt gctgttagca ttctcgataa atctctctgt gaaagtgact caaggtctga    79440
gctttcatta taagacagaa gtcccctcc agctcacatg acagcatggt gctgcgtttc    79500
ctcattggat ctggctgtcc ctggacacag gtagctgcct tcaggcctgc cacgagcggc    79560
caagggaagc ctcctccata tgctggcctc gctggcccct cagcttcttc caagccagtg    79620
ctctccaggc acactgctcc agcgtgtgac gggaagggcc tggcatgagt cagcctgcag    79680
cacaacctcc ctgctccaga cccgtatggt aggggcaccc cctaggtctg gatgtgctgt    79740
ggtgcttttg gacaccccca cccccgcagg ctgtggctcc tcctgtgtct cattctggcc    79800
aggaccctca cgtgccctct gttgactgct aacgtggttc tctgaccagg caagggcagg    79860
ctgaggggtt tgcccaaagg gggccccctt gttactggct tccttggctc tcaggagcag    79920
cctcaccagg ttggtaaggg gctggaggag acaactgctc aaaggagtcc agcttcacat    79980
gcacatgcta gaaggtaccc tcggaaggcc tggccttcaa aggtagatcc cagggttgaa    80040
aagtcaactt gtatgcattg agcatctcgt atgccagccc tgttccgtga gctgatgggc    80100
ctttgtgtgt aagtaggacc aagtgccccc gtggaggtta gcatgggtgt gcagtcattt    80160
cagatacttg agttggtaca tctcagtaaa gtctgtcccg tgagaagcca tgggtttcat    80220
ggtatggttg gcatcttcct tgggagtggc cacagtggtg gtggcttcag gaaagagact    80280
ccaacagggg ccagctgtgg gccttgggca cttctcgttt ctaggaaaag tcctaagtct    80340
gtagggctag gggtggggaa ccccttcgct gtcaggatca agagggcaag gggaactgtc    80400
gctggaggag acatccagct ggagaaacaa aagagtaagt ctgcgtttgc gcttgtgggg    80460
tcttccccat ctcagggcgg gaccggggg tggcggtcca gacaagtaat caaggacgat    80520
gcccaggagg ggacaggtac ggggtggcag gagctctgcc ggcgggctca ggaagccttc    80580
accacagctg cctgagctca cccttgccaa atgagggctg gggcagcagc aacgcataca    80640
ctcacggctg tggcgggcag cgttctcggc atatttcagg acacctaagg agactgaatg    80700
gctcaaggct gctgccgtgt gcaggggggct agacgtgggg cgggcaggca gggctcctgg    80760
taacagccct gcaggccgca gtggagagca gggttccggc agggccgccc aggagctttc    80820
ggaaggcccg gccccggccc cttccgagc agcccgggcc tccgccctgc cctctgtccc    80880
caacgccggg agcgccgtt cgtcctccag agccccgccc gggcgagccc gggaggccga    80940
tcgccgctcg cggaaccgc cgggacccgc gccctcccg gcgcgggggcg ccccgtgtg    81000
acccagcgcg cggccgcgge gcgcaagatg gcggcgggcc cgggcaccgc cccttccgcc    81060
ccgccggggc tcgcacgagg ccggctcgaa ggggaagtga gtcagtgtcc gcggaccgg    81120
ccggcccagg cccgcgcccg ccgcggccct gagaggcccc ggcaggtccc ggcccggcgg    81180
cggcagccat ggccgggggg ccgggccggg ggagcccggc agccccgggc gcccagcact    81240
tcttgtacga ggtgccgccc tgggtcatgt gccgcttcta caaagtgatg gacgccctgg    81300
agcccgccga ctggtgccag ttcggtgggg gcggcgggc tgccgggggg cgggaggcgc    81360
gcgggctcct ggcgccgacg cctgacgccc ccgcccgc agccgccctg atcgtgcgcg    81420
accagaccga gctgcgctg tgcgacccgg ccgggccagc caggccagc gtcctgtgcc    81480
cctggatcaa ccgcaacgcc cgtgtggccg acctcgtgca catcctcacg cacctgcagc    81540
tgctccgtgc gcgggacatc atcacagcct gtgagcgcgg gactccgggc accccacggc    81600
tgggaggccg gcgggcccca cggggctccc cacccgggc ctcaaccttc ctttccttcc    81660
ttggcgtccc agggcaccct cccgcccgc ttccgtcccg aggcaccact gccccgaggc    81720
ccagcagcat ccctgcaccc gccgaggccg aggcctggag ccccggaag ttgccatcct    81780
cagcctccac cttcctctcc ccaggtaaga gggcccggtt gttaggcctg gtggacccaa    81840
agaagagccc accttgacca cggccacggc tgtagaccct gctgctggtc tctgcctgcc    81900
tctcactggt gtctttatga agcttttcca ggctcccaga cccattcagg gcctgagctc    81960
ggcctggtcc caagccctgc ttccctgtgg cctccaccgc                          82000
```

SEQ ID NO: 2        moltype = RNA  length = 10241
FEATURE              Location/Qualifiers
source               1..10241
                     mol_type = mRNA
                     organism = Homo sapiens
SEQUENCE: 2

```
ccggcgtcgg cggcgcgcgc gctccctcct ctcggagaga gggctgtggt aaaagccgtc      60
cggaaaatgg ccgccgccgc cgccgccgcg ccgagcggag gaggaggagg aggcgaggag     120
gagagactgc tccataaaaa tacagactca ccagttcctg ctttgatgtg acatgtgact     180
ccccagaata caccttgctt ctgtagacca gctccaacag gattccatgg tagctgggat     240
gttagggctc agggaagaaa agtcagaaga ccaggacctc cagggcctca aggacaaacc     300
cctcaagttt aaaaaggtga agaaagataa gaaagaagag aaagagggca agcatgagcc     360
cgtgcagcca tcagcccacc actctgctga gcccgcagag gcaggcaaag cagagacatc     420
agaagggtca ggctccgccc cggctgtgcc ggaagcttct gcctcccca aacagcggcg     480
ctccatcatc cgtgaccggg gacccatgta tgatgaccc acctgcctg aaggctggac     540
acggaagctt aagcaaagga aatctggccg ctctgctggg aagtatgatg tgtatttgat     600
caatccccag ggaaaagcct ttcgctctaa agtggagttg attgcgtact tcgaaaaggt     660
aggcgacaca tccctggacc ctaatgattt tgacttcacg gtaactggga gagggggccc     720
ctcccggcga gagcagaaac cacctaagaa gcccaaatct cccaaagctc caggaactgg     780
cagaggccgg ggacgcccca aagggagcgg caccacgaga cccaaggcgg ccacgtcaga     840
gcacagtggg gtgaaaaggg tcctggagaa aagtccttgga aagtccttgg a agtcccttg     900
tttttcaaact tcgccagggg gcaaggctga gggggggtggg gccaccacat ccacccaggt    960
catggtgatc aaaacgcccg gcaggaagcg aaaagctgag gccgaccctc aggccattcc    1020
caagaaacgg ggccgaaagc cggggagtgt ggtggcagcc gctgccgccg aggccaaaaa    1080
gaaagccgtg aaggagtctt ctatccgatc tgtgcaggag accgtactcc ccatcaagaa    1140
gcgcaagacc cgggagacgg tcagcatcga ggtcaaggaa gtggtgaagc ccctgctggt    1200
```

```
gtccaccctc ggtgagaaga gcgggaaagg actgaagacc tgtaagagcc ctgggcggaa 1260
aagcaaggag agcagcccca aggggcgcag cagcagcgcc tcctcacccc caagaagga  1320
gcaccaccac catcaccacc actcagagtc cccaaaggcc cccgtgccac tgctcccacc 1380
cctgccccca cctccacctg agcccgagag ctccgaggac cccaccagcc cccctgagcc 1440
ccaggacttg agcagcagcg tctgcaaaga ggagaagatg cccagaggag gctcactgga 1500
gagcgacggc tgccccaagg agccagctaa gactcagccc gcggttgcca ccgccgccac 1560
ggccgcagaa aagtacaaac accgagggga gggagagcgc aaagacattg tttcatcctc 1620
catgccaagg ccaaacagag aggagcctgt ggacagccgg acgcccgtga ccgagagagt 1680
tagctgactt tacacggagc ggattgcaaa gcaaaccaac aagaataaag gcagctgttg  1740
tctcttctcc ttatgggtag ggctctgaca aagcttcccg attaactgaa ataaaaaata 1800
ttttttttc tttcagtaaa cttagagttt cgtggcttca gggtgggagt agttggagca 1860
ttggggatgt ttttcttacc gacaagcaca gtcaggttga agacctaacc agggccagaa 1920
gtagctttgc acttttctaa actaggctcc ttcaacaagg cttgctgcag atactactga 1980
ccagacaagc tgttgaccag gcacctcccc tcccgcccaa acctttcccc catgtggtcg 2040
ttagagacag agcgacagag cagttgagag gacactcccg ttttcggtgc catcagtgcc 2100
ccgtctacag ctcccccagc tcccccacc tccccactc caaccacgt gggacaggg 2160
aggtgtgagg caggagagac agttggattc tttagagaag atggatatga ccagtggcta 2220
tggcctgtgc gatcccaccc gtggtggctc aagtctggcc ccacaccagc cccaatccaa 2280
aactggcaag gacgcttcac aggacaggaa agtggcacct gtctgctcca gctctggcat 2340
ggctaggagg ggggagtccc ttgaactact gggtgtagac tggcctgaac cacaggagag 2400
gatgcccag ggtgaggtgg catggtccat tctcaaggga cgtcctccaa cgggtggcgc 2460
tagaggccat ggaggcagta ggacaaggtg caggcaggct ggctcggggt caggccgggc 2520
agagcacagc ggggtgagag ggattcctaa tcactcagag cagtctgtga cttagtggac 2580
agggagggg gcaaagggg aggagaagaa aatgttcttc cagttacttt ccaattctcc 2640
tttagggaca gcttagaatt atttgcacta ttgagtcttc atgttcccac ttcaaaacaa 2700
acagatgctc tgagagcaaa ctggcttgaa ttggtgacta ttagtccctc aagccaccag 2760
atgtgacagt gttgagaact acctggattt gtatatatac ctgcgcttgt tttaaagtgg 2820
gctcagcaca taggggttccc acgaagctcc gaaactctaa gtgttttctg caattttata 2880
aggacttcct gattggtttc tcttctcccc ttccattct gcctttgtt catttcatcc 2940
tttcacttct ttcccttcct ccgtcttcct ccttcctagt tcatccctc tcttccaggc 3000
agccgcggtg cccaaccaca cttgtcggct ccagtcccca gaactctgcc tgcccttgt  3060
cctcctgctg ccagtaccag cccaccctg ttttgagccc tgaggaggcc ttgggctctg 3120
ctgagtccga cctggcctgt ctgtgaagag caagagagca gcaaggtctt gctctcctag 3180
gtagccccct cttccctggt aagaaaagc aaaaggcatt tcccaccctg aacaacgagc 3240
cttttcaccc ttctactcta gagaagtgga ctggaggagc tgggcccgat ttggtagttg 3300
aggaaagcac agaggcctcc tgtggcctgc cagtcatcga gtggcccaac aggggctcca 3360
tgccagccga ccttgacctc actcagaagt ccagagtcta gcgtagtgca gcagggcagt 3420
agcggtacca atgcagaact cccaagaccc gagctgggac cagtcacctgg gtccccagcc 3480
cttcctctgc tccccctttt ccctcggagt tcttcttgaa tggcaatgtt ttgctttgc  3540
tcgatgcaga caggggggcca gaacaccaca catttcactg tctgtctggt ccatagctgt 3600
ggtgtagggg cttagaggca tgggcttgct gtgggttttt aattgatcag ttttcatgtg 3660
ggatcccatc tttttaacct ctgttcagga agtcctatc tagctgcata tcttcatcat 3720
attggtatat ccttttctgt gtttacagag atgtctctta tatctaaatc tgtccaactg 3780
agaagtacct tatcaaagta gcaaatgaga cagcagtctt atgcttccag aaacacccac 3840
aggcatgtcc catgtgagct gctgccatga actgtcaagt gtgtgttgtc ttgtgtattt 3900
cagttattgt ccctggcttc cttactatgg tgtaatcatg aaggagtgaa acatcataga 3960
aactgtctag cacttccttg ccagtcttta gtgatcagga accatagttg acagttccaa 4020
tcagtagctt aagaaaaac cgtgtttgtc tcttctggaa tggttagaag tgagggagtt 4080
tgccccgttc tgtttgtaga gtctcatagt tggactttct agcatatatg tgtccatttc 4140
cttatgctgt aaaagcaagt cctgcaacca aactcccatc agcccaatcc ctgatccctg 4200
atccccttca cctgctctgc tgatgacccc cccagcttca cttctgactc ttcccccagg 4260
agggaagggg ggtcagaaga gagggtgagt cctccagaac tcttcctcca aggacagaag 4320
gctcctgccc ccatagtggc ctcgaactcc tggcactacc aaaggacact tatccacgag 4380
agcgcagcat ccgaccaggt tgtcactgag aagatgtttta ttttggtcag ttgggttttt 4440
atgtattata cttagtcaaa tgtaatgtgg cttctgaat cattgtccag agctgcttcc 4500
ccgtcacctg ggcgtcatct ggtcctggta agaggagtgc gtggcccacc aggcccccct 4560
gtcacccatg acagttcatt caggccgat ggggcagtcg tggttgggaa cacagcattt 4620
caagcgtcac tttatttcat tcgggcccca cctgcagctc cctcaaagag gcagttgccc 4680
agcctctttc ccttccagtt tattccagag ctgccagtgg ggcctgaggc tccttgggt  4740
tttctctcta tttccccctt tcttcctcat tccctcgtct ttcccaaagg catcacgagt 4800
cagtcgcctt tcagcaggca gccttggcgg tttatcgccc tggcaggcag gggccctgca 4860
gctctcatgc tgcccctgcc ttgggtcag gttgacagga ggttggaggg aaagccttaa 4920
gctgcaggat tctcaccagc tgtgtccggc ccagttttgg ggtgtgacct caatttcaat 4980
tttgtctgta cttgaacatt atgaagatgg gggcctcttt cagtgaattt gtgaacagca 5040
gaattgaccg acagctttcc agtacccatg gggctaggtc attaaggcca catccacagt 5100
ctccccacc cttgttccag ttgttagtta ctacctcctc tcctgacaat actgtatgtc 5160
gtcgagctcc ccccaggtct accctcccg gccctgcctg ctggtgggct tgtcatagcc 5220
agtgggattg ccggtcttga cagctcagtg agctggagat acttggtcac agccaggcgc 5280
tagcacagct cccttctgtt gatgctgtat tcccatatca aaagacacag gggacaccca 5340
gaaacgccac atccccaat ccatcagtgc caaactagca acggcccca gcttctcagc 5400
tcgctgatg gcgaaagctg ctactcgtga gcgccagtgc gggtgcagac aatcttctgt 5460
tgggtggcat cattccaggc ccgaagcatg aacagtgcac ctgggacagg agcagcccc  5520
aaattgtcac ctgcttctct gcccagcttt tcattgctgt gacagtgatg gcgaaagagg 5580
gtaataacca gacacaaact gccaagttgg gtggagaaag gagtttcttt agctgacaga 5640
atctctgaat tttaaatcac ttagtaagcg gctcaagccc aggagggagc agagggatac 5700
gagcggagtc ccctgcgcgg gaccatctgg aattggttta gcccaagtgg agcctgcacg 5760
ccagaactct gtgtcccccg tctaaccaca gctccttttc cagagcattc cagtcaggct 5820
ctctgggctg actgggccag gggaggttac aggtaccagt tctttaagaa gatctttggg 5880
catatacatt tttagcctgt gtcattgccc caaatggatt cctgtttcaa gttcacacct 5940
```

```
gcagattcta ggacctgtgt cctagacttc agggagtcag ctgtttctag agttcctacc   6000
atggagtggg tctggaggac ctgcccggtg gggggcaga gccctgctcc ctccgggtct    6060
tcctactctt ctctctgctc tgacgggatt tgttgattct ctccattttg gtgtctttct   6120
cttttagata ttgtatcaat ctttagaaaa ggcatagtct acttgttata aatcgttagg   6180
atactgcctc ccccagggtc taaaattaca tattagaggg gaaaagctga acactgaagt   6240
cagttctcaa caatttagaa ggaaaaccta gaaacatttt ggcagaaaat tacatttcga   6300
tgttttgaa tgaatacgag caagctttta caacagtgct gatctaaaaa tacttagcac    6360
ttggcctgag atgcctggtg agcattacag gcaaggggaa tctggaggta gccgacctga   6420
ggacatggct tctgaacctg tcttttggga gtggtatgga aggtggagcg ttcaccagtg   6480
acctggaagg cccagcacca ccctccttcc cactcttctc atcttgacag agcctgcccc   6540
agcgctgacg tgtcaggaaa acccaggg aactaggaag gcacttctgc ctgaggggca     6600
gcctgccttg cccactcctg ctctgctcgc ctcggatcag ctgagccttc tgagctggcc   6660
tctcactgcc tccccaaggc cccctgcctg ccctgtcagg aggcagaagg aagcaggtgt   6720
gagggcagtg caaggaggga gcacaacccc cagctcccgc tccgggctcc gacttgtgca   6780
caggcagagc ccagaccctg gaggaaatcc tacctttgaa ttcaagaaca tttggggaat   6840
ttggaaatct ctttgccccc aaaccccat tctgtcctac ctttaatcag gtcctgctca    6900
gcagtgagag cagatgaggt gaaaaggcca agaggtttgg ctcctgccca ctgatagccc   6960
ctctccccgc agtgtttgtg tgtcaagtgg caaagctgtt cttcctggtg accctgatta   7020
tatccagtaa cacatagact gtgcgcatag gcctgctttg tctcctctat cctgggcttt   7080
tgttttgctt tttagttttg cttttagttt ttctgtccct tttatttaac gcaccgacta   7140
gacacacaaa gcagttgaat ttttatatat atatctgtat attgcacaat tataaactca   7200
ttttgcttgt ggctccacac acacaaaaaa agacctgtta aaattatacc tgttgcttaa   7260
ttacaatatt tctgataacc atagcatagg acaaggggaaa ataaaaaaag aaaaaaaaga   7320
aaaaaaaacg acaaatctgt ctgctggtca cttcttctgt ccaagcagat tcgtggtctt   7380
ttcctcgctt ctttcaaggg ctttcctgtg ccaggtgaag gaggctccag gcagcaccca   7440
ggttttgcac tcttgtttct cccgtgcttg tgaaagaggt cccaaggttc tgggtgcagg   7500
agcgctccct tgacctgctg aagtccgaa cgtagtcggc acagcctggt cgccttccac    7560
ctctgggagc tggagtccac tggggtggcc tgactccccc agtcccttc ccgtgacctg    7620
gtcagggtga gcccatgtgg agtcagcctc gcaggcctcc ctgccagtag ggtccgagtg   7680
tgtttcatcc ttcccactct gtcgagcctg ggggctggag cggagacggg aggcctgcc    7740
tgtctcggaa cctgtgagct gcaccaggta gaacgccagg gaccccagaa tcatgtgcgt   7800
cagtccaagg ggtcccctcc aggagtagtg aagactccag aaatgtccct ttcttctccc   7860
ccatcctacg agtaattgca tttgcttttg taattcttaa tgagcaatat ctgctagaga   7920
gtttagctgt aacagttctt tttgatcatc ttttttttaat aattagaaac accaaaaaaa   7980
tccagaaact tgttcttcca aagcagagag cattataatc accagggcca aaagcttccc   8040
tccctgctgt cattgcttct tctgaggcct gaatccaaaa gaaaaacagc cataggccct   8100
ttcagtggcc gggctacccg tgagcccttc ggaggaccag ggctgggca gcctctgggc    8160
ccacatccgg ggccagctcc ggcgtgtgtt cagtgttagc agtgggtcat gatgctcttt   8220
cccacccagc ctgggatagg ggcagaggag gcgaggaggc cgttgccgct gatgtttggc   8280
cgtgaacagg tgggtgtctg cgtgcgtcca cgtgcgtgtt ttctgactga catgaaatcg   8340
acgcccgagt tagcctcacc cggtgacctc tagccctgcc cggatggagc ggggcccacc   8400
cggttcagtg tttctgggga gctggacagt ggagtgcaaa aggcttgcag aacttgaagc   8460
ctgctccttc ccttgctacc acggcctcct ttccgtttga tttgtcactg cttcaatcaa   8520
taacagccgc tccagagtca gtagtcaatg aatatatgac caaatatcac caggactgtt   8580
actcaatgtg tgccgagccc ttgcccatgc tgggctcccg tgtatctgga cactgtaacg   8640
tgtgctgtgt ttgctcccct tcccttcct tctttgccct ttacttgtct ttctggggtt    8700
tttctgtttg ggtttggttt ggttttttatt tctccttttg tgttccaaac atgaggttct   8760
ctctactggt cctcttaact gtggtgttga ggcttatatt tgtgtaattt ttggtgggtg   8820
aaaggaattt tgctaagtaa atctcttctg tgtttgaact gaagtctgta ttgtaactat   8880
gtttaaagta attgttccag agacaaatat ttctagacac ttttttcttta caaacaaaag   8940
cattcggagg gagggggatg gtgactgaga tgagagggga gagctgaaca gatgaccct    9000
gcccagatca gccagaagcc acccaaagca gtggagccca ggagtccac tccaagccag    9060
caagccgaat agctgatgtg ttgccacttt ccaagtcact gcaaaaccag gttttgttcc   9120
gcccagtgga ttcttgtttt gcttcccctc ccccgagat tattaccacc atcccgtgct    9180
tttaaggaaa ggcaagattg atgtttcctt gaggggagcc aggagggat gtgtgtgtgc    9240
agagctgaag agctggggag aatgggggctg ggcccacccca agcaggaggc tgggacgctc  9300
tgctgtgggc acaggtcagg ctaatgttgg cagatgcagc tcttcctgga caggccaggt   9360
ggtgggcatt ctctctccaa ggtgtgcccc gtgggcatta ctgtttaaga cacttccgtc   9420
acatcccacc ccatcctcca gggctcaaca ctgtgacatc tctattcccc ccctcccc    9480
tcccagggca ataaaatgac catggagggg gcttgcactc tcttggctgt caccccgatcg  9540
ccagcaaaac ttagatgtga gaaaaccccct tcccattcca tggcgaaaac atctccttag   9600
aaaagccatt accctcatta ggcatggttt tgggctccca aaacacctga cagcccctcc   9660
ctcctctgag aggcggagag tgctgactgt agtgaccatt gcatgccggg tgcagcatct   9720
ggaagagcta ggcagggtgt ctgccccctc ctgagttgaa gtcatgctcc cctgtgccag   9780
cccagaggcc gagagctatg acagcattg ccagtaacac aggccaccct gtgcagaagg    9840
gagctggctc cagcctggaa acctgtctga ggttgggaga ggtgcacttg gggcacaggg   9900
agaggccggg acacacttag ctggagatgt ctctaaaagc cctgtatcgt attcaccttc   9960
agtttttgtg tttttgggaca attactttag aaaataagta ggtcgttta aaaacaaaaa   10020
ttattgattg ctttttttgta gtgttcagaa aaaaggttct ttgtgtatag ccaaatgact   10080
gaaagcactg atatatttaa aaacaaaagg caatttatta aggaaatttg taccatttca   10140
gtaaacctgt ctgaatgtac ctgtatacgt ttcaaaaaca cccccccccc actgaatccc   10200
tgtaacctat ttattatata aagagtttgc cttataaatt t                       10241
```

SEQ ID NO: 3            moltype = DNA  length = 19
FEATURE                 Location/Qualifiers
source                  1..19
                        mol_type = other DNA
                        organism = synthetic construct
SEQUENCE: 3

-continued

```
caaggccaaa cagagagga                                              19

SEQ ID NO: 4            moltype = DNA   length = 20
FEATURE                 Location/Qualifiers
source                  1..20
                        mol_type = other DNA
                        organism = synthetic construct
SEQUENCE: 4
ttgtcagagc cctacccata                                             20

SEQ ID NO: 5            moltype = DNA   length = 29
FEATURE                 Location/Qualifiers
source                  1..29
                        mol_type = other DNA
                        organism = synthetic construct
SEQUENCE: 5
agaataaagg cagctgttgt ctcttctcc                                   29

SEQ ID NO: 6            moltype = DNA   length = 25
FEATURE                 Location/Qualifiers
source                  1..25
                        mol_type = other DNA
                        organism = synthetic construct
SEQUENCE: 6
tgaaggagtc ttctatccga tctgt                                       25

SEQ ID NO: 7            moltype = DNA   length = 21
FEATURE                 Location/Qualifiers
source                  1..21
                        mol_type = other DNA
                        organism = synthetic construct
SEQUENCE: 7
cacttccttg acctcgatgc t                                           21

SEQ ID NO: 8            moltype = DNA   length = 26
FEATURE                 Location/Qualifiers
source                  1..26
                        mol_type = other DNA
                        organism = synthetic construct
SEQUENCE: 8
agaccgtact ccccatcaag aagcgc                                      26

SEQ ID NO: 9            moltype = DNA   length = 20
FEATURE                 Location/Qualifiers
source                  1..20
                        mol_type = other DNA
                        organism = synthetic construct
SEQUENCE: 9
ggcaaattca acggcacagt                                             20

SEQ ID NO: 10           moltype = DNA   length = 20
FEATURE                 Location/Qualifiers
source                  1..20
                        mol_type = other DNA
                        organism = synthetic construct
SEQUENCE: 10
gggtctcgct cctggaagat                                             20

SEQ ID NO: 11           moltype = DNA   length = 27
FEATURE                 Location/Qualifiers
source                  1..27
                        mol_type = other DNA
                        organism = synthetic construct
SEQUENCE: 11
aaggccgaga atgggaagct tgtcatc                                     27

SEQ ID NO: 12           moltype = DNA   length = 21
FEATURE                 Location/Qualifiers
source                  1..21
                        mol_type = other DNA
                        organism = synthetic construct
SEQUENCE: 12
gatcaatccc cagggaaaag c                                           21

SEQ ID NO: 13           moltype = DNA   length = 21
FEATURE                 Location/Qualifiers
source                  1..21
                        mol_type = other DNA
                        organism = synthetic construct
```

```
SEQUENCE: 13
cctctcccag ttaccgtgaa g                                          21

SEQ ID NO: 14           moltype = DNA   length = 24
FEATURE                 Location/Qualifiers
source                  1..24
                        mol_type = other DNA
                        organism = synthetic construct
SEQUENCE: 14
cattagggtc cagggatgtg tcgc                                       24

SEQ ID NO: 15           moltype = DNA   length = 19
FEATURE                 Location/Qualifiers
source                  1..19
                        mol_type = other DNA
                        organism = synthetic construct
SEQUENCE: 15
gaaggtgaag gtcggagtc                                             19

SEQ ID NO: 16           moltype = DNA   length = 20
FEATURE                 Location/Qualifiers
source                  1..20
                        mol_type = other DNA
                        organism = synthetic construct
SEQUENCE: 16
gaagatggtg atgggatttc                                            20

SEQ ID NO: 17           moltype = DNA   length = 20
FEATURE                 Location/Qualifiers
source                  1..20
                        mol_type = other DNA
                        organism = synthetic construct
SEQUENCE: 17
caagcttccc gttctcagcc                                            20

SEQ ID NO: 18           moltype = DNA   length = 20
FEATURE                 Location/Qualifiers
source                  1..20
                        mol_type = other DNA
                        organism = synthetic construct
SEQUENCE: 18
gcaacatttt cagtttcagc                                            20

SEQ ID NO: 19           moltype = DNA   length = 20
FEATURE                 Location/Qualifiers
source                  1..20
                        mol_type = other DNA
                        organism = synthetic construct
modified_base           1
                        mod_base = OTHER
                        note = 2'-O-methoxyethyl guanosine 3'-phosphorothioate
modified_base           2
                        mod_base = OTHER
                        note = 2'-O-methoxyethyl 5-methylcytidine 3'-phosphodiester
modified_base           3..4
                        mod_base = OTHER
                        note = 2'-O-methoxyethyl adenosine 3'-phosphodiester
modified_base           5
                        mod_base = OTHER
                        note = 2'-O-methoxyethyl 5-methylcytidine 3'-phosphodiester
```

| | | |
|---|---|---|
| modified_base | 6 | |
| | mod_base = OTHER | |
| | note = 2'-deoxy adenosine 3'-phosphorothioate | |
| modified_base | 7..10 | |
| | mod_base = OTHER | |
| | note = 2'-deoxy thymidine 3'-phosphorothioate | |
| modified_base | 11 | |
| | mod_base = OTHER | |
| | note = 2'-deoxy 5-methylcytidine 3'-phosphorothioate | |
| modified_base | 12 | |
| | mod_base = OTHER | |
| | note = 2'-deoxy adenosine 3'-phosphorothioate | |
| modified_base | 13 | |
| | mod_base = OTHER | |
| | note = 2'-deoxy guanosine 3'-phosphorothioate | |
| modified_base | 14..15 | |
| | mod_base = OTHER | |
| | note = 2'-deoxy thymidine 3'-phosphorothioate | |
| modified_base | 16 | |
| | mod_base = OTHER | |
| | note = 2'-O-methoxyethyl thymidine 3'-phosphodiester | |
| modified_base | 17 | |
| | mod_base = OTHER | |
| | note = 2'-O-methoxyethyl 5-methylcytidine 3'-phosphodiester | |
| modified_base | 18 | |
| | mod_base = OTHER | |
| | note = 2'-O-methoxyethyl adenosine 3'-phosphorothioate | |
| modified_base | 19 | |
| | mod_base = OTHER | |
| | note = 2'-O-methoxyethyl guanosine 3'-phosphorothioate | |
| modified_base | 20 | |
| | mod_base = OTHER | |
| | note = 2'-O-methoxyethyl 5-methylcytidine | |
| SEQUENCE: 19 | | |
| gcaacattttt cagtttcagc | | 20 |
| | | |
| SEQ ID NO: 20 | moltype = DNA   length = 20 | |
| FEATURE | Location/Qualifiers | |
| source | 1..20 | |
| | mol_type = other DNA | |
| | organism = synthetic construct | |
| SEQUENCE: 20 | | |
| ggtttttctc ctttattatc | | 20 |
| | | |
| SEQ ID NO: 21 | moltype = DNA   length = 20 | |
| FEATURE | Location/Qualifiers | |
| source | 1..20 | |
| | mol_type = other DNA | |
| | organism = synthetic construct | |
| SEQUENCE: 21 | | |
| tatggttttt ctcctttatt | | 20 |